United States Patent
Candell et al.

(10) Patent No.: US 10,925,513 B2
(45) Date of Patent: Feb. 23, 2021

(54) SYSTEMS, APPARATUS, AND METHODS RELATED TO MODELING, MONITORING, AND/OR MANAGING METABOLISM

(71) Applicant: Massachusetts Institute of Technology, Cambridge, MA (US)

(72) Inventors: Lawrence M. Candell, Arlington, MA (US); Christopher Ferraiolo, Newburyport, MA (US); Gary A. Shaw, Westford, MA (US); Andrew M. Siegel, Arlington, MA (US); George Zogbi, Arlington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 865 days.

(21) Appl. No.: 15/221,313

(22) Filed: Jul. 27, 2016

(65) Prior Publication Data
US 2017/0055875 A1    Mar. 2, 2017

Related U.S. Application Data

(60) Provisional application No. 62/197,324, filed on Jul. 27, 2015.

(51) Int. Cl.
*A61B 5/083* (2006.01)
*A61B 5/08* (2006.01)
(Continued)

(52) U.S. Cl.
CPC .............. *A61B 5/083* (2013.01); *A61B 5/082* (2013.01); *A61B 5/0816* (2013.01);
(Continued)

(58) Field of Classification Search
None
See application file for complete search history.

(56) References Cited

U.S. PATENT DOCUMENTS

| 2,630,798 A | 3/1953 | White et al. |
| 4,934,386 A | 6/1990 | Walker et al. |

(Continued)

FOREIGN PATENT DOCUMENTS

| WO | 2014116604 A1 | 7/2014 |
| WO | 2015011714 A1 | 1/2015 |

OTHER PUBLICATIONS

Extended European Search Report in European Patent Application No. 16831300.5 dated Feb. 19, 2019, 11 pages.

(Continued)

*Primary Examiner* — Jacqueline Cheng
*Assistant Examiner* — Jairo H Portillo
(74) *Attorney, Agent, or Firm* — Smith Baluch LLP

(57) ABSTRACT

Systems, apparatus, and methods related to modeling, monitoring, and/or managing metabolism of a subject include measuring a respiratory quotient (RQ) level in a subject and/or optimizing and executing a nonlinear feedback model to model energy substrate utilization in the subject based on at least one of a macronutrient composition and caloric value of food consumed by the subject, an intensity and duration of activity by the subject, a rate and maximum capacity of glycogen storage in the subject, a rate and maximum capacity of de novo lipogenesis in the subject, a quality and duration of sleep by the subject, and/or an RQ level in the subject.

30 Claims, 29 Drawing Sheets

(51) Int. Cl.
*A61B 5/097* (2006.01)
*A61B 5/00* (2006.01)
*G09B 19/00* (2006.01)
*A61B 5/087* (2006.01)

(52) U.S. Cl.
CPC .......... *A61B 5/0833* (2013.01); *A61B 5/0836* (2013.01); *A61B 5/097* (2013.01); *A61B 5/4866* (2013.01); *G09B 19/00* (2013.01); *G09B 19/0092* (2013.01); *A61B 5/0871* (2013.01); *A61B 5/7275* (2013.01); *A61B 2560/0223* (2013.01); *A61B 2560/0247* (2013.01)

(56) References Cited

U.S. PATENT DOCUMENTS

| | | | |
|---|---|---|---|
| 5,072,737 A | 12/1991 | Goulding | |
| 5,363,857 A * | 11/1994 | Howard | A61B 5/02055 600/531 |
| 5,555,890 A | 9/1996 | Schaller | |
| 6,884,222 B1 | 4/2005 | Braig | |
| 6,969,357 B1 * | 11/2005 | Colman | A61B 5/083 422/84 |
| 8,197,417 B2 | 6/2012 | Howard et al. | |
| 2002/0017467 A1 * | 2/2002 | Ando | F01N 3/0842 205/781 |
| 2004/0094155 A1 | 5/2004 | Castor et al. | |
| 2004/0186389 A1 * | 9/2004 | Mault | A61B 5/0833 600/531 |
| 2004/0186390 A1 * | 9/2004 | Ross | A61B 5/083 600/532 |
| 2006/0201503 A1 | 9/2006 | Breen | |
| 2006/0229526 A1 | 10/2006 | Chen et al. | |
| 2008/0119752 A1 * | 5/2008 | Flanagan | A61B 5/0833 600/531 |
| 2008/0289628 A1 | 11/2008 | Hallback et al. | |
| 2009/0056409 A1 * | 3/2009 | Howard | A61B 5/0836 73/1.07 |
| 2009/0227887 A1 * | 9/2009 | Howard | A61B 5/0833 600/531 |
| 2010/0036266 A1 | 2/2010 | Myklebust et al. | |
| 2010/0185112 A1 | 7/2010 | Kesteren et al. | |
| 2010/0313963 A1 * | 12/2010 | Skinn | C12M 41/34 137/3 |
| 2011/0009764 A1 * | 1/2011 | Lanier | A61B 5/0833 600/532 |
| 2012/0029321 A1 | 2/2012 | Makaretz et al. | |
| 2012/0125335 A1 * | 5/2012 | Affinito | A61M 15/00 128/204.15 |
| 2012/0130698 A1 | 5/2012 | Kovatchev et al. | |
| 2013/0184619 A1 | 7/2013 | Hollen et al. | |
| 2014/0128691 A1 | 5/2014 | Olivier | |
| 2014/0180033 A1 * | 6/2014 | Altini | A61B 5/1118 600/301 |
| 2014/0194703 A1 * | 7/2014 | Wondka | A61B 5/02055 600/301 |
| 2014/0235961 A1 | 8/2014 | Brugnoli | |
| 2015/0032019 A1 | 1/2015 | Acker et al. | |
| 2015/0033824 A1 | 2/2015 | Hammarlund et al. | |
| 2015/0065900 A1 * | 3/2015 | Wondka | A61B 5/0836 600/531 |
| 2015/0114395 A1 | 4/2015 | Heinonen et al. | |
| 2015/0177103 A1 * | 6/2015 | Brown | G01M 15/102 73/1.07 |
| 2016/0166175 A1 | 6/2016 | Mor et al. | |
| 2016/0220147 A1 | 8/2016 | Mor et al. | |
| 2018/0125391 A1 | 5/2018 | Candell et al. | |

OTHER PUBLICATIONS

Reeves et al., "Reducing the time period of steady state does not affect the accuracy of energy expenditure measurements by indirect calorimetry." Journal of applied physiology 97.1 (2004): 130-134.
International Search Report and Written Opinion dated Dec. 30, 2016 for International Application No. PCT/US16/44288, 13 pages.
Acheson et al., Am. J. Clin. Nutrition, 48:240-47 (1988).
Bouchard et al., Obesity Res., 2(5):400-10 (1994).
Cruickshank et al., J. Physiol., 80(2):179-92 (1933).
Ganz et al., Diabetology & Metabolic Syndrome, 6(50): 1-8 (2014).
Guh et al., BMC Public Health, 9(88):1-20 (2009).
Hargrove, J. Nutrition, 136(12):2957-61 (2006).
Jebb et al., Am. J. Clin. Nutrition, 58:455-62 (1993).
Ladenheim, Drug Design, Dev. & Therapy, 1867-75 (2015).
Ludwig et al., JAMA, 311(21):2167-68 (2014).
McDevitt et al., Am. J. Clin. Nutrition, 74(6):737-46 (2001).
Mozaffarian et al., NEJM, 364(25):2392-2404 (2011).
Weiss et al., N. Eng. J. Med., 350(23):2362-74 (2004).
Levi et al., "F as in fat: how obesity threatens America's future 2012." (2012). 116 pages.
Hall, "Estimating human energy intake using mathematical models," American Journal of Clinical Nutrition, 2014;100:744-5.

\* cited by examiner

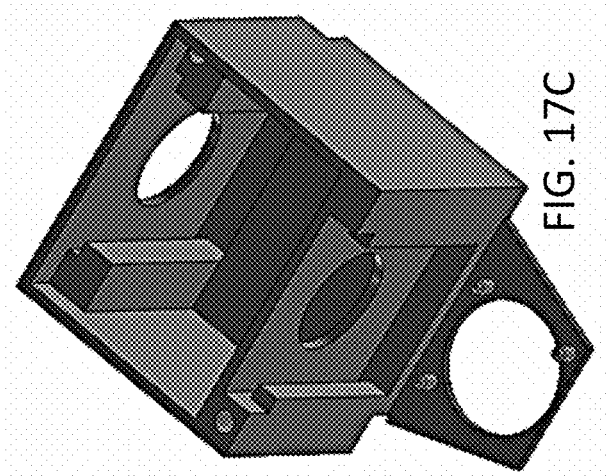
FIG. 17C
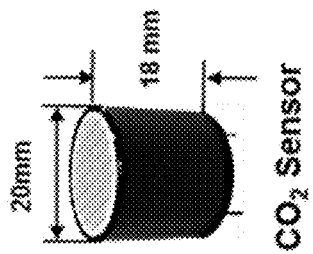
CO₂ Sensor
FIG. 17G
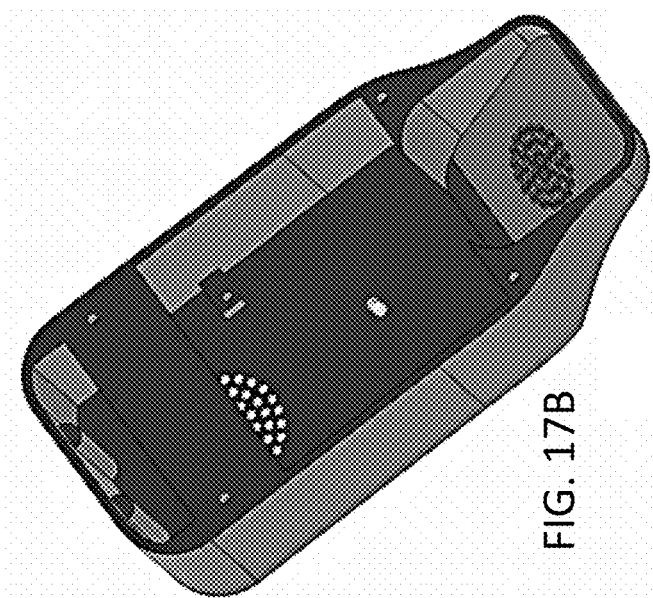
FIG. 17B
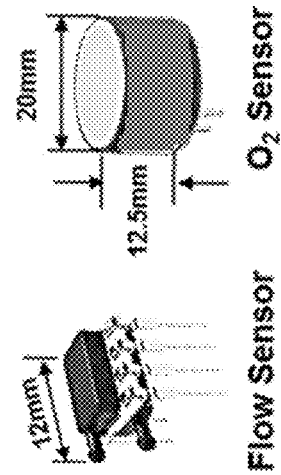
O₂ Sensor
FIG. 17F
Flow Sensor
FIG. 17E
FIG. 17A
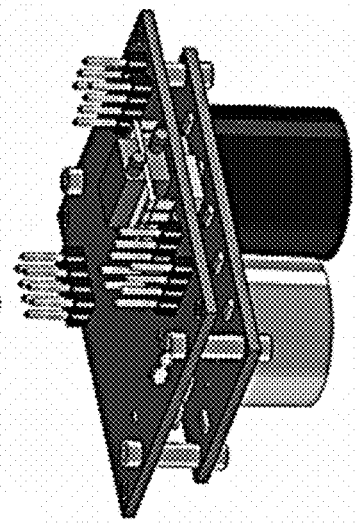
FIG. 17D

SYSTEMS, APPARATUS, AND METHODS RELATED TO MODELING, MONITORING, AND/OR MANAGING METABOLISM

CROSS-REFERENCE TO RELATED APPLICATIONS

This application claims a priority benefit of U.S. Provisional Patent Application 62/197,324, filed on Jul. 27, 2015, and entitled "Systems, Apparatus, and Methods for Modeling, Monitoring, and Managing Metabolism," which application is incorporated herein by reference in its entirety.

GOVERNMENT SUPPORT STATEMENT

This invention was made with Government support under Contract No. FA8721-05-C-0002 awarded by the U.S. Air Force. The Government has certain rights in the invention.

TECHNICAL FIELD

The present disclosure relates generally to biofeedback systems, apparatus, and methods. More specifically, the present disclosure relates to systems, apparatus, and methods related to modeling, monitoring, and/or managing a metabolic state of a subject.

BACKGROUND

Obesity in humans has steadily increased worldwide. This trend is not just confined to adults-currently, over one-third of U.S. adults are obese-but also evident in children and adolescents. Comorbidities associated with obesity include type 2 diabetes, cancer (e.g., pancreatic and prostate cancers), cardiovascular disease, asthma, gallbladder disease, osteoarthritis, and chronic back pain. The most prevalent comorbidity associated with obesity is type 2 diabetes, which is estimated to cost the United States in excess of $300 billion per year.

Diet plans for preventing or reducing obesity provide often conflicting and sometimes even diametrically opposed advice for which macronutrients promote weight loss. More recently, the "calorie-in/calorie-out" (CICO) model of metabolism has increased in popularity. The use of the calorie to attribute energy to food sources has been in place since the mid-1800s. FIG. 1 is a diagram illustrating the "calorie-in/calorie-out" (CICO) model 100, which posits that an imbalance between a subject's energy needs (calories out 102, e.g., 1500-3000 Cal/day) and the amount of calories that the subject consumes (calories in 104, e.g., 1000-3000 Cal/day) results in either weight gain (virtually unlimited calorie storage 106) or weight loss (calorie burning 108). That is, if the subject consumes calories in excess of the subject's energy needs, the excess calories will not be burned or excreted, but rather stored as glycogen or as adipose tissue, thereby contributing to obesity and comorbidities.

Many diet plans now rely on tracking food calories as a simplistic means to manage weight. Diet plans that are structured around the CICO model promote overt control of calorie intake and/or an exercise regimen to create an energy imbalance.

While the CICO model relies on the first law of thermodynamics (i.e., energy cannot be created or destroyed), the underlying assumption of the CICO model is that all food calories are alike. As such, calorie counting and other diet plans that are structured around the CICO model are not only tedious to implement and prone to error, but often ignore the impact that different macronutrient mixes and exercise intensities have on an individual's homeostatic control system. As a consequence, diet plans focused solely on energy balance (the CICO model) have failed to reduce the worldwide trend of increasing obesity and comorbidities despite their popularity.

SUMMARY

The inventors have recognized and appreciated that existing metabolic models, particularly the CICO model, fail to capture the physiological complexity of metabolism and therefore do not provide sufficient guidance to reverse obesity trends in individuals or populations. Instead, the inventors herein provide a metabolic state model based on avoiding elevated blood glucose levels through proper selection of dietary macronutrients and exercise sufficient to enable the body's homeostatic system to achieve and maintain a healthy body weight according to some embodiments.

In part, the inventors have recognized and appreciated that the kinds of foods consumed and activities performed by a subject, in concert with their unique genetic makeup, directly influence the subject's metabolic state-fat/carbohydrate/protein burning, fat/carbohydrate/protein storing, or neutral- and thereby account greatly for weight gain and weight loss. According to some embodiments, the inventors have developed personal respiratory quotient (RQ) measurement devices and methods for providing on-demand feedback indicative of a subject's real-time metabolic state and guiding the subject's macronutrient intake and/or activity levels to promote a desired metabolic state and/or achieve and maintain a healthy body weight.

In one embodiment, a system for managing metabolism of a subject includes at least one input device for obtaining data related to the subject, at least one memory device for storing the data related to the subject and processor-executable instructions, and at least one processor in communication with the at least one input device and the at least one memory device. Upon execution of the processor-executable instructions, the at least one processor determines, from the data related to the subject, metabolic data characterizing energy substrate utilization in the subject, the metabolic data including RQ data acquired from the subject, and controls operation of a nonlinear feedback model to determine, based on the metabolic data, a target value of one or more energy substrate utilization variables, at least one of which maintains and alters energy substrate utilization in the subject. The nonlinear feedback model is optimized to model energy substrate utilization in the subject based on at least one of a macronutrient composition and caloric value of food consumed by the subject, an intensity and duration of activity by the subject, a rate and maximum capacity of glycogen storage in the subject, a rate and maximum capacity of de novo lipogenesis in the subject, and a quality and duration of sleep by the subject. The one or more energy substrate utilization variables include at least one of the macronutrient composition and caloric value of food consumed by the subject and the intensity and duration of activity by the subject.

In one embodiment, a system for optimizing a nonlinear feedback model of energy substrate utilization in a subject includes at least one input device for obtaining data related to the subject, at least one memory device for storing the data related to the subject and processor-executable instructions, and at least one processor in communication with the at least one input device and the at least one memory device.

Upon execution of the processor-executable instructions, the at least one processor determines from the data related to the subject a macronutrient composition and caloric value of food consumed by the subject, an intensity and duration of activity by the subject, a rate and maximum capacity of glycogen storage in the subject, and a rate and maximum capacity of de novo lipogenesis in the subject. The at least one processor further optimizes the nonlinear feedback model to model energy substrate utilization in the subject based on the macronutrient composition and caloric value of food consumed by the subject, the intensity and duration of activity by the subject, the rate and maximum capacity of glycogen storage in the subject, and the rate and maximum capacity of de novo lipogenesis in the subject.

In one embodiment, a system for managing body weight of a subject includes at least one input device for obtaining data related to the subject, at least one memory device for storing the data related to the subject and processor-executable instructions, and at least one processor in communication with the at least one input device and the at least one memory device. Upon execution of the processor-executable instructions, the at least one processor determines from the data related to the subject at least one initial physiological parameter associated with the subject, the at least one initial physiological parameter including an initial body weight of the subject, and controls operation of a nonlinear feedback model to determine, based on the at least one initial physiological parameter, a target value of one or more energy substrate utilization variables that at least one of maintains and alters the body weight of the subject. The nonlinear feedback model is optimized to model energy substrate utilization in the subject based on at least one of a macronutrient composition and caloric value of food consumed by the subject, an intensity and duration of activity by the subject, a rate and maximum capacity of glycogen storage in the subject, a rate and maximum capacity of de novo lipogenesis in the subject, and a quality and duration of sleep by the subject. The one or more energy substrate utilization variables comprise at least one of the macronutrient composition and caloric value of food consumed by the subject and the intensity and duration of activity by the subject.

In one embodiment, an apparatus for measuring an RQ level in a subject includes a first input port for receiving respired air from the subject, a measurement chamber for receiving the respired air from the first input port, the measurement chamber being in fluid communication with the first input port, a first sensor located in the measurement chamber, the first sensor for measuring a series of oxygen levels in the measurement chamber, a second sensor located in the measurement chamber, the second sensor for measuring a series of carbon dioxide levels in the measurement chamber at a temporal rate sufficient to ascertain a respiration rate of the subject, at least one output interface, at least one memory for storing processor-executable instructions, the series of oxygen level measurements, and the series of carbon dioxide level measurements, and at least one processor coupled to the first sensor, the second sensor, the at least one output interface, and the at least one memory. Upon execution of the processor-executable instructions, the at least one processor obtains a first portion of the series of carbon dioxide level measurements, determines a first respiration rate based on the first portion of the series of carbon dioxide level measurements. The at least one processor further iterates steps of obtaining a subsequent portion of the series of carbon dioxide level measurements, determining a subsequent respiration rate based on the subsequent portion of the series of carbon dioxide level measurements, and comparing the subsequent respiration rate to at least one prior respiration rate until a stable breathing pattern is identified. The at least one processor then obtains a stable breathing pattern portion of the series of oxygen level measurements and a stable breathing pattern portion of the series of carbon dioxide level measurements, determines an average minimum oxygen level for a respiration cycle from the stable breathing pattern portion of the series of oxygen level measurements, determines an average maximum carbon dioxide level for a respiration cycle from the stable breathing pattern portion of the series of carbon dioxide level measurements, calculates the RQ level from the average minimum oxygen level and the average maximum carbon dioxide level, and at least one of displays and transmits, via the at least one output interface, the calculated RQ level.

In an embodiment, the at least one processor controls an ambient air calibration process including the steps of comparing at least one measurement to at least one expected value for ambient air. If the at least one measurement is from the first sensor and sufficiently different from the at least one expected value for ambient air, the at least one processor may perform a span calibration process on the first sensor to determine and apply a gain correction to subsequent measurements from the first sensor. If the at least one measurement is from the second sensor and sufficiently different from the at least one expected value for ambient air, the at least one processor may perform a zero-point calibration process on the second sensor to determine and apply an offset correction to subsequent measurements from the second sensor.

In an embodiment, the at least one expected value for ambient air at 760 mm Hg is at least one of about 19.5% (v/v) to about 23.5% (v/v) oxygen and about 250 ppm to about 5,000 ppm carbon dioxide. The at least one expected value for ambient air at 760 mm Hg may be at least one of about 20.9% (v/v) oxygen and about 400 ppm carbon dioxide. The ambient air calibration process may be performed each time the first sensor and the second sensor are initiated. The ambient air calibration may also employ measured relative humidity to adjust the percent oxygen to account for water vapor content. The ambient air calibration process further may include storing in the at least one memory at least one of the gain correction applied to subsequent measurements from the first sensor and the offset correction applied to subsequent measurements from the second sensor, such that a history of ambient air measurement drift is maintained for reference.

In an embodiment, the apparatus further includes a second input port for receiving a carbon dioxide cartridge for calibrating at least one of the first sensor and the second sensor, the second input port being in fluid communication with the measurement chamber such that the measurement chamber receives carbon dioxide released from the carbon dioxide cartridge.

In an embodiment, the at least one processor controls a full calibration process, the full calibration process including allowing the measurement chamber to fill with ambient air, setting a span value for the first sensor to an expected value for the ambient air, setting a zero-point value for the second sensor to an expected value for the ambient air, coupling the second input port with the carbon dioxide cartridge for releasing carbon dioxide from the carbon dioxide cartridge, releasing the carbon dioxide into the measurement chamber, setting a zero-point value for the first sensor to zero once the carbon dioxide displaces the ambient air in the measurement chamber, and iteratively measuring oxygen levels with the first sensor in the measurement chamber as the ambient air displaces the carbon dioxide in the measurement chamber until a predetermined oxygen level is measured, the predetermined oxygen level indicating the span value for the second sensor. The predetermined oxygen level may be about 16.7%, and the span value for the second sensor may be about 20%.

In an embodiment, the apparatus further includes a component timed to prevent fluid communication between the first input port and the measurement chamber during an initial portion of each respiration cycle and allow fluid communication between the first input port and the measurement chamber during an end-tidal portion of each respiration cycle. The timed component may be at least one of a mechanical shutter, a vacuum pump, and a purge fan. The first input port may be compatible with at least one of a mouthpiece and a sample tube for coupling the input port to at least one of the mouth and a nostril of the subject. The at least one of the mouthpiece and the sample tube may be at least one of disposable and for hands-free use. The mouthpiece may be a repurposed sport bottle cap. The apparatus further may include a heating element for at least one of preventing and reducing condensation on the first sensor and the second sensor.

In one embodiment, a kit for measuring an RQ level in a subject includes a carbon dioxide cartridge, at least one of a mouthpiece and a sample tube for coupling to at least one of the mouth and a nostril of the subject, and a device for measuring the RQ level in a subject. The device includes a first input port for receiving, via the at least one of the mouthpiece and the sample tube, respired air from the subject, a measurement chamber for receiving the respired air from the first input port, the measurement chamber being in fluid communication with the first input port, a first sensor located in the measurement chamber, the first sensor for measuring a series of oxygen levels in the measurement chamber, a second sensor located in the measurement chamber, the second sensor for measuring a series of carbon dioxide levels in the measurement chamber at a temporal rate sufficient to ascertain a respiration rate of the subject, a second input port for receiving the carbon dioxide cartridge for calibrating at least one of the first sensor and the second sensor, the second input port being in fluid communication with the measurement chamber such that the measurement chamber receives carbon dioxide released from the carbon dioxide cartridge, at least one output interface, at least one memory for storing processor-executable instructions, the series of oxygen level measurements, and the series of carbon dioxide level measurements, at least one processor coupled to the first sensor, the second sensor, the at least one output interface, and the at least one memory. Upon execution of the processor-executable instructions, the at least one processor obtains a first portion of the series of carbon dioxide level measurements, determines a first respiration rate based on the first portion of the series of carbon dioxide level measurements, iterates steps of obtaining a subsequent portion of the series of carbon dioxide level measurements, determining a subsequent respiration rate based on the subsequent portion of the series of carbon dioxide level measurements, and comparing the subsequent respiration rate to at least one prior respiration rate until a stable breathing pattern is identified, obtains a stable breathing pattern portion of the series of oxygen level measurements and a stable breathing pattern portion of the series of carbon dioxide level measurements, determines an average minimum oxygen level for a respiration cycle from the stable breathing pattern portion of the series of oxygen level measurements, determines an average maximum carbon dioxide level for a respiration cycle from the stable breathing pattern portion of the series of carbon dioxide level measurements, calculates the RQ level from the average minimum oxygen level and the average maximum carbon dioxide level, and at least one of displays and transmits, via the at least one output interface, the calculated RQ level.

In one embodiment, a computer-facilitated method for measuring an RQ level in a subject includes receiving, in a measurement chamber via an input port in fluid communication with the measurement chamber, respired air from the subject, obtaining, via a first sensor located in the measurement chamber, a first portion of a series of oxygen level measurements, obtaining, via a second sensor located in the measurement chamber, a first portion of a series of carbon dioxide level measurements, and determining, via at least one processor, a first respiration rate based on the first portion of the series of carbon dioxide level measurements. The method further includes iterating steps of obtaining a subsequent portion of the series of carbon dioxide level measurements, determining, via the at least one processor, a subsequent respiration rate based on the subsequent portion of the series of carbon dioxide level measurements, and comparing, via the at least one processor, the subsequent respiration rate to at least one prior respiration rate until a stable breathing pattern is identified. The method then includes obtaining a stable breathing pattern portion of the series of oxygen level measurements and a stable breathing pattern portion of the series of carbon dioxide level measurements, determining, via the at least one processor, an average minimum oxygen level for a respiration cycle from the stable breathing pattern portion of the series of oxygen level measurements, determining, via the at least one processor, an average maximum carbon dioxide level for a respiration cycle from the stable breathing pattern portion of the series of carbon dioxide level measurements, calculating, via the at least one processor, the RQ level from the average minimum oxygen level and the average maximum carbon dioxide level, and at least one of displaying and transmitting, via at least one output interface, the calculated RQ level.

In one embodiment, a computer-facilitated method for managing metabolism of a subject includes determining from data related to the subject obtained via at least one input device a macronutrient composition and caloric value of food consumed by the subject, an intensity and duration of activity by the subject, a rate and maximum capacity of glycogen storage in the subject, and a rate and maximum capacity of de novo lipogenesis in the subject. The method also includes optimizing, via at least one processor, a nonlinear feedback model to model energy substrate utilization in the subject based on the macronutrient composition and caloric value of food consumed by the subject, the intensity and duration of activity by the subject, the rate and maximum capacity of glycogen storage in the subject, and the rate and maximum capacity of de novo lipogenesis in the subject. The method further includes obtaining metabolic data for the energy substrate utilization in the subject, the metabolic data including RQ data acquired from the subject, and controlling, via the at least one processor, operation of the optimized nonlinear feedback model based on the metabolic data to determine a target value of one or more energy substrate utilization variables that at least one of maintains and increases energy substrate utilization in the subject. The one or more energy substrate utilization variables include at least one of the macronutrient composition and caloric value of food consumed by the subject and the intensity and duration of activity by the subject.

In one embodiment, a computer-facilitated method for managing metabolism of a subject includes determining from data related to the subject obtained via at least one input device at least one of a macronutrient composition and caloric value of food consumed by the subject, an intensity and duration of activity by the subject, a rate and maximum capacity of glycogen storage in the subject, a rate and maximum capacity of de novo lipogenesis in the subject, and a quality and duration of sleep by the subject. The method also includes optimizing, via at least one processor, a nonlinear feedback model to model energy substrate utilization in the subject based on at least one of the macronutrient composition and caloric value of food consumed by the subject, the intensity and duration of activity by the subject, the rate and maximum capacity of glycogen storage in the subject, the rate and maximum capacity of de novo lipogenesis in the subject, and the quality and duration of sleep by the subject. The method further includes obtaining metabolic data for the energy substrate utilization in the subject, the metabolic data including RQ data acquired from the subject, and controlling, via the at least one processor, operation of the optimized nonlinear feedback model based on the metabolic data to determine a target value of one or more energy substrate utilization variables that at least one of maintains and increases energy substrate utilization in the subject. The one or more energy substrate utilization variables include at least one of the macronutrient composition and caloric value of food consumed by the subject and the intensity and duration of activity by the subject.

In one embodiment, a computer-facilitated method for modeling metabolism in a subject includes determining from data related to the subject obtained via at least one input device a macronutrient composition and caloric value of food consumed by the subject, an intensity and duration of activity by the subject, a rate and maximum capacity of glycogen storage in the subject, and a rate and maximum capacity of de novo lipogenesis in the subject. The method also includes optimizing, via at least one processor, a nonlinear feedback model to model energy substrate utilization in the subject based on the macronutrient composition and caloric value of food consumed by the subject, the intensity and duration of activity by the subject, the rate and maximum capacity of glycogen storage in the subject, and the rate and maximum capacity of de novo lipogenesis in the subject.

In one embodiment, a computer-facilitated method for managing body weight of a subject includes determining from data related to the subject obtained via at least one input device a macronutrient composition and caloric value of food consumed by the subject, an intensity and duration of activity by the subject, a rate and maximum capacity of glycogen storage in the subject, and a rate and maximum capacity of de novo lipogenesis in the subject. The method also includes optimizing, via at least one processor, a nonlinear feedback model to model energy substrate utilization in the subject based on the macronutrient composition and caloric value of food consumed by the subject, the intensity and duration of activity by the subject, the rate and maximum capacity of glycogen storage in the subject, and the rate and maximum capacity of de novo lipogenesis in the subject. The method further includes obtaining at least one initial physiological parameter associated with the subject, the at least one initial physiological parameter including an initial body weight of the subject, and controlling, via the at least one processor, operation of the optimized nonlinear feedback model based on the at least one initial physiological parameter to determine a target value of one or more energy substrate utilization variables that at least one of maintains and alters the body weight of the subject. The one or more energy substrate utilization variables include at least one of the macronutrient composition and caloric value of food consumed by the subject and the intensity and duration of activity by the subject.

In one embodiment, a computer-facilitated method for managing body weight of a subject includes determining from data related to the subject obtained via at least one input device at least one of a macronutrient composition and caloric value of food consumed by the subject, an intensity and duration of activity by the subject, a rate and maximum capacity of glycogen storage in the subject, a rate and maximum capacity of de novo lipogenesis in the subject, and a quality and duration of sleep by the subject. The method also includes optimizing, via at least one processor, a nonlinear feedback model to model energy substrate utilization in the subject based on at least one of the macronutrient composition and caloric value of food consumed by the subject, the intensity and duration of activity by the subject, the rate and maximum capacity of glycogen storage in the subject, the rate and maximum capacity of de novo lipogenesis in the subject, and the quality and duration of sleep by the subject. The method further includes obtaining at least one initial physiological parameter associated with the subject, the at least one initial physiological parameter including an initial body weight of the subject, and controlling, via the at least one processor, operation of the optimized nonlinear feedback model based on the at least one initial physiological parameter to determine a target value of one or more energy substrate utilization variables that at least one of maintains and alters the body weight of the subject. The one or more energy substrate utilization variables comprise at least one of the macronutrient composition and caloric value of food consumed by the subject and the intensity and duration of activity by the subject.

In an embodiment, the at least one initial physiological parameter further includes at least one of height, age, gender, body mass index (BMI), body fat percentage, waist circumference, hip circumference, and chest circumference.

In an embodiment, the nonlinear feedback model is optimized further based on a quality and duration of sleep by the subject.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Other systems, processes, and features will become apparent to those skilled in the art upon examination of the following drawings and detailed description. It is intended that all such additional systems, processes, and features be included within this description, be within the scope of the present invention, and be protected by the accompanying claims.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 17A-17G are perspective views of components of the RQ device in FIG. 6 in accordance with some embodiments.

DETAILED DESCRIPTION

Figure 1:
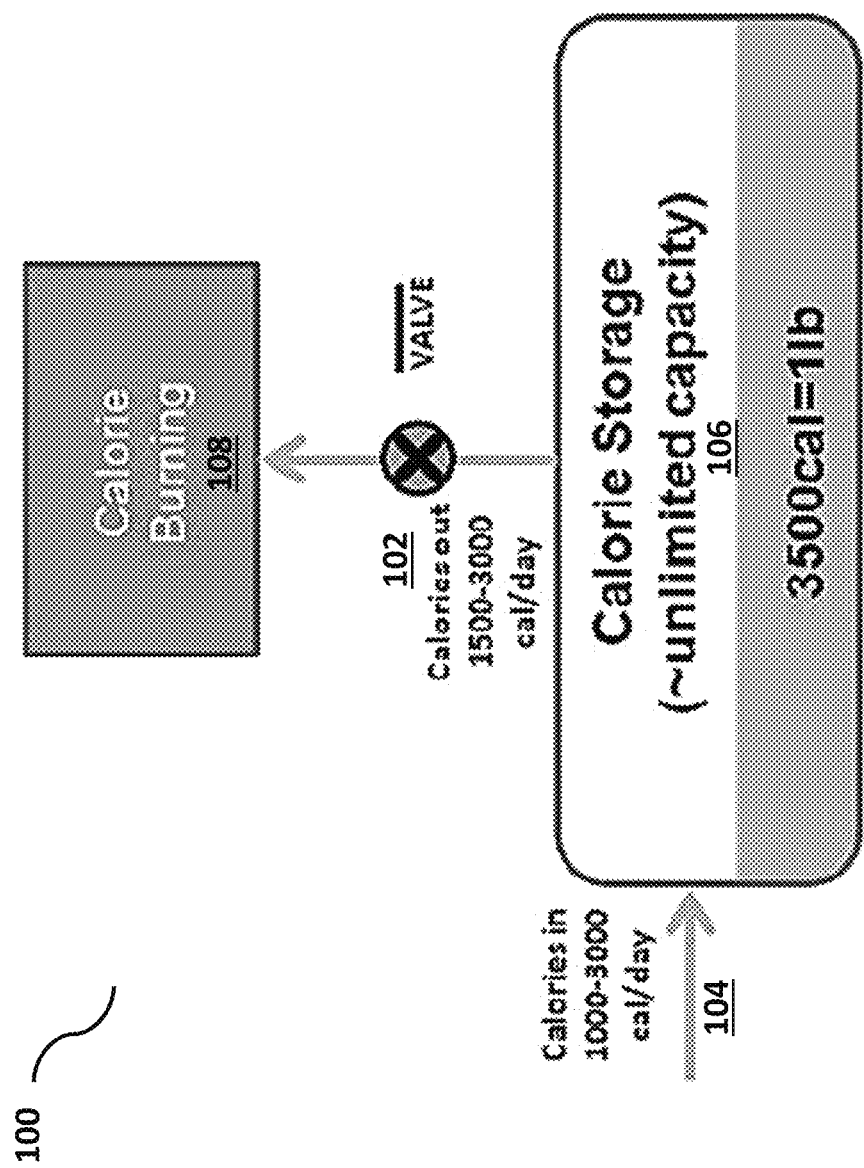
FIG. 1 is a diagram illustrating the "calorie-in/calorie-out" (CICO) model of metabolism.

The number of people afflicted by obesity, diabetes and other metabolic disorders has grown dramatically and alarmingly in the past decades, representing a major cost to society and adversely affecting the quality of life of many. The present application describes a system model for human metabolism developed to gain insight into the relationship between these metabolic disorders, their underlying causes, and to quantify the relationship between metabolic health and food. Furthermore, systems, apparatus, and methods related to modeling, monitoring, and/or managing a metabolic state of a subject are disclosed in the present application.

Existing metabolic models like the "calorie-in/calorie-out" (CICO) model fail to capture the physiological complexity of metabolism and therefore do not provide sufficient guidance to reverse obesity trends in individuals or populations. Thus, a new metabolic state model is provided for avoiding elevated blood glucose levels through proper selection of dietary macronutrients and exercise sufficient to enable the body's homeostatic system to achieve and maintain a healthy body weight. According to some embodiments, a personal respiratory quotient (RQ) measurement device and/or method is described for providing on-demand feedback indicative of a subject's real-time metabolic state and/or guiding the subject's macronutrient intake and/or activity levels to promote a desired metabolic state and/or achieve and maintain a healthy body weight.

"Calorie-in/Calorie-Out" (CICO) Models

The use of calorie counting as a means to promote and maintain weight loss has gained popularity over the past several decades. While the core concepts driving the CICO model are based on the conservation of energy principle, many individuals who have followed a diet plan that is based on the CICO model have met with failure to achieve and/or maintain their weight goals. The CICO model does not provide any insight into the metabolic complexity associated with consumption of food and conversion into useful metabolic energy or stored energy.

Specifically, the CICO model does not make a distinction regarding the macronutrient make-up of the food calories or the homeostatic mechanisms that incite hunger or satiety in response to food and activity levels. For example, both one liter of soda and a salad provide about 450 kilocalories, but a body's response to these two foods is different in terms of how the calories are processed, how quickly the calories become available to meet energy needs, how much of a sense of satiety the calories promote, and how much the calories perturb the blood glucose levels from nominal.

Moreover, recent studies indicate that the CICO model cannot explain the prevalence of increased adiposity despite reduced energy intake (see Mozaffarian et al., *NEJM*, 364 (25): 2392-2404 (2011); Ludwig et al., *JAMA*, 311(21): 2167-2168 (2014)). For example, one longitudinal study that included more than 120,000 subjects found that the kinds of food consumed affected the study participant's weight gain over a span of four years (id.). Another study proposed that diets that focus solely on calorie intake, and specifically those that focus on the restriction of calories consumed, may increase underlying metabolic dysfunction and, as a result, increase hunger (id.).

While adherence to a calorie restricted diet can be effective in producing weight loss, there are numerous reasons why calorie restriction usually fails to achieve and/or maintain long-term weight loss goals, including the following:

1) tracking food calories is time consuming and tedious and consequently may be prone to error;
2) restricting food calories without regard to macronutrient content can lead to nutritional imbalances that trigger hormones and neural responses that result in overconsumption and/or an inability to adhere to the calorie-restricted regimen;
3) genetic differences may affect a subject's basal metabolic rates as well as a subject's response to exercise and/or macronutrients, thus rendering formulaic prescriptive diets to be, at best, approximations;
4) metabolic needs of a subject change with weight loss and associated changes in the ratio of lean muscle mass to adipose tissue, thereby requiring an individualized adaptive calorie restriction formula to achieve a constant rate of weight loss or maintenance of a reduced body weight; and
5) a scale—the most common method for tracking weight loss—is effective in revealing long-term body weight trends but has a high variance from measurement to measurement due to varying states of the subject including, but not limited to, levels of hydration, glycogen stores, and contents of the stomach, intestines, and colon.

Aspects of an Optimized Metabolic State Model

According to some embodiments, a system model is premised on the observation that the body places a very high priority on maintaining blood glucose levels in a narrow range. For an average size individual, normal blood sugar levels, on the order of 100 mg/dl, translate to a control objective of no more than 5 g of glucose circulating in the body's entire blood volume. The fact that this level stays fairly constant, regardless of whether food is plentiful (hundreds of grams of glucose coming in to the bloodstream per day) or non-existent, is evidence that the body places a high priority on maintaining normal blood glucose levels employing mechanisms to monitor blood sugar levels, methods to signal that it is out of range, and means of actively controlling and correcting blood glucose levels in response to these signals.

At the cellular level, these processing can be quite complex, however, even with no knowledge of the detailed metabolic pathways and processes that enable these high level functions, the engineering discipline of control systems theory may be applied to develop a high-level system model that captures the dynamic behavior of metabolic systems in response to food and levels of physical activity. By definition, a system model is designed to "hide" underlying complexity which is accomplished by incorporating only the essential functions necessary to predict the system behavior for the situations of interest. According to some embodiments, a control system model enables assessment of the body's ability to successfully control blood glucose, but more importantly, it also enables predictions of limitations of this control, and identification of situations in which the system is unable to successfully maintain control.

Body weight is another quantity that the body seems to have the ability to tightly control under some conditions, as evidenced by the fact that many people maintain nearly constant body weight over long periods of time without having to consciously count and balance their calories consumed and their calories expended. Rather than focusing on blood glucose, a system model may be developed that describes the control of body weight in response to foods and exercise. However, body weight control may be a lower priority than blood glucose control and, as such, metabolic behavior is largely explained by the priority of blood glucose control. In fact, a principal mechanism the body employs to control blood sugar is to suspend any constraint on body weight as a means of achieving tight control of blood glucose.

The present application develops the control system approach for modeling metabolism from a notional construct to an executable numerical model.

Figure 2:
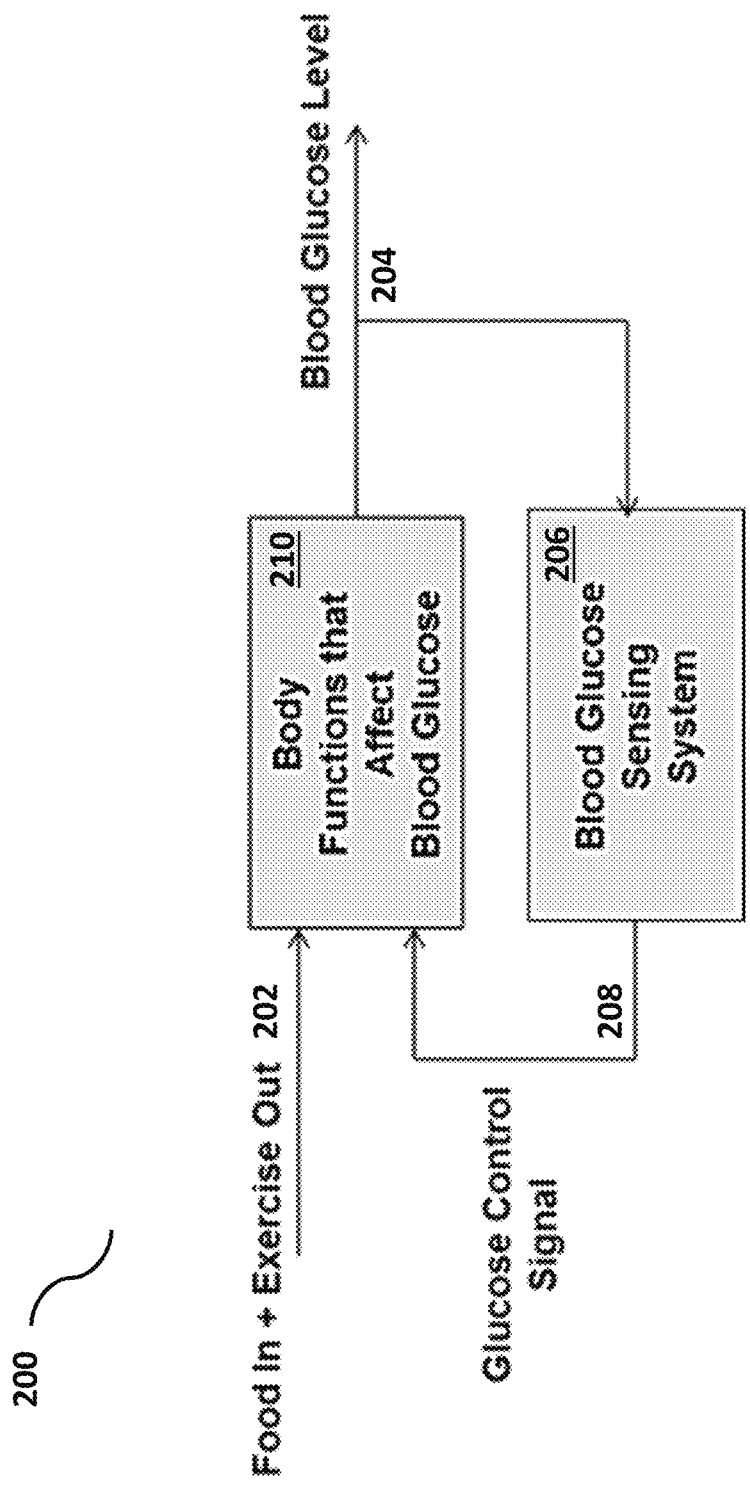
FIG. 2 is a diagram illustrating a blood glucose control model in accordance with some embodiments.

The body's demonstrated ability to tightly control blood sugar implies that the process is well suited to analysis and modeling techniques developed for feedback control systems. FIG. 2 is a diagram illustrating a blood glucose control model 200 that considers the inputs of food into the body and exercise by the body 202, the sensing of blood glucose level 204 by a blood glucose sensing system 206, which generates a glucose control signal 208, and a set of metabolic control functions 210 that respond to the control signal and further inputs in accordance with some embodiments. As illustrated in FIG. 2, in a feedback control system, the value of the output parameter that is being controlled, in this case blood glucose level 204, is measured and fed back into the controller, along with other external inputs, and the controller continuously adjust parameters in the system to achieve the desired output.

Food and activity level represent the body's metabolic interface to the outside world. Food intake, along with existing energy stores, provides the fuel needed to sustain metabolic processes. As much as 70% of the metabolic energy required over the course of a day is devoted to sustaining autonomic processes such as breathing, circulating blood, digestion. In addition to these internal processes, individuals also require energy to move about and perform daily activities.

The foods can place tremendous demands on the blood sugar control system, since an influx of food may release large amounts of glucose into the bloodstream. In contrast, intense exercise may deplete large quantities of blood glucose, which must be replenished quickly to sustain critical processes such as brain function. In either case, in the context of a blood glucose control model, the key parameter associated with food intake and activity level, is the rate at which glucose calories appear or are depleted from the blood stream.

Nutrients can have a direct effect on the flow of glucose into the blood stream. The three main macronutrients (fat, carbohydrates, and proteins) each have different effects on the dynamics of glucose level in the blood. Fat is neutral to the rate of appearance of glucose, since digestion of fat does not result in any glucose being produced. In contrast, the calories absorbed from carbohydrates are all destined to be released into circulation in the form of glucose. The rate of glucose appearance in the blood depends heavily on the timing of consumption, the quantity of carbohydrates consumed, and the glycemic index (a measure the speed with which food is turned into circulating glucose) associated with the particular carbohydrate. Protein can also affect blood sugar, since it can be converted into glucose through the process of gluconeogenesis.

For typical modern diets, the glucose load into the bloodstream is largely driven by digestion of carbohydrates. For example, drinking a sugary beverage might deliver 50 grams of glucose into the bloodstream at rates as high as about 6-7 grams/minute. If this were not compensated for in some way (see actuators below), blood sugar levels would rise to over 1000 mg/dl from this one drink. The fact that high glycemic index carbohydrates can release glucose into the blood stream quickly sets demand on the speed of response of the control system to mitigate the effect.

Understanding the timing, quantity, and intensity of physical activity, whether it is part of daily living or formal exercise is essential to correctly model the ability to control blood glucose levels. The demands that physical activity places on the blood glucose control system are directly related to the rate of depletion of glucose they induce. Low intensity exercise that burns fat will have negligible effects on glucose control; however, high intensity exercise utilizes glucose, and will have a direct effect on the level of glucose in the blood.

Exercise can use glucose at rates of over 1000 kcal/hour, which is on the order of 250 g of glucose per hour. Some of this fuel comes directly from glycogen stores but still has important impacts on the function of the control system.

During eating or exercise, the blood glucose sensing function of the body will detect changes in the glucose level and will respond by signaling the body to act in a way to offset this change. Understanding the details of how insulin and its counterpart, glucagon, broadcast their control signals to the body is not essential to correctly modeling the functional behavior of the control loop. It is sufficient to know that subsystems in the body respond to increasing and decreasing blood glucose levels by increasing and decreasing the level of the insulin and glucagon control signals.

Adopting control system terminology, in accordance with some embodiments, the mechanisms by which the body responds to the glucose control signals may be referred to as "actuators." According to some embodiments, four mechanisms may impact the quantity of glucose in circulation. In each of these functions, it is important to consider how much capacity they have to offset the rates of appearance and disappearance of glucose in the bloodstream. These capacity limits represent a nonlinear element of the control system and the effect of the nonlinearity is to produce complex dynamic responses despite a relatively small number of functional elements in the overall system. These nonlinear effects are critical to the understanding of type 2 diabetes and obesity. TABLE 1 below summarizes the four mechanisms, assesses the rate of glucose control that they can achieve, and catalogs the limit (capacity) of their control authority. For each of these four actuators, it is noteworthy that there is a direct connection between the presence of insulin and the rise in the level of the actuation, though this confirmation of insulin's integral role in affecting glucose control is not required for this model to be valid.

TABLE 1

| Control Mechanism | Actuation Method | Glucose Control Rate | Capacity Limit | Known Response To Insulin |
|---|---|---|---|---|
| Increase Metabolic Rate | Burn Glucose to lower level | Moderate (50 g/hr) | Max metabolic rate (50 g/hr) | Yes |
| Store Glucose as Glycogen | Move glucose out of blood | Very high (250 g/hr) | Glycogen stores (~400 g total) | Yes |
| Reduce Fat Burning | Increase glucose burning for fuel | High (150 g/hr) | 0% fat use (50 g/hr) | Yes |
| Convert Glucose to Fat | Remove glucose by conversion | Moderate (30 g/hr) | DNL rate in Liver (30 g/hr) | Yes |

"DNL" is used in TABLE 1 and throughout the present application as an acronym for de novo lipogenesis, which is described further herein.

The exact behavior of each of these mechanisms, as well as their capacity limitations, will vary across individuals and may also change with time for a given individual and are also a function of the recent history of food intake and exercise.

In response to a signal that blood sugar is high, the body can react by increasing the basal metabolic rate to consume more glucose from the bloodstream. Even when an individual is not intentionally physically active, they are still burning many calories for basal functions, as much as 70% of the total calories per day. These calories will draw from the fuel available in the bloodstream, and will serve to reduce the level of glucose in the blood. If, in response to the control signal, the metabolic rate increases, the rate of glucose consumption will increase producing the desired effect in response to the control signal. The increase in metabolic energy level may be achieved through a combination of increased temperature, body motion, or other metabolic function. For the purposes of the model, it does not matter what explains the increase in rate only that it occurs and is subject to rate and capacity limits. The metabolic rate cannot be arbitrarily increased in response to the signal, so its control authority to remove glucose is limited to on the order of 50 g/hour (basal rates of ~2500 kCal/day).

The body has the ability to respond to the control signal by storing glucose in a place other than the bloodstream. The body stores glucose in the form of glycogen in the liver and in skeletal muscle distributed throughout the body. While the exact behavior of the two storage forms are different, from the perspective a control system model, moving glucose in and out of storage represents a powerful tool for managing the rates of glucose appearance and disappearance in the blood. It has the capability to act very quickly (perhaps 250 g/hour), though the total storage capacity is typically about 400 grams. Once the storage becomes full, it can no longer sink excess glucose at any rate. Likewise, if glycogen stores are empty, they cannot be the source of glucose to compensate for declining blood glucose levels.

The body can meet its metabolic fuel needs by using any available nutrients. When using fat as a nutrient, it has no effect on blood glucose level. When using glucose, it directly depletes the glucose level in the blood. Therefore, shifting the fuel mix towards glucose is another control mechanism the body can use to respond to the control signal indication of elevated blood glucose. By adjusting the fuel mix, the body can quickly make large swings in the rate of glucose disappearing. Of course, it cannot drive the mix beyond the extremes of 0% or 100%, which represent a hard limit on the employment of this actuator and in fact since the brain/blood barrier prevents fat from entering the brain, some amount of glucose is necessary to sustain brain function and explains in part why blood glucose control is a priority.

The body modulates the level of fat burning by converting fats from free fatty acids (which can be used as fuel) to triglycerides (which cannot). Understanding this specific mechanism is not necessary to implement the control model.

Finally, the body has the capacity to convert glucose into fat, a process known as de novo lipogenesis. This process removes glucose from the blood thereby lowering blood glucose. There is some debate as to what rate de novo lipogenesis can occur at, and under what conditions it occurs. It appears to activate as a last resort to blood glucose control when the control authority of the three other mechanisms described above become saturated.

According to some embodiments, a metabolic state model is optimized based on avoiding elevated blood glucose levels through proper selection of dietary macronutrients and exercise sufficient to enable the body's homeostatic system to achieve and maintain a healthy body weight.

Figure 3:
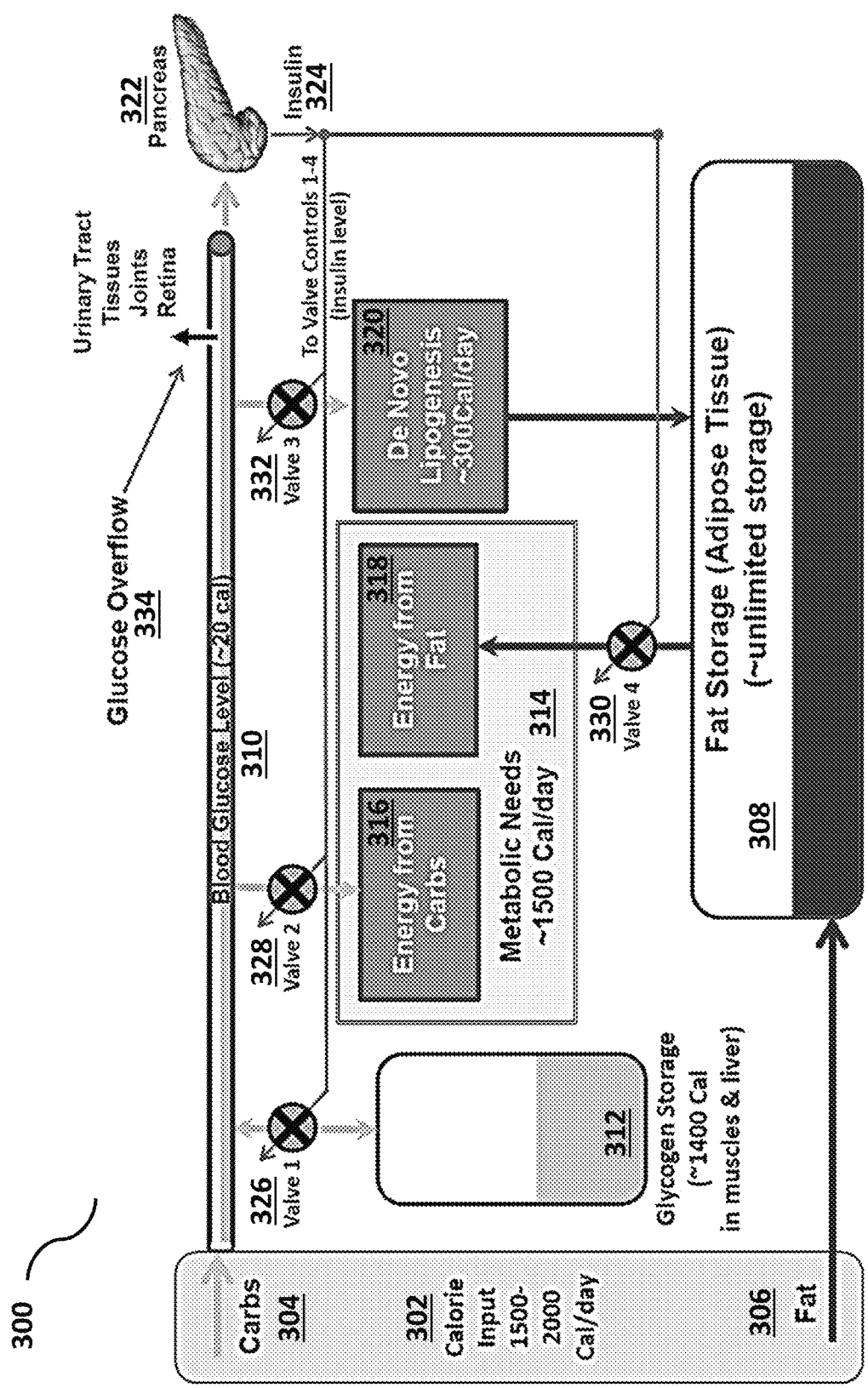
FIG. 3 is a control block diagram illustrating the body's blood glucose control system in accordance with some embodiments.

These inputs, the sensing function, control signal, and the actuators described above may be combined in a way that shows their connectivity and allows explanation of their interactive function. FIG. 3 is a control block diagram illustrating the body's blood glucose control system in accordance with some embodiments. In FIG. 3, food calories 302 from carbohydrates 304 and fats 306 are input into the model. Carbohydrates 304, in the form of glucose, in the circulation are depicted flowing from left to right, and dietary fat 306 is depicted as flowing from left to right into fat storage or adipose tissue 308. For fat, model 300 is extremely simple. Since the body has essentially unlimited capacity to store fat, the disposition of dietary fat can be modeled by initially placing all consumed fat into this vast storage reservoir. According to some embodiments, the fat storage may be treated as unlimited and/or the fat storage may be allowed to contribute to metabolic needs. For dietary carbohydrates, storage options are limited, and carbohydrates are depicted flowing directly into the bloodstream, at a rate determined by the glycemic index, raising the blood glucose level 310. Excess carbohydrates in the circulation may be temporarily stored as glycogen 312 in the liver and the skeletal muscles. Excess carbohydrates in the circulation also may be used to fulfill metabolic needs 314. For example, metabolic needs may be met with energy from carbohydrates 316 and/or energy from fat 318. Further excess carbohydrates in the circulation may result in de novo lipogenesis 320.

According to some embodiments, the metabolic state model acts to maintain a constant blood glucose level 310. For example, a healthy adult human regulates blood glucose levels within a narrow band of between about 80 to 110 mg/dl×50 dl (i.e., about 5 g or about 20 calories). This blood glucose level is roughly constant whether food is plentiful or scarce. If carbohydrates are not temporarily stored as glycogen 312, used for metabolic needs 314, or converted into fat 320, β-cells in the pancreas 322 will produce the hormone insulin 324 to help control blood glucose.

According to some embodiments, the metabolic state model identifies the critical metabolic state control loops or actuators, depicted in FIG. 3 as independent valves 326, 328, 330, and 332. The master regulator for each valve is insulin. The pancreas 322 monitors the level of circulating glucose 310, and emits insulin 324 as a control signal to four actuators for lowering blood glucose. Each of the actuators is shown in the figure as a valve that responds to the control signal. The glycogen storage valve 326 shuttles glucose into the limited stores of glycogen 312, the metabolism valve 328 controls the metabolic rate 314, the fat burning valve 330 turns off to maximize the use of glucose, and the lipogenesis valve 332 ramps up de novo lipogenesis 320.

According to some embodiments, these metabolic state control mechanisms include:

a) burning more glucose for energy through intentional increase in activity (e.g., exercise) or unintentional homeostatically-induced responses (e.g., fidgeting);
b) storing more glucose as glycogen in the liver and skeletal muscles (facilitated by depleting glycogen storage, e.g., through exercise);
c) blocking the use of dietary fat as an energy source (i.e., store the dietary fat instead so that metabolic needs require more glucose); and
d) converting more glucose into fat (i.e., de novo lipogenesis).

According to some embodiments, any or all of these responses may be rate and capacity limited. These rates and capacities may be adjusted depending on factors including, but not limited to, the species, gender, age, and genetic factors associated with each individual subject. In some embodiments, metabolic needs are capped at, for example, about 1500 calories per day depending on the individual subject. The glycogen storage capacity in an adult human is approximately 15 g/kg of body weight. Thus, in some embodiments, glycogen storage is capped at, for example, about 1400 calories depending on the individual subject. In some embodiments, de novo lipogenesis is capped at, for example, about 300 calories per day depending on the individual subject.

Also shown in this model is the notion of glucose overflow 334. When blood glucose exceeds a subject's homeostatic mechanisms by reaching a level at which the excess glucose cannot be disposed of through a combination of combustion, conversion or storage, then other mechanisms manifest themselves in response. The glucose will overflow into the surrounding tissues (e.g., accumulating in tissues, joints, retinas, etc.) and the kidneys will pass glucose into urine, which is characteristic of type 2 diabetes. These are not considered as actuation methods above, since they represent disease conditions.

In some embodiments, the metabolic state model provides insights into and feedback regarding the relationship between chronically elevated blood glucose levels and obesity.

Diabetes is defined as the impaired ability to control blood glucose, so this model has direct applicability to understanding its behavior. For type 1 diabetes, the impairment is in the sensing system. Despite the elevation of blood glucose, no signal, or a very weak one, is produced to signal the actuation mechanisms. Whether the missing signal is caused by an inability to sense glucose in the blood or an inability to produce insulin to broadcast the message, the actuators are never enabled despite having ample capacity to control blood sugar. When insulin is manually added to the blood stream, the full set of actuation mechanisms will properly function to control blood glucose levels, though maintaining the precise level of insulin required to balance incoming glucose with the setting of the actuators is very difficult to achieve without constant monitoring of the blood glucose level. This model may be employed to better understand the dynamics of the insulin control system, in much the same way as an artificial pancreas might function.

In some embodiments, this model is also particularly useful in providing insights into type 2 diabetes. In this disease state, the body is also unable to control blood glucose levels; however, it is not due to a malfunction of the sensing portion of the control system. Typical insulin levels with type 2 diabetes are much higher than normal, yet the blood glucose control system does not adequately respond to the sensor signal. The condition is referred to as insulin resistance, suggesting that the actuation mechanisms need higher signal levels than previously required to reach the proper control level. However, there is not a clear understanding or consensus regarding the root cause of this apparent loss in insulin sensitivity.

In some embodiments, this model may offer an alternative explanation of the precursors and root cause of type 2 diabetes. If all of the four actuation mechanisms described above are functioning at their full capacity, then the presence of higher levels of insulin will have minimal effect on the rate at which glucose is cleared from the blood, and all of the symptoms of type 2 diabetes will be present, despite high levels of insulin. Blood glucose control will fail if the control authority available in the actuators is less than the rate of glucose appearance in the blood stream. This interpretation of type 2 diabetes implicates the macronutrient content we ingest as the root cause diabetes symptoms. Any individual whose actuation mechanisms cannot keep up with the rate that carbohydrates are being absorbed will exhibit diabetes symptoms. Changes to diet that add carbohydrates and that move toward high glycemic index foods will challenge the available control authority of a greater fraction of our population. This explanation of type 2 diabetes does not require postulating or explaining the origins and mechanism of insulin resistance. Conversely, the model suggests that if carbohydrate rates of appearance are reduced to be compatible with the individual's control authority to process carbohydrates, then the symptoms of type 2 diabetes may quickly disappear.

The genesis of the metabolic model was to functionally model the mechanisms involved in responding to changes in blood glucose. However, the insight the model provides may extend beyond understanding just the control of blood glucose, by quantifying how the blood glucose control settings affect body weight.

Contrary to the view that obesity is the cause of insulin resistance and the onset of type 2 diabetes, this model suggests an alternative sequence of events according to some embodiments. For example, the model predicts that when the body is struggling to reduce high blood glucose levels, it will shut off the burning of fat and in some situations convert excess glucose into fat in an attempt to keep up with the rate of glucose input. If, as a result of dietary habits, an individual is constantly releasing high levels of glucose into the blood stream, the response of these control mechanisms will manifest as an increase in stored fat. Consequently, for an overweight individual seeking to reduce body weight through a low fat (hence high carbohydrate) diet, the metabolic settings the body is choosing in an effort to control glucose prevent the fat burning needed to reduce body weight.

In some embodiments, the model may be used to predict an individual's response to a given diet and how the response varies with number of calories, macronutrient mix, glycemic index, duration of exercise, and/or intensity of exercise. Tuned to an individual, the model may be used to determine what dietary intake and nutrient mix will ensure that blood glucose control does not override the body's signals related to weight control, enabling the individual to burn dietary and stored fat, rather than carbohydrates, to meet metabolic energy needs.

In some embodiments, described further herein, a fully numerical simulation of the control system of FIG. 3 may be used to produce quantitative assessments of how diet and exercise affect diabetes and obesity. In further embodiments, also described further herein, an apparatus comprising a metabolic sensor may enable an individual to easily customize this model to their own metabolic limits and behavior, as well as obtain on-demand feedback on how hard the body is working to keep blood glucose in the normal range.

The metabolic state of a body (e.g., a fat burning or a de novo lipogenesis state) can be accurately tracked by measurement of the respiratory exchange ratio (RER). As used herein in the specification and in the claims, RER is interchangeable with respiratory quotient (RQ). Both RER and RQ are measurements of the ratio of carbon dioxide ($CO_2$) production and oxygen ($O_2$) consumption.

Figure 4:
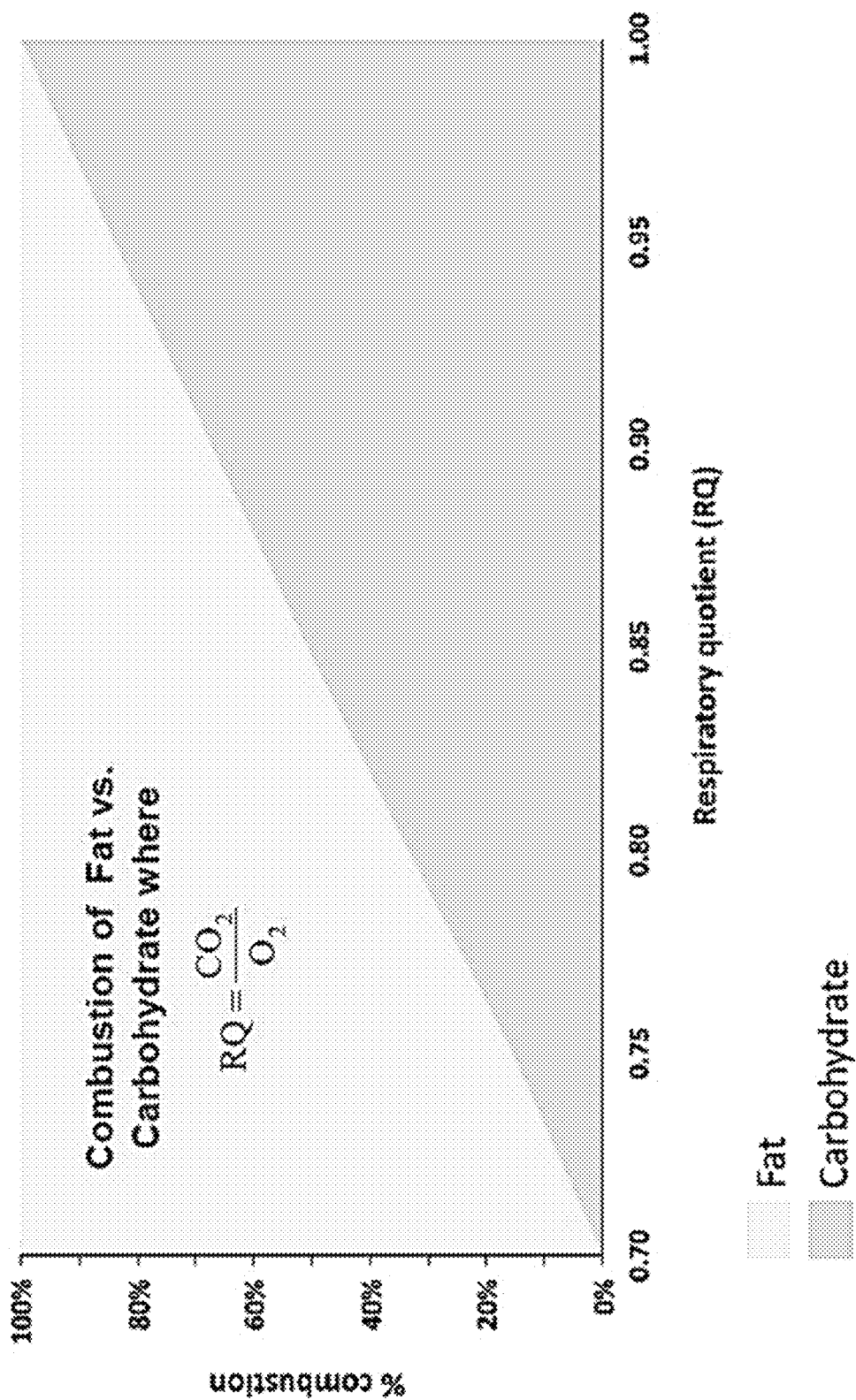
FIG. 4 is a graph illustrating the relationship between respiratory quotient (RQ) values and the combustion of fats and carbohydrates in accordance with some embodiments.

FIG. 4 is a graph illustrating the relationship between respiratory quotient (RQ) values and the combustion of fats and carbohydrates in accordance with some embodiments. RQ measurements may inform whether a subject is primarily in a carbohydrate-burning state (RQ≅1.0), in a mixture of carbohydrate and fat-burning state (e.g., RQ≈0.85), or primarily in a fat-burning state (RQ≅0.7). Note that RQ values between 1.0 and 0.7 represent a mixture of fat, carbohydrate, and protein burning states. During rest and low activity levels, RQ values in excess of 1.0 indicate that a subject is turning carbohydrates into fat (i.e., de novo lipogenesis state).

Figure 5:
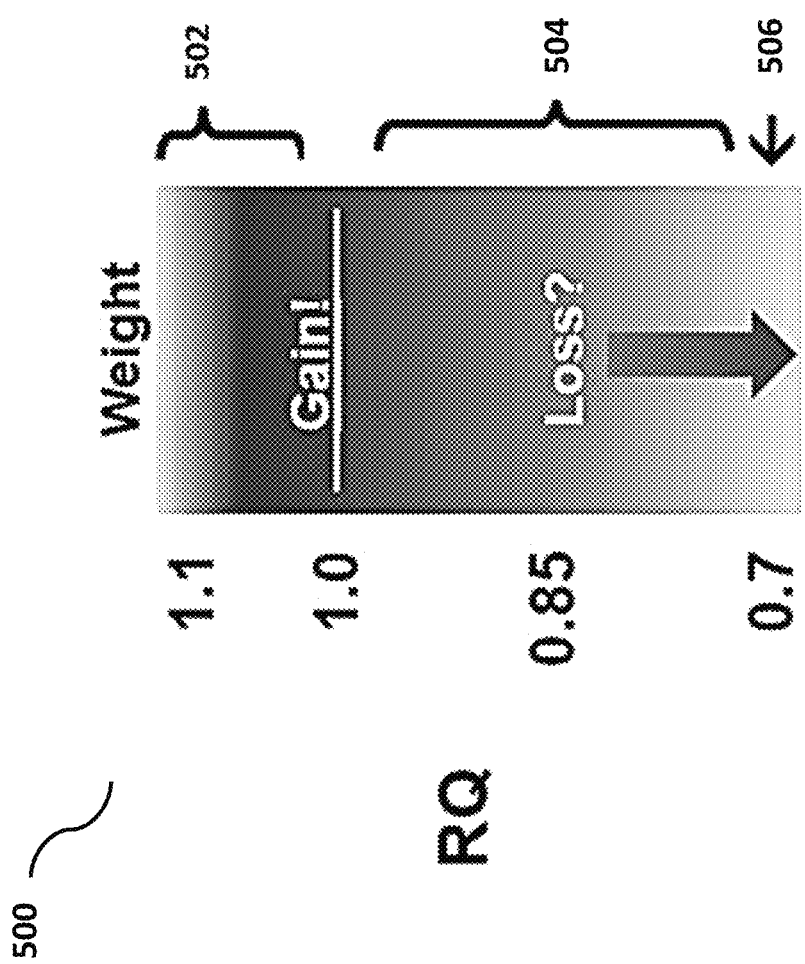
FIG. 5 is a diagram illustrating the relationship between RQ values and weight gain/loss in accordance with some embodiments.

FIG. 5 is a diagram 500 illustrating the relationship between RQ values and weight gain/loss in accordance with some embodiments. RQ measurements may inform whether a subject is in a state that contributes to weight gain 502 (RQ≥1.0), maintains weight 504 (e.g., RQ matched to the food quotient, nominally 0.85), or contributes to weight loss 506, with RQ near the low end of the scale (RQ≅0.7) indicating a high percentage of metabolic energy derived from fat.

RQ is a measurement of the ratio of the volume of carbon dioxide produced per unit time to the volume of oxygen consumed per unit time and may be calculated using equation (1) below:

$$RQ = \frac{VCO_2}{VO_2} \quad (1)$$

RQ can be used to represent when a subject is in a carbohydrate burning state or in a fat burning state. For example, the carbohydrate burning state may be represented as chemical equation (2) below, which yields the RQ value of 1.0 according to equation (3) below:

$$C_6H_{12}O_6 + 6O_2 \rightarrow 6CO_2 + 6H_2O \quad (2)$$

$$RQ = \frac{VCO_2}{VO_2} = \frac{6}{6} = 1.0 \quad (3)$$

The fat burning state may be represented as chemical equation (4) below, which yields the RQ value of 0.7 according to equation (5) below:

$$C_{18}H_{36}O_2 + O_2 \rightarrow 18CO_2 + 18H_2O \quad (4)$$

$$RQ = \frac{VCO_2}{VO_2} = \frac{18}{27} = 0.7 \quad (5)$$

According to some embodiments, the incorporation of RQ measurements in a metabolic state model provides advantages over food calorie tracking and restriction by directly assessing the precise metabolic state of a subject on demand. Unlike calorie-based weight management, coupled with body weight tracking, RQ provides immediate feedback to a subject as to whether or not diet and exercise activities, which may be modulated by genetic factors unique to each individual, are putting the subject in a homeostatic zone where body weight and glucose are both successfully controlled. Specifically, when a subject's glucose system has been overwhelmed for long periods of time (indicated by blocking of fat burning, and conversion of excess glucose into fat via de novo lipogenesis), the subject's body manifests these metabolic responses in the form of weight gain. RQ measurements may be used to avoid overconsumption of carbohydrates, enabling a subject to maintain normal blood glucose levels thereby allowing weight-related homeostasis mechanisms to properly function and, as a consequence, lose or maintain weight. In addition to weight control, RQ measurements also may be useful in early detection, prevention, and/or management of type 2 diabetes and/or other metabolic diseases. Additional uses of RQ measurements include, but are not limited to, supporting athletic training and assessing athletic endurance.

The invention will be further described in the following examples, which are not intended to limit the scope of the claims.

EXAMPLES

An Executable and Optimized Metabolic State Model

An executable state model optimized for metabolism is disclosed according to some embodiments.

Inputs into the executable metabolic state model may include, but are not limited to, one or more RQ values, a macronutrient composition and caloric value of food consumed by the subject (e.g., carbohydrates versus fats), an intensity and duration of activity by the subject (e.g., carbohydrate-burning activity versus fat-burning activity), a rate and maximum capacity of glycogen storage in the subject, a rate and maximum capacity of de novo lipogenesis in the subject, and/or a quality and duration of sleep by the subject. In some embodiments, an executable metabolic state model is run on an RQ device and/or communicatively coupled with an RQ device. Additional variables may include, but are not limited to, information associated with measures of blood glucose, glycogen, average carbohydrate intake, basal carbohydrate metabolism, body fat, average fat intake, basal fat metabolism, body weight, heart rate, respiration rate, average insulin level, and/or insulin level in the subject.

Outputs from the model may include, but are not limited to, raw measurement values and/or feedback in the form of suggested nutritional and/or exercise modifications or goals relating to weight management, disease management, and/or athletic training.

According to some embodiments, the numerical model reveals the time response behavior of metabolism to both food and activity levels and, consequently, enables investigation of the impact of dietary macronutrients and exercise on the selection of energy substrate and the control of body weight. An executable model may require quantifying how each of the four control methods described respond to the presence of the control signal (e.g., an "insulin" control signal, which takes on positive values in response to high blood glucose levels and negative values in response to low blood glucose levels, with the negative values representative of glucagon signaling), and how the magnitude of the response becomes saturated as it reaches its control limit. In some embodiments, a numerical description of how the insulin control signal itself is generated in response to changes in blood glucose level is developed.

Figure 6:
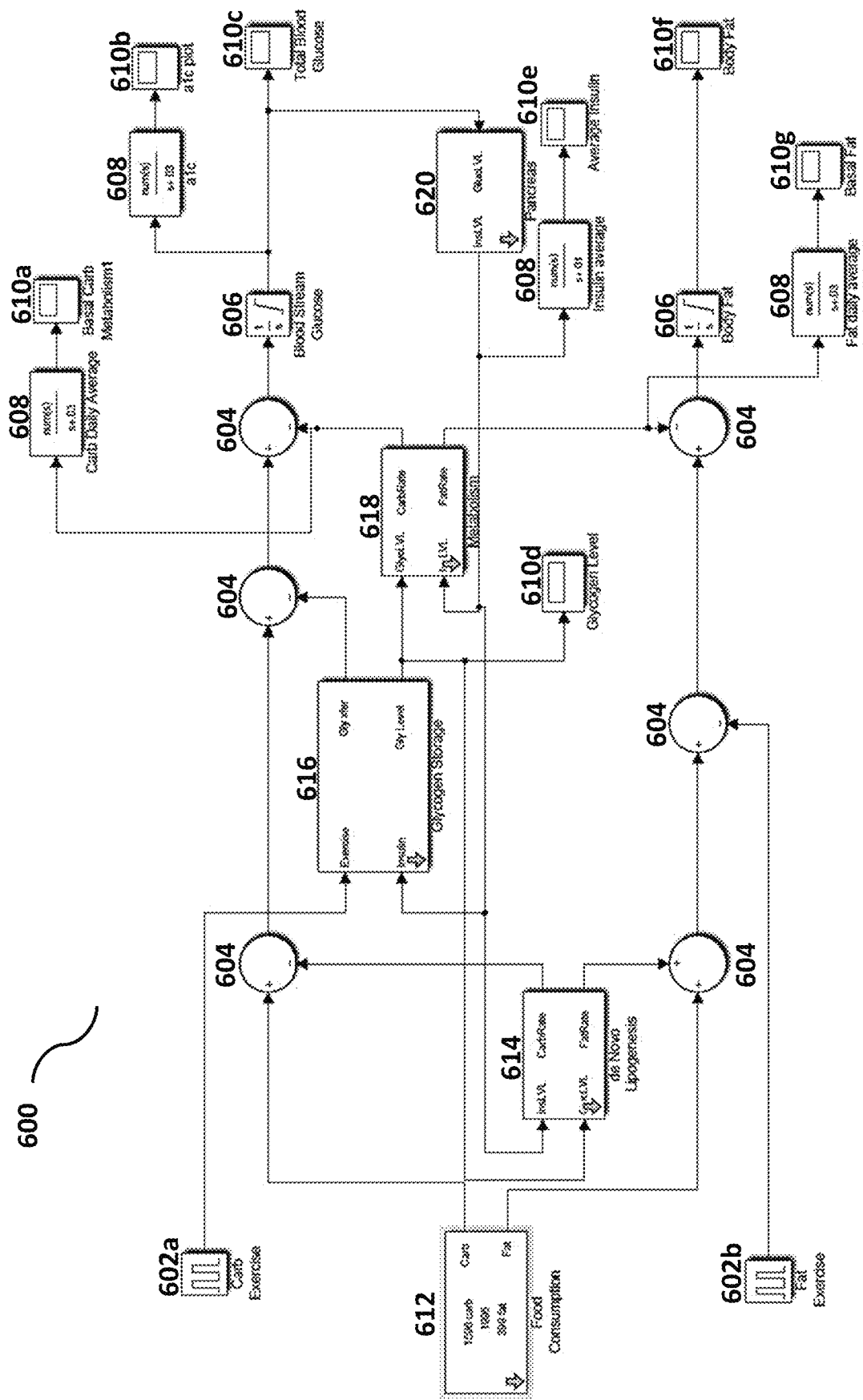
FIG. 6 is an overall block diagram for an executable baseline metabolic model illustrating the relationship between food consumption, insulin levels, body fat, blood glucose, etc., in accordance with some embodiments.

With simple descriptions of these component pieces, hardware and/or software tools, such as Simulink® (available from MathWorks®, Natick, Mass.), which is built on the idea of signal flow graphs, may be used to simulate the model behavior when all of these pieces interact. FIG. 6 is an overall block diagram 600 for a baseline metabolic model in accordance with some embodiments. The simulation allows for inputs of food and exercise, a model of each of the four mechanisms to process carbohydrates, fat stores behavior, an insulin secretion model, and monitors of key parameters.

Many variations and extensions to the baseline executable model of FIG. 6 are possible. For example, Simulink® includes an extensive library of functional blocks that may be specialized and interconnected to represent the information flow associated with the processes of interest. In FIG. 6, four functional block types are depicted in accordance with some embodiments. One functional block type is a pulse generator 602, which is used in the metabolic model to generate periodic feeding or exercise schedules. For example, pulse generator 602a represents carbohydrate burning exercise, and pulse generator 602b represents fat burning exercise. A second functional block type is a summing junction 604. A third functional block type is an integrator 606 with upper and lower saturation limits. A fourth functional block type is a first order transfer function 608, with time constant 1/a, which is used in the metabolic model to generate daily averages. Viewing scopes 610 are used in the metabolic model to plot time evolution of one or more user-selected parameters, including basal carbohydrate metabolism, basal fat metabolism, body fat, glycogen level, total blood glucose, and average insulin.

In FIG. 6, five modules are depicted in accordance with some embodiments. Each module may be a multi-input and/or multi-output user-defined subsystem, which further includes a number of interconnected functional blocks. Module 612 executes food consumption function(s), module 614 executes de novo lipogenesis function(s), module 616 executes glycogen storage function(s), module 618 executes metabolism function(s), and module 620 executes pancreas function(s). Each module is simply a means of grouping together functional blocks that together implement a common function. More or fewer modules, even no modules, may be used in accordance with some embodiments.

The food consumption module 612 as well as two exercise blocks 602a, 602b together provide the dietary intake and activity levels over the duration of the simulation in accordance with some embodiments. Within module 612, the time for each meal, calorie, and macronutrient composition is specified. The carbohydrate burning exercise block 602a is used to represent high intensity, carbohydrate burning activities, while the fat burning exercise block 602b is used to represent lower intensity, fat burning exercise, such as walking. The blocks may be employed together to represent any combination of fat plus carbohydrate burning exercise. Employing the pulse generators 602 to represent exercise allows the duration and frequency of the exercise to be specified as well as the phasing or time of day for the start of exercise. The exercise model can be made as complex and variable from day-to-day as desired, but in the example of FIG. 6, is modeled as a fixed duration at the same time each day.

The de novo lipogenesis module 614 in FIG. 6 implements de novo lipogenesis based on the insulin levels and available glycogen storage capacity in accordance with some embodiments. When the insulin levels are high, implying high blood glucose, and there is little or no remaining glycogen storage capacity available, de novo lipogenesis is initiated to begin converting circulating blood glucose to fat for storage. De novo lipogenesis fat is added to any dietary fat and the combined signal is reduced by any fat burning exercise and heightened metabolic rate before being added to the body fat stores, which can be viewed on the body fat viewing scope.

The dietary carbohydrates take a slightly more complicated path through the model in FIG. 6, passing through three summing junctions where the dietary intake can be reduced by de novo lipogenesis activity, glycogen storage, and metabolic rate, before passing through an integrator that tracks the blood glucose level, subsequently passing this signal to the pancreas module 620 where the insulin control signal is generated based on the blood glucose levels.

The glycogen storage module 616 controls the glycogen storage and retrieval process which is modeled as a whole-body effect, with no distinction between glycogen storage in liver versus muscle tissue. This distinction may be incorporated in the module if desired.

Figure 7:
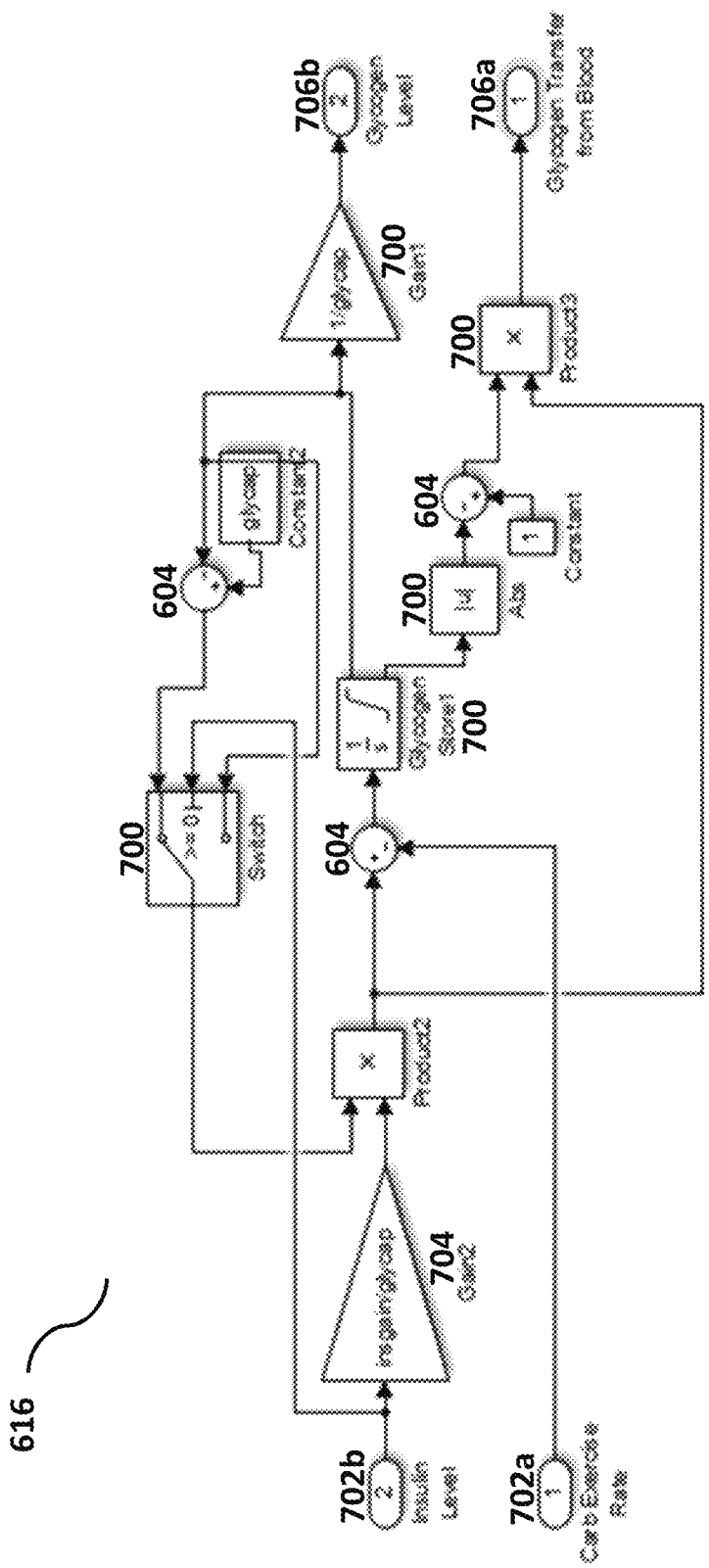
FIG. 7 is a block diagram of the internal composition of the glycogen storage module in FIG. 6 in accordance with some embodiments.

FIG. 7 is a block diagram of the internal composition of the glycogen storage module 616 in FIG. 6, which is described in detail to provide a representative example of the internal structure of a functional module according to some embodiments. In FIG. 7, some new functional block types are depicted, including a signal input port 702 for a user defined module, which is used in the glycogen storage module 616 to input carbohydrate exercise rate 702a and insulin level 702b. Another new functional block type is a gain block 704, which is used in the glycogen storage module 616 to multiply an incoming signal by a user-defined gain term K. Yet another new functional block type is a signal output port 706 for a user defined module, which is used in the glycogen storage module 616 to output glycogen transfer from blood 706a and glycogen level 706b.

If insulin level 702b is positive, insgain/glycap block 704 is scaled by the fraction of remaining glycogen storage capacity (i.e., (glycap-glylevel)/glycap), with the result that insulin impact on glycogen storage varies from a maximum of insgain, when glycogen stores are fully depleted, to zero, when glycogen storage is at capacity.

If insulin level 702b is negative (i.e., glucagon), insulin impact on glycogen retrieval varies from insgain to zero in proportion to glylevel/glycap. The function of these blocks comprising the glycogen storage module 616 and their ranges are summarized in TABLE 2 below.

TABLE 2

| Element | Units | Range | Default |
| --- | --- | --- | --- |
| Input: Insulin Level | — | Defined in insulin module | ±30 |
| Input: Carb Exercise Rate | Kcal/hr | Defined in carb exercise module | 0 |
| Gain2: insgain/glycap | $kcal^{-1}$ | Set in module mask parameters | 50/2300 |
| Switch: controlled by insulin polarity | kcal | ±insgain | — |
| Store1: Integrator Output | kcal | 0 to glycap | 0.5*glycap |
| Store1: Saturation indicator | — | 0 unsaturated, ±1 when saturated | — |
| Output: Glycogen Level fraction | — | 0 to 1 | 0.5 |
| Output: Glycogen Transfer | kcal/hr | insgain*(insulin level) | 50*30 |

Turning attention again to the overall metabolic model block diagram in FIG. 6, the metabolism module 618 monitors the glycogen storage level and the insulin level in order to adjust the fraction of metabolic energy derived from carbohydrates versus fats, with the ability to completely shut off fat as a source of energy and rely exclusively on carbohydrates (glucose). The metabolism module 618 may include a user-settable basal metabolic rate with diurnal variation and also as the capability to increase the basal metabolic rate over a user-specified range in response to high levels of insulin.

For anyone familiar with the cellular level processes for supplying metabolic energy demands, storing excess carbohydrates and fats and releasing the hormones necessary to control these processes, the elements comprising the block diagram in FIG. 6 may seem too sparse and/or simple to provide useful insight into these complex metabolic processes. However, while the model is simple by design, the output of the model can be quite complex and varied in response to dietary and exercise inputs. For example, the model may be shown to capture the salient metabolic responses identified in a comprehensively documented fourteen-day study of carbohydrate overfeeding with reasonable accuracy as described further herein.

The performance of the model and the function of the modules in FIG. 6 may be illustrated with a simple baseline reference case and modification of the food and exercise inputs.

For example, in a baseline case, the basal metabolic rate in the metabolism module 618 is set to 1800 kCal/day, with a diurnal variation of ±300 kcal, and the feeding schedule consists of breakfast, lunch, and dinner with no between-meal snacks. The macronutrient mix and calorie equivalent of the meals is shown below in TABLE 3.

TABLE 3

| Parameter | kcal | Carb % | $\tau_{FAT}$ (hrs) | $\tau_{GLY}$ (hrs) |
|---|---|---|---|---|
| Breakfast | 550 | 56 | 0.5 | 0.2 |
| Lunch | 500 | 56 | 0.5 | 0.2 |
| Dinner | 775 | 56 | 0.5 | 0.2 |
| Total or Average | 1825 | 56 | 0.5 | 0.2 |

Note that for this baseline example, daily dietary intake is just 25 kcal higher than the basal metabolic rate and all of the meals are comprised of 56% carbohydrates and 44% fats with the absorption time constants for the carbohydrates and fats, different from one another but constant over all meals. These parameters represent a nearly unrealizable uniformity for actual meals but serve to illustrate the salient features of the model. For simplicity and clarity of illustration, the meal schedule and composition is held fixed for each simulation day.

In the reference baseline, there is no exercise or physical activity scheduled other than the diurnal basal metabolic rate of 1800 kCal/day. The available fat stores at the beginning of the simulation are initialized to 25,000 kcal which, at a nominal 3500 kcal/lb corresponds to approximately 7 lb of adipose tissue. The glycogen storage capacity is initialized to 2300 kcal, the equivalent of 575 g of carbohydrate stored in the liver and muscles, with glycogen stores half full at the beginning of the simulation.

According to some embodiments, the metabolic model is run for a simulation time period of two weeks, or 336 hours, and completes execution in less than about one second. The seven view scope icons depicted in FIG. 6 represent viewers in which the parameter identified can be viewed. Additional scopes may be added to display and compare multiple parameters in one plot.

Figure 8A:
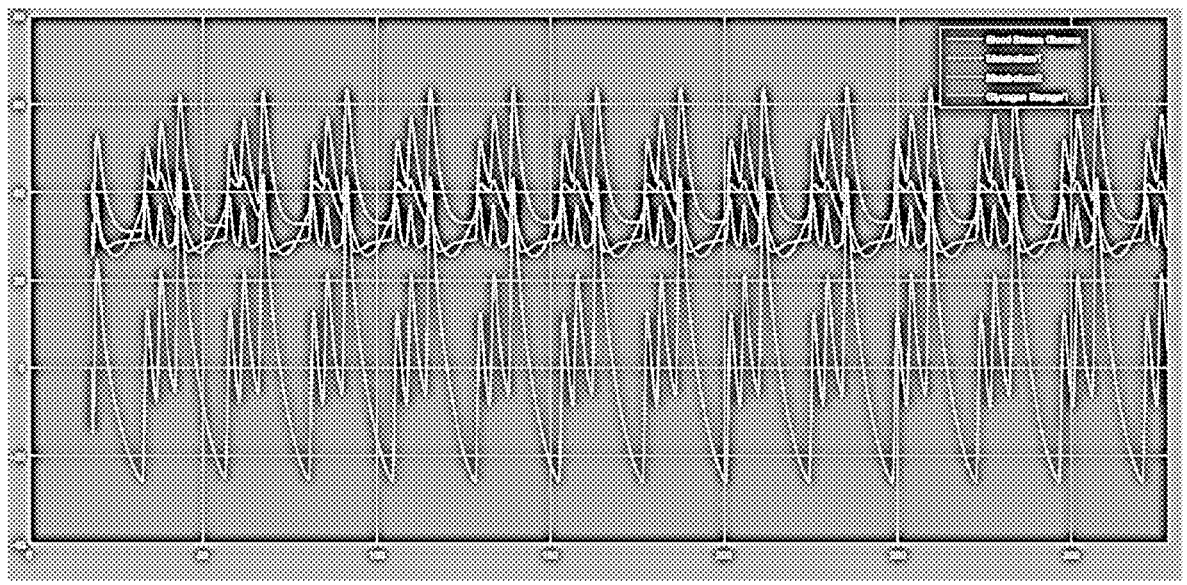
FIG. 8A is a plot illustrating metabolic energy sources and glycogen transfer for a baseline energy-balanced case in accordance with some embodiments.

FIG. 8A is a plot illustrating metabolic energy sources and glycogen transfer for the baseline energy-balanced case in accordance with some embodiments. In particular, FIG. 8A depicts the change in glycogen stores and the energy derived from carbs and fats in units of kcal/hr. The impact of the three meals is evident in the daily spikes in blood glucose and metabolic activity. There is also movement of carbohydrates in and out of glycogen storage although the amounts are small. Integration of the curves results in the daily averages shown in FIG. 8B.

Figure 8B:
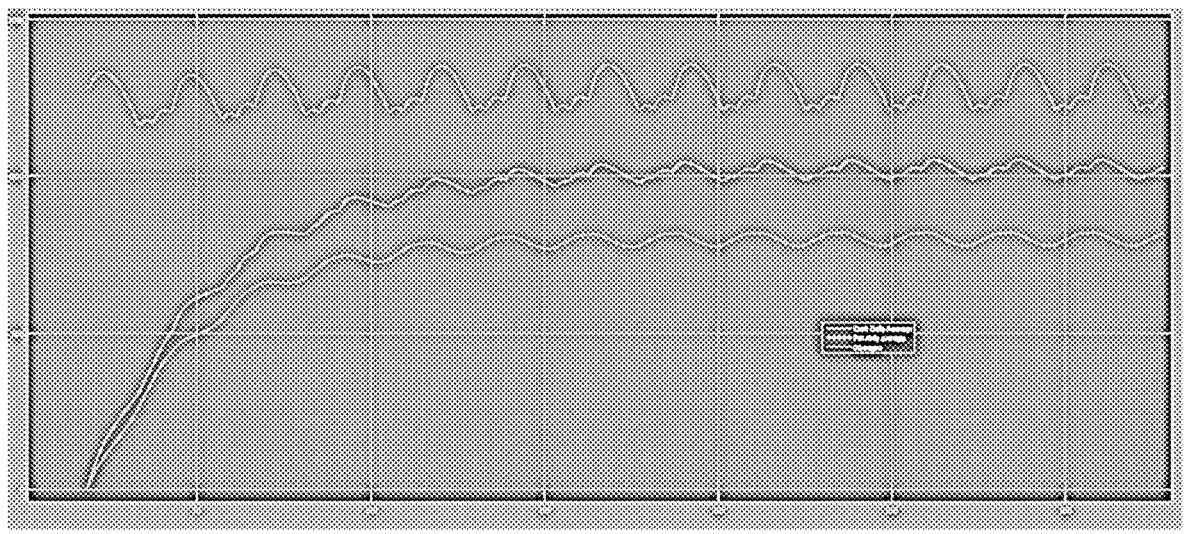
FIG. 8B is a plot illustrating daily energy substrate and glycogen stores in accordance with some embodiments.

FIG. 8B is a plot illustrating daily energy substrate and glycogen stores in accordance with some embodiments. In particular, FIG. 8B presents this information in the form of a daily average of carbohydrate and fat energy sources along with the glycogen storage all in kCal/day. After the initial transient associated with initializing the model, the average daily energy expenditure approaches a steady state matched to the dietary intake, with small transients related to the three daily meals, carbohydrates moving in and out of storage, and diurnal variation in the basal metabolic rate.

Figure 9:
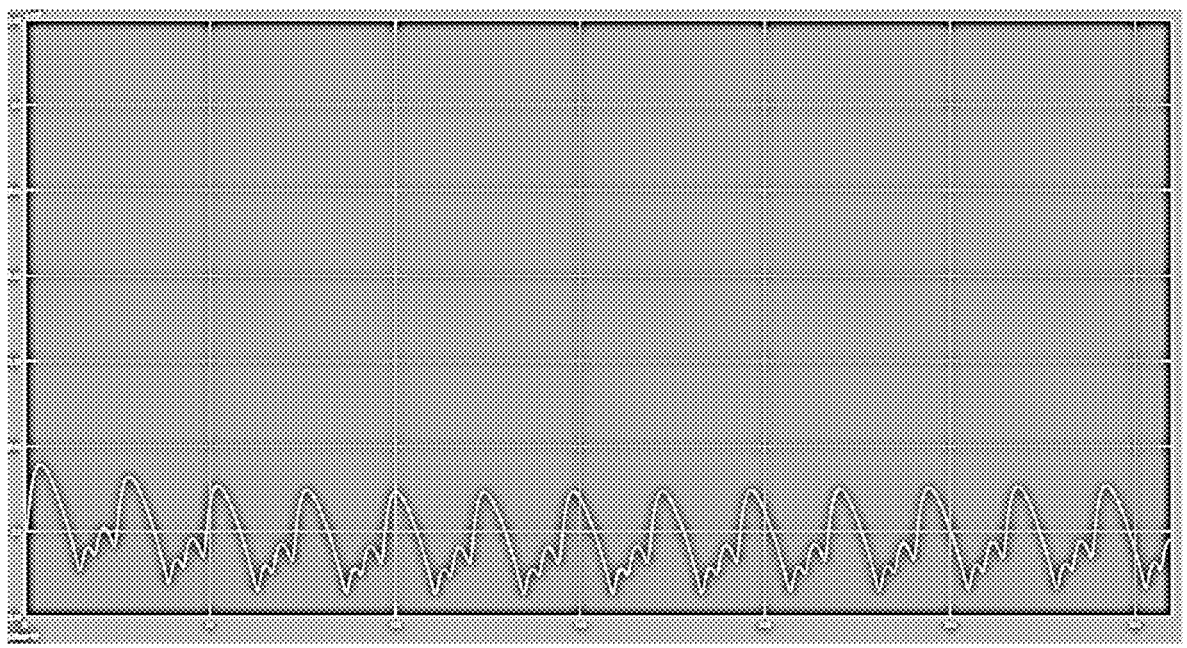
FIG. 9 is a plot illustrating stable adipose tissue stores for an energy-balanced state in accordance with some embodiments.

The implication is that there is an energy balance which, as FIG. 9 illustrates, results in a stable value of stored fat over the simulated two week time period. FIG. 9 is a plot illustrating stable adipose tissue stores for energy balanced state in accordance with some embodiments.

In the baseline case, the dietary intake is closely matched to the resting metabolic rate and the glycemic index of the diet is low, thereby minimizing blood glucose spikes and resulting in a stable weight and good control of blood glucose. In the next example, the impact on metabolism is assessed from simply increasing the glycemic index of the diet, from 0.2 to 0.6, without changing either the total dietary calories or macronutrient mix. The increase in glycemic index by a factor of three results in carbohydrates entering the blood stream three times more quickly, spiking the blood sugar, generating a strong insulin response and more forcefully activating the glucose control mechanisms.

Figure 10A:
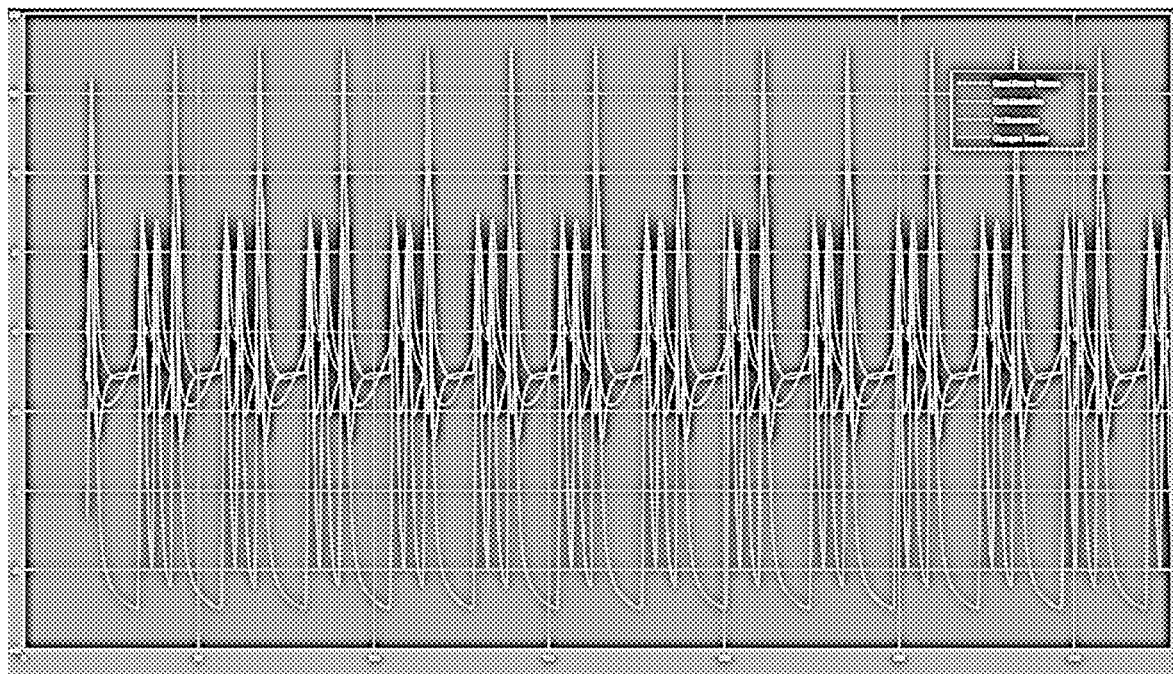
FIG. 10A is a plot illustrating metabolic energy sources and glycogen transfer for the case in FIG. 8A but with high glycemic index in accordance with some embodiments.
Figure 10B:
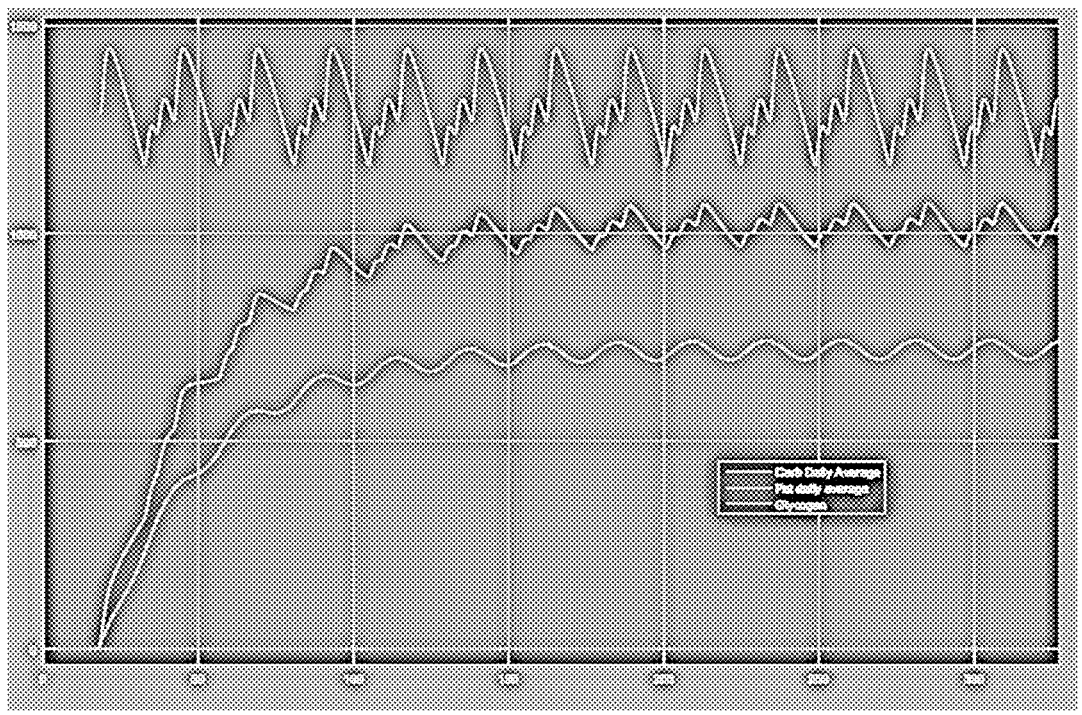
FIG. 10B is a plot illustrating daily energy substrate and glycogen stores for the case in FIG. 8B but with high glycemic index in accordance with some embodiments.

FIG. 10A is a plot illustrating metabolic energy sources and glycogen transfer for the case in FIG. 8A but with high glycemic index in accordance with some embodiments. Relative to FIG. 8A, blood glucose excursions are larger as are the glycogen transfer rates and carbohydrate metabolism. Relative to the low glycemic index baseline case, FIG. 10A clearly exhibits more rapid temporal variation consistent with a higher glycemic index in FIG. 8A, and larger excursion from nominal or average levels for all of the signals shown. FIG. 10B is a plot illustrating daily energy substrate and glycogen stores for the case in FIG. 8B but with high glycemic index in accordance with some embodiments. Relative to FIG. 8B, the peak carbohydrate metabolism is increased, the average fat metabolism is reduced and glycogen storage variability is increased.

Figure 11A:
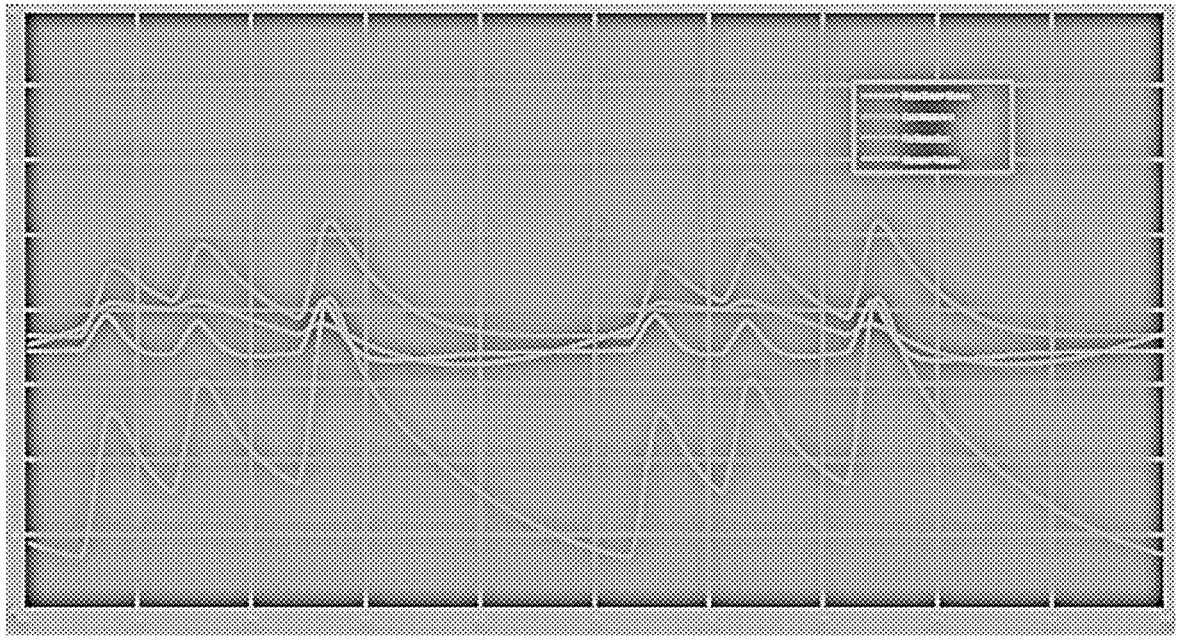
FIGS. 11A and 11B are side-by-side comparison of days 7 and 8 for two different glycemic index cases in accordance with some embodiments.
Figure 11B:
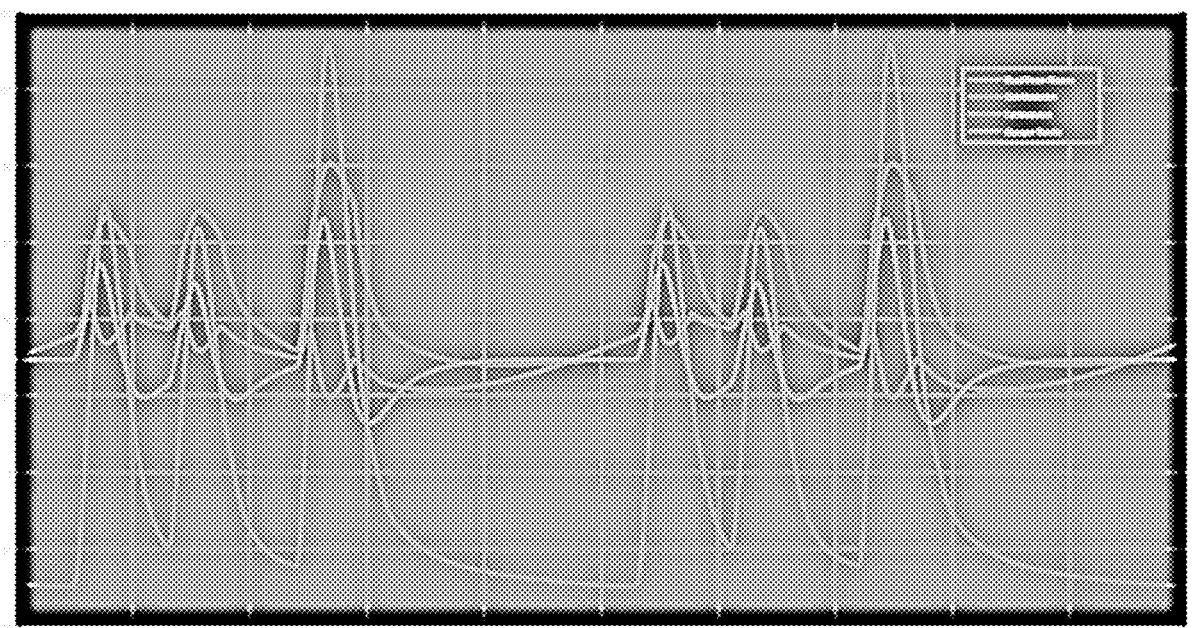

To better compare the two cases and understand the impact of the high glycemic index, FIGS. 11A and 11B are side-by-side comparison of days 7 and 8 for the two different glycemic index cases in accordance with some embodiments. Referring to FIG. 11A, corresponding to the low glycemic index case, the glycogen transfers, which are in units of kcal, are relatively small, on the order of 40 kcal (10 g) or less. The blood glucose level rises after each meal from the baseline set point of 30 kcal to a peak of around 40 kcal. There is little evidence of hypoglycemia. Note that while the dinner meal has the highest fat content, the fat metabolism, in units of kcal/hr, exhibits the lowest peak for the dinner meal because priority has been given to metabolizing blood glucose from the carbohydrate content of the meal and moving some of the excess blood glucose into glycogen storage.

In FIG. 11B, corresponding to the high glycemic index case, the blood glucose excursions are larger, peaking at 66 kcal with lows less than 13 kcal, indicative of hypoglycemia, and the glycogen transfer excursions are also larger with 110-kcal storage peaks and 30-kcal retrieval peaks. The fat metabolism is suppressed relative to the low glycemic case since as the as the blood sugar spikes due to the higher glycemic index, carbohydrate metabolism peaks and reliance on fat to meet metabolic energy needs is suppressed. At the same time more of the dietary carbohydrate intake is being moved into glycogen storage. These actions are all driven by higher levels of circulating insulin. At the completion of carbohydrate digestion blood glucose rates fall precipitously since there is no longer a source of glucose but the circulating blood insulin level does not return to normal immediately leading to episodes of hypoglycemia. In a real situation rather than a simulation, these hypoglycemic events might lead to additional carbohydrate snacking in response to the low blood glucose. However, in the simulation, the feeding schedule is prescribed (which one might think of as a dieter with an "iron will" or a clinical study in which diet is strictly controlled).

Figure 12A:
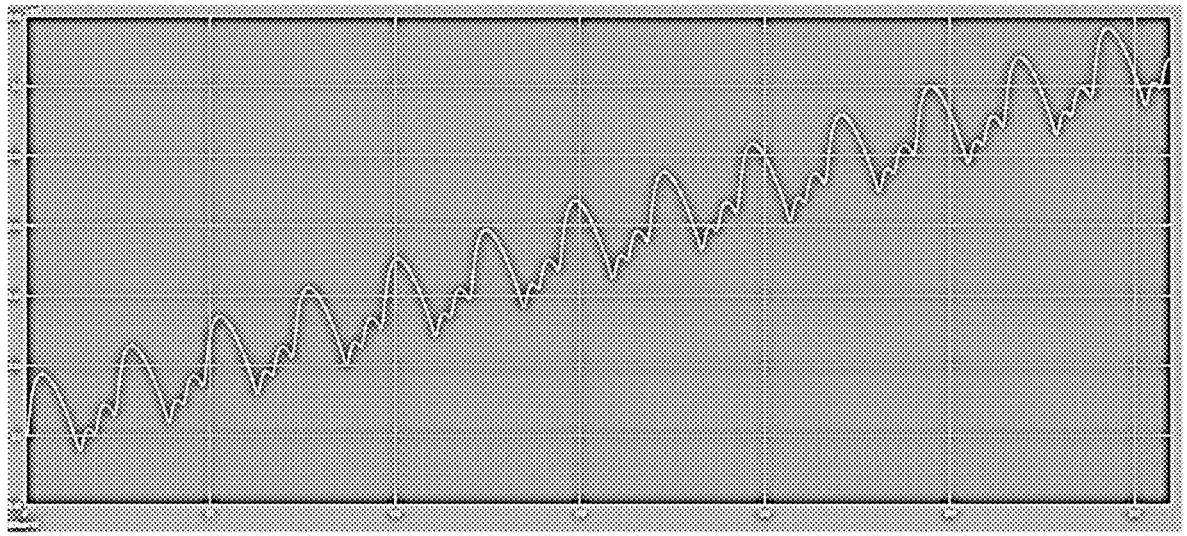
FIG. 12A is a plot illustrating change in fat storage resulting from increasing glycemic index of dietary carbohydrates in accordance with some embodiments.

FIG. 12A is a plot illustrating change in fat storage resulting from increasing glycemic index of dietary carbohydrates while preserving the baseline dietary caloric intake in accordance with some embodiments. Total increase in stored fat over the two-week simulation is small (1000-kcal equivalent to a weight gain of about one-quarter pound) but is indicative of an energy imbalance induced solely by a change in glycemic index. Since the metabolic response to the blood sugar spikes is to increase reliance on circulating glucose to meet energy needs while reducing reliance on circulating fat, the net result, as shown in FIG. 12A, is that body weight is increased as dietary fat moves into storage during episodes of high blood glucose. As a response to the subsequent episodes of hypoglycemia, glycogen, rather than the dietary fat, is moved out of storage to counteract the resulting low blood glucose.

Since the baseline model exhibited an energy balance, with a basal metabolic rate of 1800 kCal/day and a food intake of 1825 kCal/day, one might wonder why simply increasing the glycemic index would result in weight gain when the system was previously in energy balance. The answer to the apparent mystery of where the extra energy came from to produce weight gain has to do with one of the four control mechanisms identified in TABLE 1. In particular, as blood glucose levels rise, carbohydrate metabolism increases in order to dispose of glucose at a higher rate. The increased metabolism may take the form of higher body temperature, higher agitation, but, apart from actively increasing exercise, there is a limit to the total metabolic rate that can be achieved, which in the baseline model considered here is set to 100 kcal/hr. In the baseline energy-balanced example with low glycemic index, the maximum metabolic rate was never approached. However, with the higher glycemic index, the maximum metabolic rate needed to control the blood glucose is higher than the allowable maximum which leads to higher rates of glycogen storage and lower rates of fat metabolism resulting in higher levels of fat storage. During the episodes of hypoglycemia, the metabolism adapts to lower values and begins recruiting stored glycogen, not the previously stored fat, to raise blood glucose levels. The fat that was stored during the blood glucose spikes remains in storage since it will not help with blood glucose control. The overall cycle of the adaptive metabolism rate hitting a maximum followed by a nadir, lowers the average metabolism over the course of the three meals and the reduced average energy demands account for the increase in body fat.

Figure 12B:
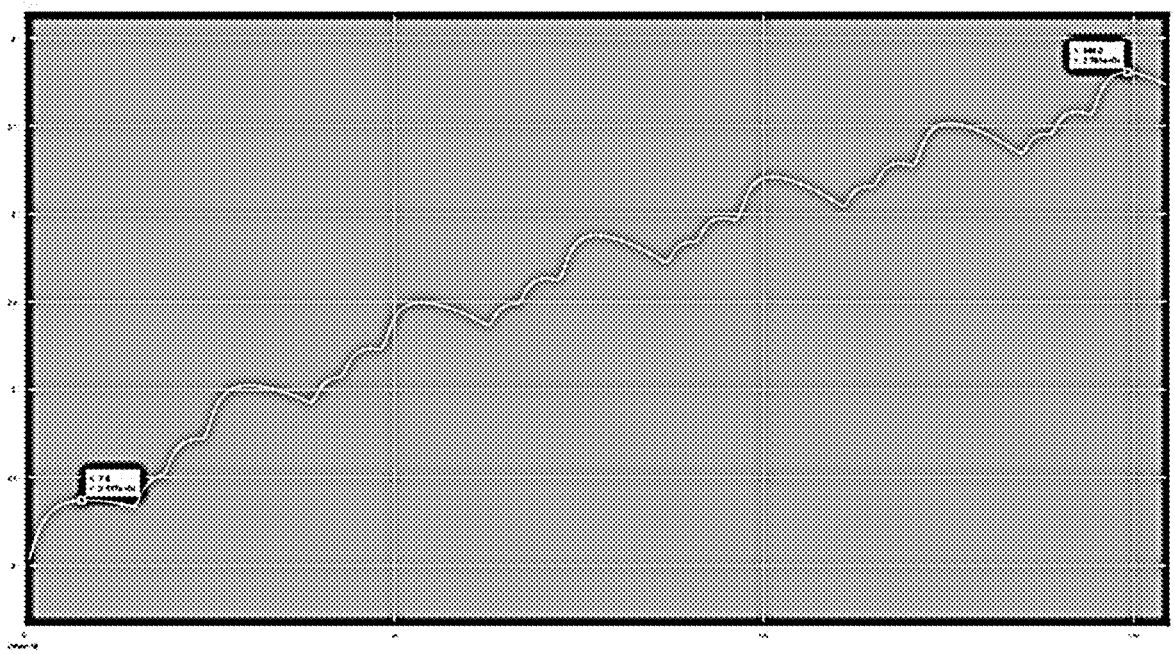
FIG. 12B is a plot illustrating change in fat storage resulting from increased dietary intake of 300 kCal/day with no compensating exercise in accordance with some embodiments.

The previous examples did not include any explicit exercise periods. To further demonstrate the efficacy of the model and the insights it affords, the model is returned to the reference diet defined in TABLE 3, but 100 kcal are added to each meal of the three daily meals, increasing the daily caloric intake from 1825 kcal to 2125 kcal. The glycogen storage is also initialized to full capacity at the start of the simulation, which may be representative of a sedentary individual. FIG. 12B is a plot illustrating change in fat storage resulting from increased dietary intake of 300 kCal/day with no compensating exercise in accordance with some embodiments. As shown in FIG. 12B, without the introduction of exercise, the increased calorie intake of 300 kCal/day results in a fat gain of 4090 kcal (about 1 lb) during the course of the two-week simulation.

A misconception sometimes promoted by fitness trainers is that "if you want to lose weight, you should preferentially engage in low intensity exercise, such as walking, since it is fat burning." Without question, low intensity exercise favors fat over carbohydrate oxidation. However, in terms of optimal weight loss, this advice ignores the complex interactions of the metabolic subsystems and the priority placed on blood glucose control. In other words, without a quantitative model to guide understanding, it is easy even for the experts to be misled regarding the impact of diet and exercise choices. To illustrate, the simulation is run again, this time adding exercise to offset the 300 kCal/day increase in dietary intake. All of the exercise is first added as low-intensity fat burning, and then the simulation is repeated with all of the exercise represented as high intensity carbohydrate burning exercise. For the purpose of comparison, the exercise is begun each day at 6 am and is 1.5 hours in duration with a total calorie expenditure of 150 kcal/hr. The 150 kcal/hr is not representative of high intensity exercise, but the same time duration and calorie rate for the carbohydrate burning exercise are used to keep as many variables the same for the sake of comparison and to focus attention on the impact of fat burning versus carbohydrate burning. In terms of justifying this assumption, one could imagine high intensity exercise with rest periods interspersed in order to achieve the same average kcal rate as the low intensity exercise over the 1.5 hour duration.

Figure 13A:
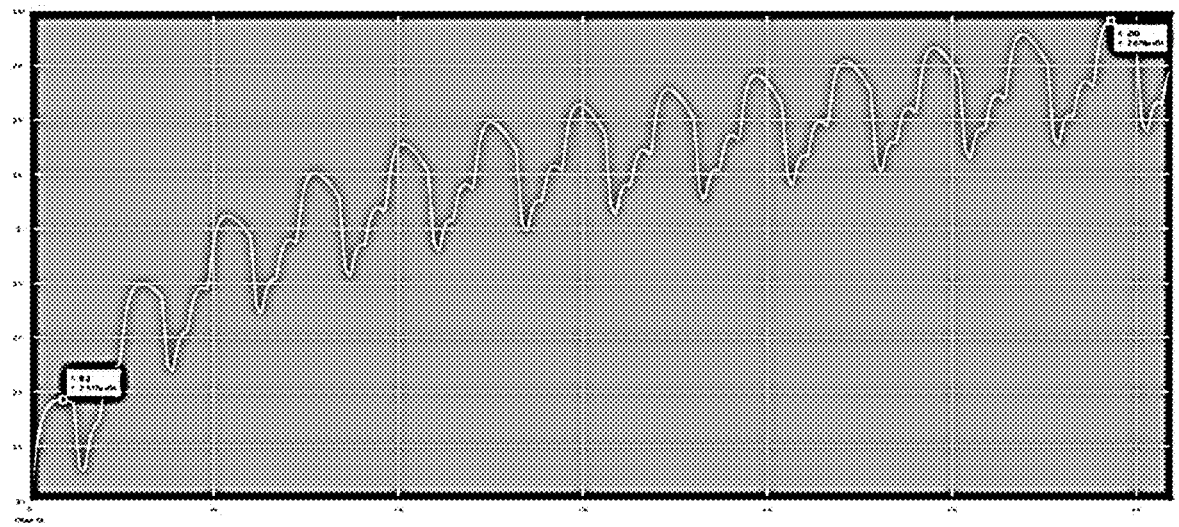
FIG. 13A is a plot of change in fat storage resulting from increased dietary intake of 300 kCal/day with fat burning exercise regimen of 225 kCal/day in accordance with some embodiments.

FIG. 13A is a plot of change in fat storage resulting from increased dietary intake of 300 kCal/day with fat burning exercise regimen of 225 kCal/day in accordance with some embodiments. As shown in FIG. 13A, the fat burning exercise reduced the weight gain from 4090 kcal with no exercise over the two week simulation, down to 1390 kcal with fat burning exercise. Note however that the positive slope on the fat accumulation curve implies that additional gains will occur in subsequent weeks under this feeding and exercise regimen.

Figure 13B:
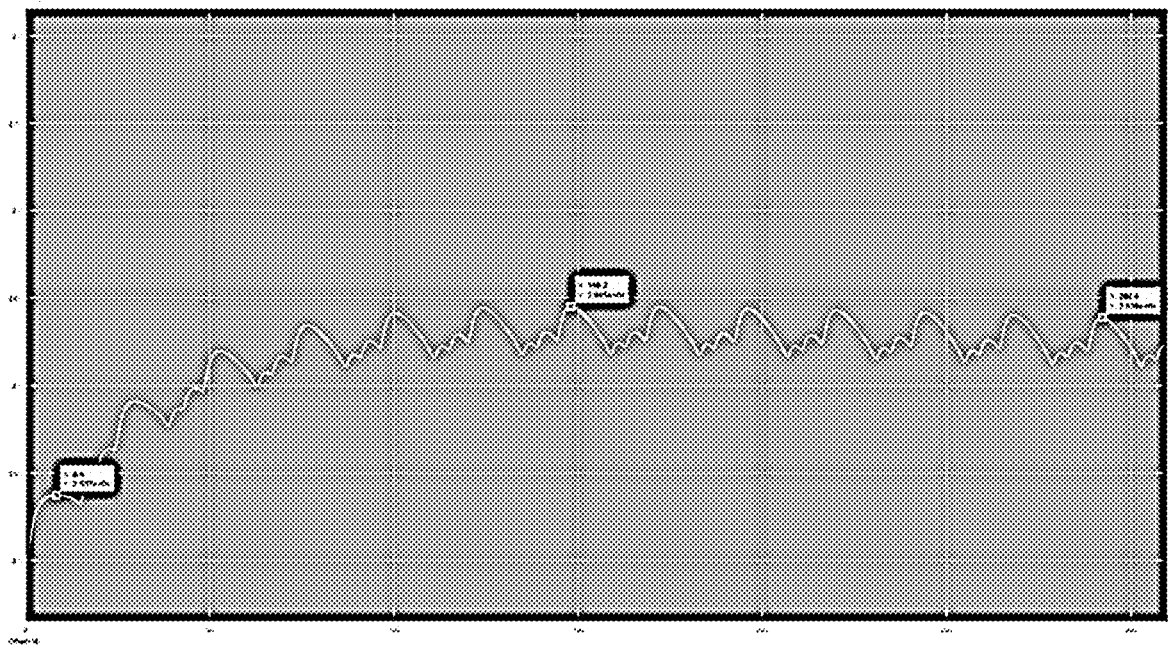
FIG. 13B is a plot of change in fat storage resulting from increased dietary intake of 300 kCal/day with a carbohydrate burning exercise regimen of 225 kCal/day in accordance with some embodiments.

In comparison, FIG. 13B is a plot of change in fat storage resulting from increased dietary intake of 300 kCal/day with a carbohydrate burning exercise regimen of 225 kCal/day in accordance with some embodiments. As indicated in FIG. 13B, carbohydrate burning exercise of the same calorie value and duration as the fat burning exercise results in a peak fat gain of 1080 kcal on day 6, the weight gain then begins to fall off slightly to a stable 1020 kcal by the end of the second week.

The fact that the same level of energy expenditure leads to different body fat outcomes for fat burning versus carbohydrate burning exercise may not seem surprising, but it does seem counter-intuitive that fat burning exercise would be the less effective exercise to achieve weight loss. This and the previous example clearly reveal the inadequacy of a simple calories-in/calories-out model of weight loss.

While the executable metabolic model of FIG. 6 behaves as expected for the contrived examples described in the previous sections, a more rigorous evaluation of the model fidelity may require comparison with carefully controlled studies in which the dietary intake, activity levels, and metabolic state are monitored over one or more diurnal cycles. A challenge in validating the metabolic model in this way is that few published studies provide a complete description the metabolic state of the subjects at the beginning of the study or report macronutrient composition of meals and feeding and exercise schedules in sufficient detail. For example, there is seldom knowledge of the state of an individual's glycogen stores at the beginning or end of an experiment, and the previous examples have shown that the state of glycogen stores has a significant impact on how an individual responds to a high carbohydrate diet.

From a modeling perspective, TABLE 4 below summarizes the desired information for proper initialization of a metabolic model, according to some embodiments, and identifies the corresponding parameters reported in three of the more comprehensive studies uncovered in the literature and incorporated by reference herein: Acheson et al., *Am. J. Clin. Nutrition*, 48:240-47 (1988); McDevitt et al., *Am. J.*

Clin. Nutrition, 74(6):737-46 (2001); and Jebb et al., Am. J. Clin. Nutrition, 58:455-62 (1993).

TABLE 4

| Info Documented | Desired | Acheson (1988) | McDevitt (2001) | Jebb (1993) |
|---|---|---|---|---|
| Duration (days) | Days to observe trends | 3 + 7 + 2 | 4 | 7 + 12 |
| Number of subjects | More is better | 3 | 13 | 5 |
| Subject physiology | Gender, age, BMI, fitness | Young male athletes | Middle-aged women | Healthy, ages 19-42 |
| Body composition | Measured at least daily | Weight, BMI, % body fat | Weight, BMI, DXA | Weight, BMI, density |
| Fat and carbohydrate balance | Measured daily | Daily | 4-day aggregate | Daily |
| Subject BMR | Measured daily | N/A | N/A | 1 hour per day |
| Initial glycogen stores | Known state | Depleted at start | N/A | N/A |
| Energy expenditure | Measured at least diurnally | Daily average | 4-day aggregate | Daily average |
| Exercise | Intensity and duration | 3 per day | 4 per day | Ergometer 3 × 40 min |
| Meal schedule | Time and duration | 3 per day | 4 per day | N/A |
| Meal composition | Macronutrients, GI | Daily mix, no GI | 4-day aggregate | Macronutrients, kcal |
| Hydration | Daily intake | N/A | N/A | N/A |
| RQ | Minimum hourly | Daily average | N/A | Daily average |
| DNL rates | RQ and $^2H_2O$ | Daily by RQ > 1 | $^2H_2O$ trace to fat stores | N/A |
| Protein metabolism | Quantified through urinalysis | Quantified | N/A | Urinalysis |
| Blood plasma analysis | CGM, insulin, leptin, triglycerides throughout day | 7 × triglycerides, insulin, glucose, lipoproteins | Triglycerides, insulin, glucose, leptin at 96 hours | N/A |

For example, in Acheson (1988), a comprehensive fourteen-day metabolic energy balance study included a nearly complete description of the parameters necessary to establish a ground truth reference for validating the efficacy of the metabolic state model according to some embodiments. Briefly, three healthy young men, ages 21-22, weights 62-72 kg, heights 174-180 cm, and body fats 11-14%, with no family history of diabetes or obesity participated. During the first three days, the subjects consumed a restricted diet, high in fat and low in carbohydrates, and followed an exercise program to deplete their glycogen stores prior to tracking the energy balance over a period of ten days. Halfway through this energy restrictive period, the subjects were admitted into a whole room indirect calorimetry chamber in which respiratory exchange measurements were to be continued for ten days. After 36 hours in the chamber, their diet was changed to a high-carbohydrate, low-fat diet that was ingested for the following seven days. During the last two days, while still in the chamber, the subjects received limited amounts of a high protein diet essentially devoid of carbohydrates. The subjects then left the respiration chamber but continued to consume the high-fat, low-carbohydrate diet for a further two days.

The restricted high-fat, low-carbohydrate diet consumed on days 1-3, 13, and 14 provided 1600 kcal comprising 15% protein, 75% fat, and 10% carbohydrate. During the overfeeding period (days 4-10 inclusive), the high-carbohydrate, low-fat diet provided 3600 kcal, comprising 11% protein, 3% fat, and 86% carbohydrate. Energy intake was increased progressively each day while the composition was kept constant with the intent to provide 1500 kcal in excess of the previous day's energy expenditure, which was measured in the respiration chamber. By day 10 the energy intake had thus increased to 5000 kcal. For the next (and last) two days in the respiration chamber, the subjects consumed a high-protein, low-calorie diet (protein sparing modified fat, 600 kcal). The diet was then changed to the same restricted high-fat, low-carbohydrate diet eaten on days 1-3 for the last 2 days of the experiment spent outside the chamber.

Figures 14A, 14B:
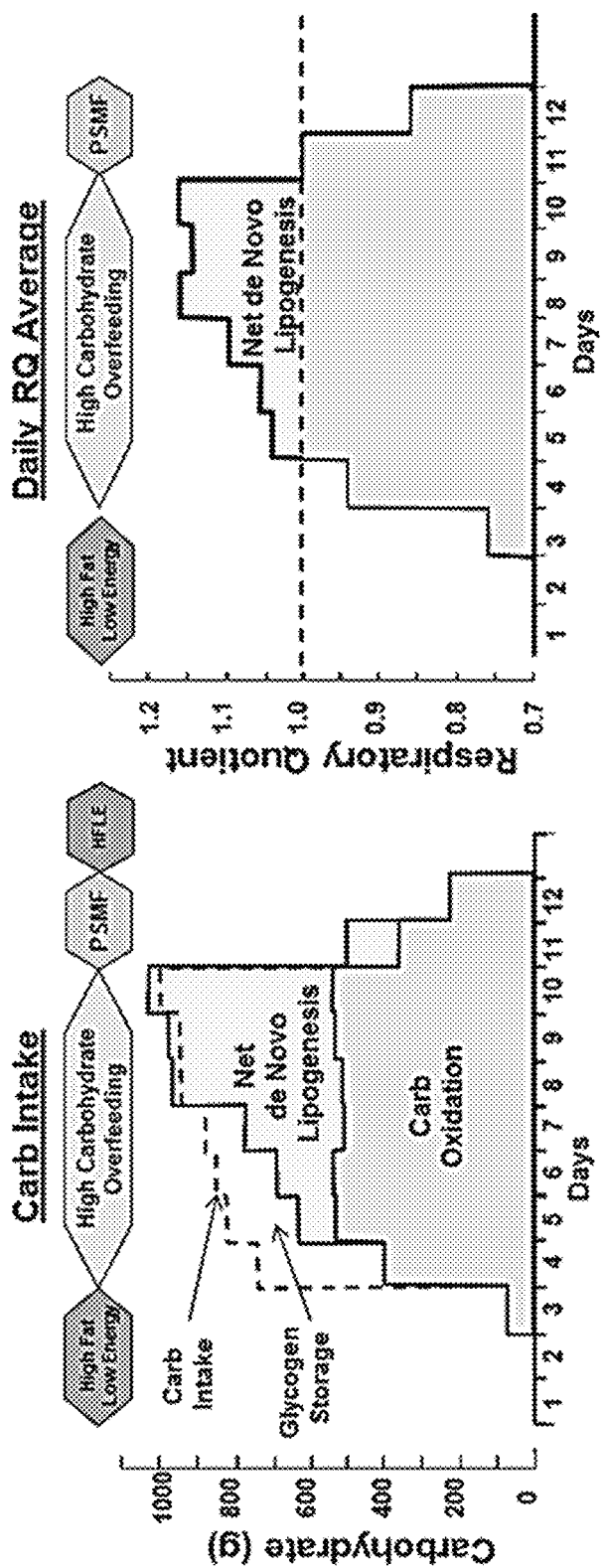
FIGS. 14A and 14B are plots illustrating the results in carbohydrate intake and daily RQ average from a published carbohydrate overfeeding experiment.

FIGS. 14A and 14B are plots illustrating the results in carbohydrate intake and daily RQ average of this carbohydrate overfeeding experiment. Note that from the onset of carbohydrate overfeeding starting on day 4, it took more than 24 hours for the daily average RQ to exceed 1.0 from a glycogen-depleted starting point of 0.75, and 4 days for the carbohydrate over feeding to effectively saturate the glycogen storage capacity and raise daily average RQ to its maximum observed value of 1.16.

FIGS. 15A-15F are plots comparing published results from the carbohydrate overfeeding experiment with results produced by a metabolic state model simulation in accordance with some embodiments. The metabolic model was initialized with the data corresponding to the dietary intake, activity, and average physiology of the three subjects in the carbohydrate overfeeding experiment. The solid curves in FIGS. 15A-15F represent the composite values for the three individuals involved in the study as reported in the published paper. With the exception of FIG. 15C, the dotted curves represent the values predicted by the metabolic state model given the feeding and exercise schedules during the study. In some embodiments, the model may include a protein module; however, in this case, the caloric values of the protein macronutrients, shown in FIG. 15A, were lumped with the fat input. Unlike the study, which took fourteen days to complete, the simulation of the study completed in less than one second.

Figure 15A:
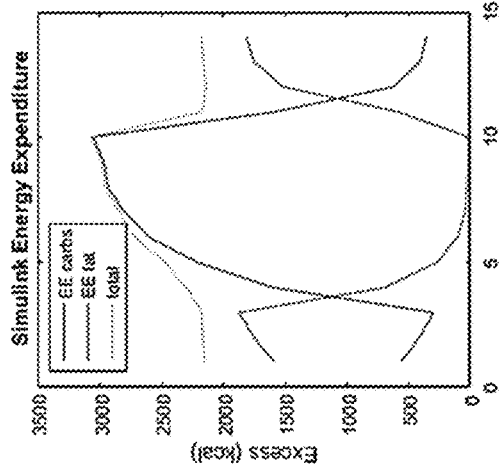
FIGS. 15A-15F are plots comparing published results from the carbohydrate overfeeding experiment with results produced by a metabolic state model simulation in accordance with some embodiments.
Figure 15B:
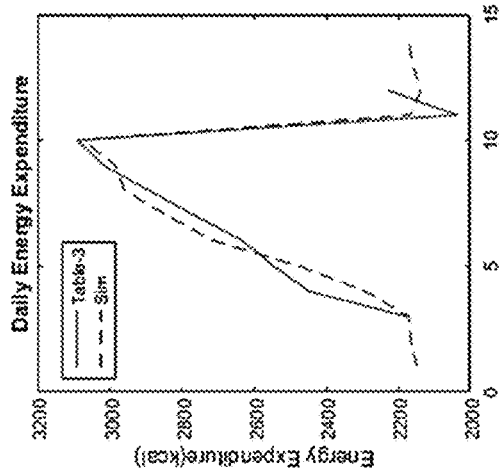
Figure 15C:
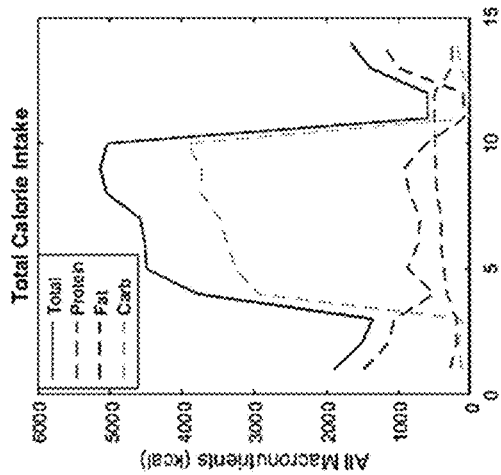
Figure 15D:
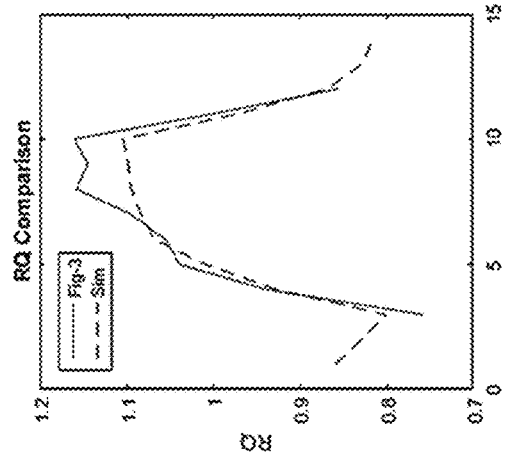
Figure 15E:
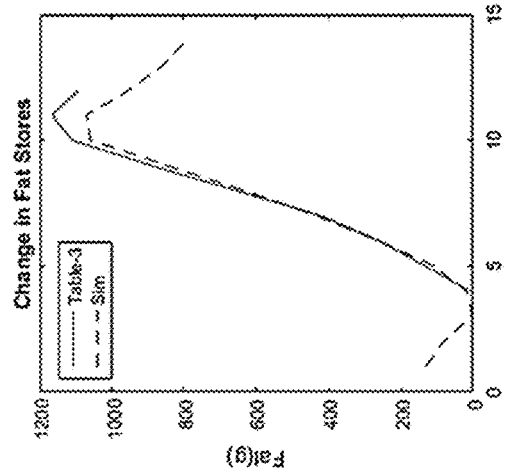
Figure 15F:
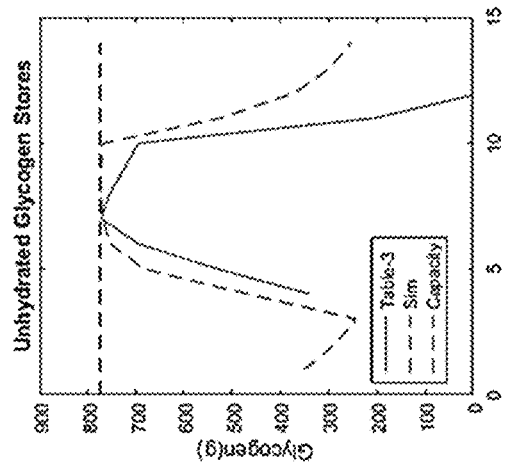

A number of the measured parameters from the study are compared to the simulation output, including total calorie intake in FIG. 15A, daily energy expenditure in FIG. 15B, total energy expenditure in FIG. 15C, unhydrated glycogen storage in FIG. 15D, change in fat stores in FIG. 15E, and RQ in FIG. 15F. The degree of correlation between the published data and the simulated output provides compelling evidence that, without resorting to detailed modeling of cellular metabolic pathways and processes, the impact of dietary macronutrients and exercise can be captured by this system-level feedback control model.

Realizing that blood glucose control is a critical function that takes precedence over other functions of the homeostatic control system leads to a somewhat different perspective regarding the causes and treatments for excess body weight and obesity. TABLE 5 below compares some of the implications of the metabolic state model to commonly held views.

TABLE 5

| Metric | Conventional View | Model View |
| --- | --- | --- |
| Obesity | Contributor to T2-diabetes | Mechanism by which the body attempts to avoid becoming diabetic |
| High insulin levels | Caused by insensitivity to Insulin (Insulin Resistance) | Caused by overwhelming the 4 glucose control actuators |
| Diet for weight loss | Requires overt control of calorie intake/expenditure | Requires active avoidance of carbohydrate "overconsumption" |
| Exercise for weight loss | Low intensity is best because it's fat burning | Choose exercise to counteract macronutrient imbalance |
| Feedback for weight loss | On-demand body weight measurements (scale) | On-demand metabolic state measurements (RQ, insulin, etc.) |
| Excess body weight population trend | Root causes are decreased activity and larger food portions | Root causes are historical changes in macronutrient mix that subvert homeostatic control loops |

As noted above, the human body has only four actions to take to control blood glucose levels and two of these—shutting off fat burning and turning glucose into fat—lead to weight gain. Consequently, weight gain leading eventually to obesity is not necessarily the cause of diabetes, but rather the body's best effort to avoid becoming diabetic by clearing excess glucose from the blood stream. Eventually, when these four processes are overwhelmed, the diagnosis is diabetes, but it is not caused by obesity.

Similarly, high insulin levels are often attributed to insulin insensitivity whereas the model clearly shows that the glucose control options are rate limited, and as the pancreas increases the control signal (insulin), eventually the rate limits of the processes are reached. Over time, the burden of persistently high blood glucose levels may degrade the effectiveness of the control mechanisms, but the model suggests that the degradation of the response to insulin (insulin resistance) is not the precipitating event but a consequence of long-term overburdening of the glucose control mechanisms.

The fact that body weight may fluctuate by a kilogram or more during the course of a day and that body weight fluctuations are caused by a number of processes not related to fat gain or loss, means that body weight is only a reliable indicator of progress over time periods of many days or weeks. As a consequence, making the association between dietary and exercise choices and their impact on weight loss goals on any given day, whether good or bad, is challenging to discern by tracking body weight, since the impact may not be discernable for days.

Apparatus for Measuring RQ

Given the differences in the way individuals respond to dietary macronutrients and exercise, the challenge is provide feedback, on demand, regarding an individual's metabolic state. On a long-term basis, there are methods for quantifying metabolic health through blood draws and analysis, and many individuals obtain snapshots of their metabolic health during an annual physical. However, to control weight and assess daily choices regarding macronutrient intake and exercise, it would be beneficial to be able to measure blood glucose levels, insulin levels, and disposition of macronutrients on a daily or hourly basis. While a number of blood analysis measurements can now be made by means of finger pricks and reagent strips, including blood glucose and ketone levels, these measurements are invasive, require consumables which can be costly over time and, most importantly, don't directly reveal insulin levels or energy substrate mix.

However, referring to the block diagram of FIG. 3, there is a simple, non-invasive method of measuring individual energy substrate mix and inferring the state of three of the four metabolic control valves 326, 328, 330, and 332 in the diagram. While not a direct measure of insulin levels, knowledge of the state of these valves conveys information about metabolic health and normalcy of insulin levels. According to some embodiments, this may be determined non-invasively from an analysis of exhaled breath. The method is based on a simple breath analysis to measure a quantity known as the respiratory exchange ratio (RER) which, in the absence of short-term breathing and anaerobic exercise artifacts, is representative of the respiratory quotient (RQ) at the cellular level.

The burning of fat and carbohydrates to supply metabolic energy needs is essentially a combustion process and, as such, consumes oxygen ($O_2$) and produces combustion by-products, in particular carbon dioxide ($CO_2$). Furthermore, the ratio of $CO_2$ produced to $O_2$ consumed is different for fat burning than for carbohydrate burning. At the cellular level, the ratio of $CO_2$ produced to $O_2$ consumed is called the respiratory quotient (RQ) and is equal to 1.0 for carbohydrate combustion and 0.7 for fat combustion. If carbohydrates are being used exclusively to supply all of the metabolic energy needs of the whole body, the RQ will be about 1.0 and if fats are being used predominantly, the RQ will be closer to 0.7. As indicated in the discussion of the metabolic model, in general, metabolic energy needs are met by a combination of carbohydrate and fat burning, in which case the value of RQ provides an indication of the percent of metabolic energy derived from carbs versus the percent derived from fats.

The $O_2$ needed for combusting carbs and fats is drawn from inhaled air, and similarly, the $CO_2$ produced by the processes is expelled in exhaled air. Consequently, under a fairly broad set of conditions, measuring the gas concentration of an individual's exhaled breath, to determine the $O_2$ consumed and the $CO_2$ produced, provides all the information needed to determine the percent of metabolic energy derived from carbs versus fats. Protein can also be used to supply metabolic energy, but it is a minor player in supplying metabolic energy needs and, in any case, has an RQ in the mid-range between carbs and fats, nominally about 0.8 depending upon the details of the protein.

Clearly the ability to measure and track one's RQ would provide valuable information about the impact of specific food and exercise choices on metabolism, and thus provides a means to assess how dietary macronutrient choices and levels of activity drive the body's choice of fuels. The implication is that if a low-cost personal sensor can be developed, it can be used to provide information to the user on-demand regarding the current state of his metabolic system. Armed with such a sensor, one could, if desired, track the impact of dietary and exercise choices on, for example, an hour-by-hour basis including during exercise itself.

Apparatus for measuring and/or tracking RQ are disclosed according to some embodiments. An RQ device may provide real-time assessment of a subject's metabolic state. Because of the real-time measurement capacity of a subject's RQ device, RQ measurements may be used to effect immediate changes in a subject's behaviors that affect the subject's metabolic state, such as, for example, modification of nutritional intake and/or activity level. According to some embodiments, an RQ device includes and/or is communicatively coupled with a computer-implemented metabolic state model.

In some embodiments, such as those illustrated in FIGS. 16-19, systems and apparatus for measuring RQ use low-cost commercial electro-optical sensors which, because of their small size, weight, and power, have time constants longer than a breath. Consequently, the sensor design emphasizes the capture and holding of end-tidal portions of the exhaled breath sample in the measurement chamber during the inhale cycle in order to allow the slow sensors sufficient time to settle to an accurate measurement. The challenges to implementing this direct breath sampling sensor include:

1) avoiding condensation on the sensor, which is achieved in at least some embodiments by heating the sensor to the expected temperature of the exhaled breath;
2) preventing ambient air from entering the measurement chamber during inhalation, which is achieved in at least some embodiments by using multiple large valves to ensure low respiratory burden;
3) correcting for changes in measurement chamber conditions, which is achieved in at least some embodiments by providing sufficiently fast and accurate temperature and humidity sensors;
4) correcting for the inability of at least some sensors (too slow) to measure temporal variations in $O_2$ and $CO_2$ concentrations over each breath profile, which is achieved in at least some embodiments by incorporating an adaptive energy expenditure estimation algorithm.

Figure 16:
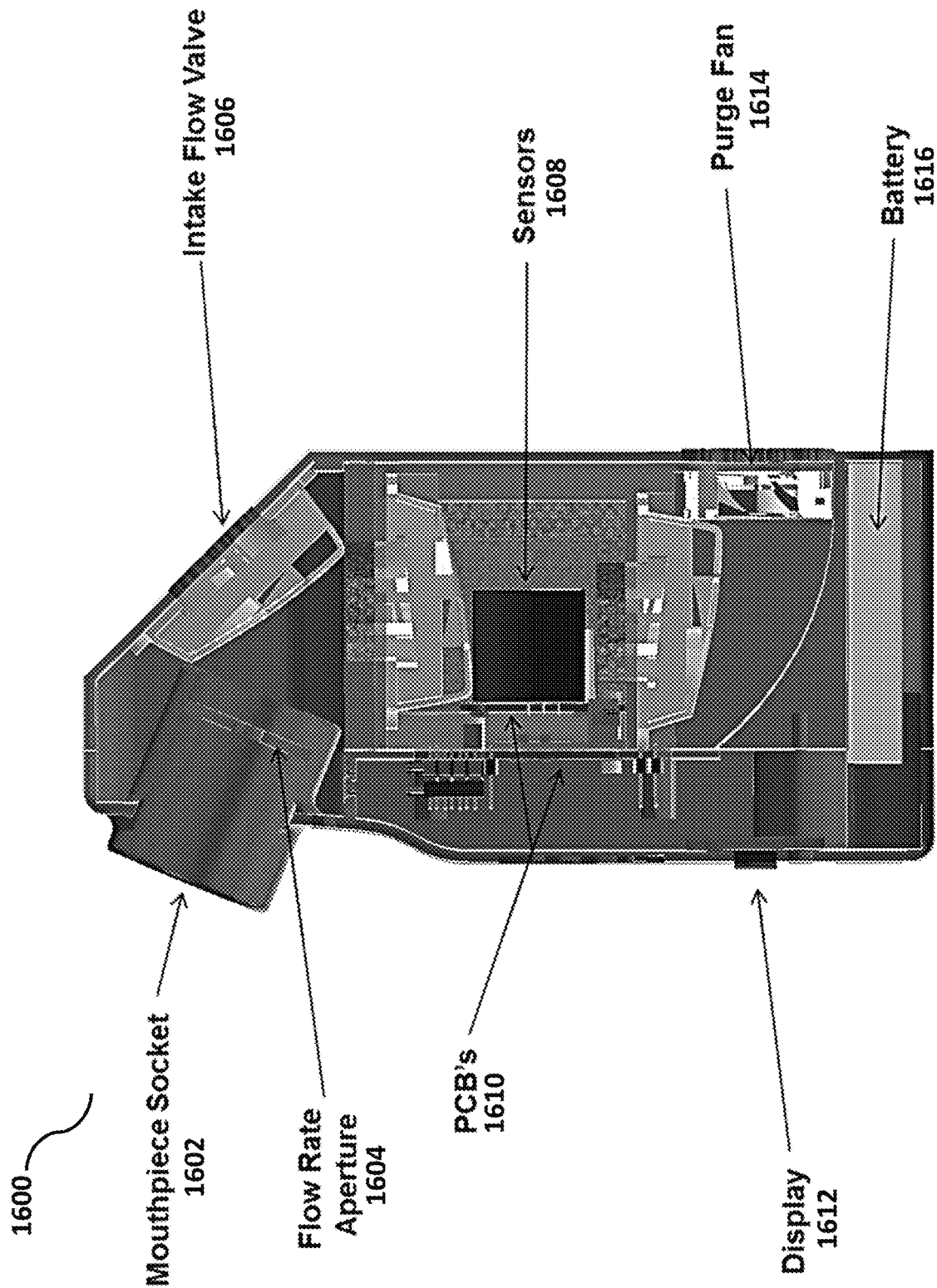
FIG. 16 is a cross-sectional view of an RQ device that includes provision for measuring flow rate and hence energy expenditure, in accordance with some embodiments.

FIG. 16 is a cross-sectional view of a portable RQ device 1600 in accordance with some embodiments. In FIG. 16, the RQ device 1600 includes a mouthpiece socket 1602, a flow rate aperture 1604, and an intake flow valve 1606 for receiving expired breath from a subject. As shown in FIG. 16, an input port on the device (i.e., the mouthpiece socket 1602) may be designed to be compatible with a sports cap on a disposable bottle, thereby providing for an inexpensive source of mouthpieces for the same or multiple users. The RQ device in FIG. 16 also defines a measurement chamber with sensors 1608 positioned therein. Printed circuit boards (PCBs) 1610, a display 1612, a purge fan 1614, and a battery 1616 are also included in accordance with some embodiments.

FIGS. 17A-17G are perspective views of components of the RQ device in FIG. 16 in accordance with some embodiments. FIGS. 17A-17C show more detailed views of the body of the device. FIG. 17D shows the circuit boards, FIG. 17E shows a flow sensor, FIG. 17F shows an $O_2$ sensor, and FIG. 17G shows a $CO_2$ sensor.

Figure 18B:
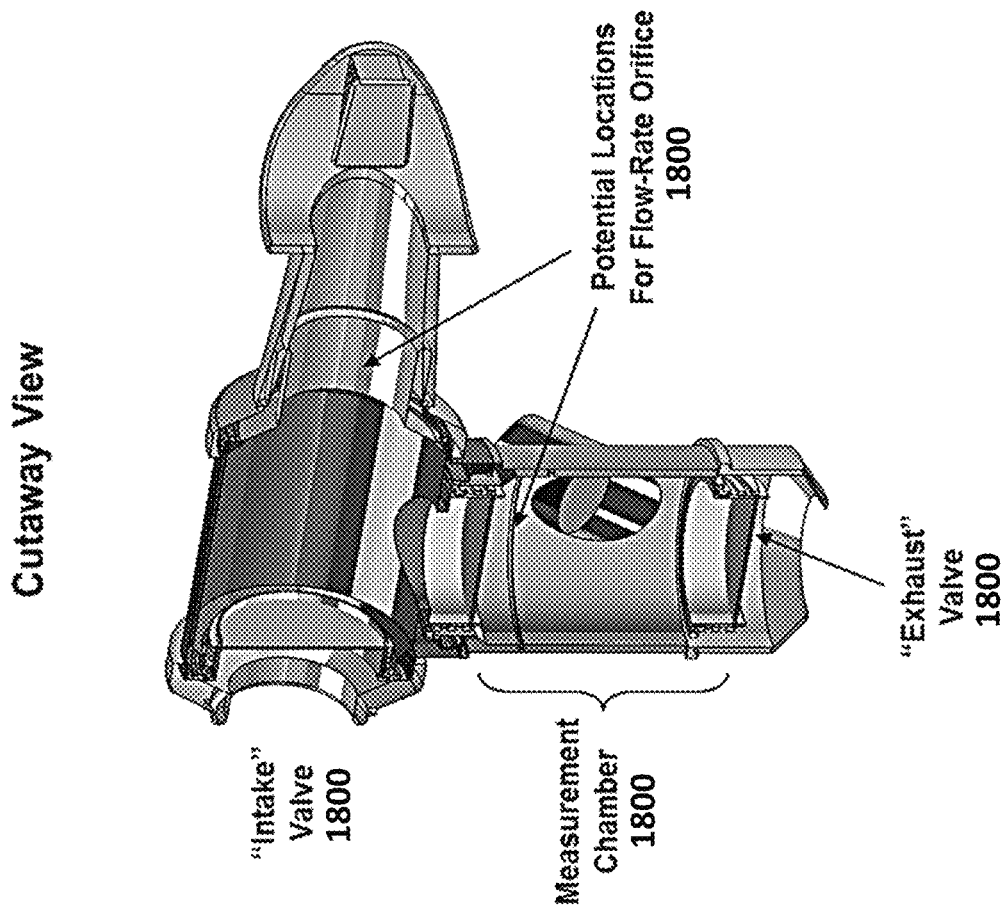
FIG. 18B is a cross-sectional view of the RQ device in FIG. 18A in accordance with some embodiments.
Figure 18A:
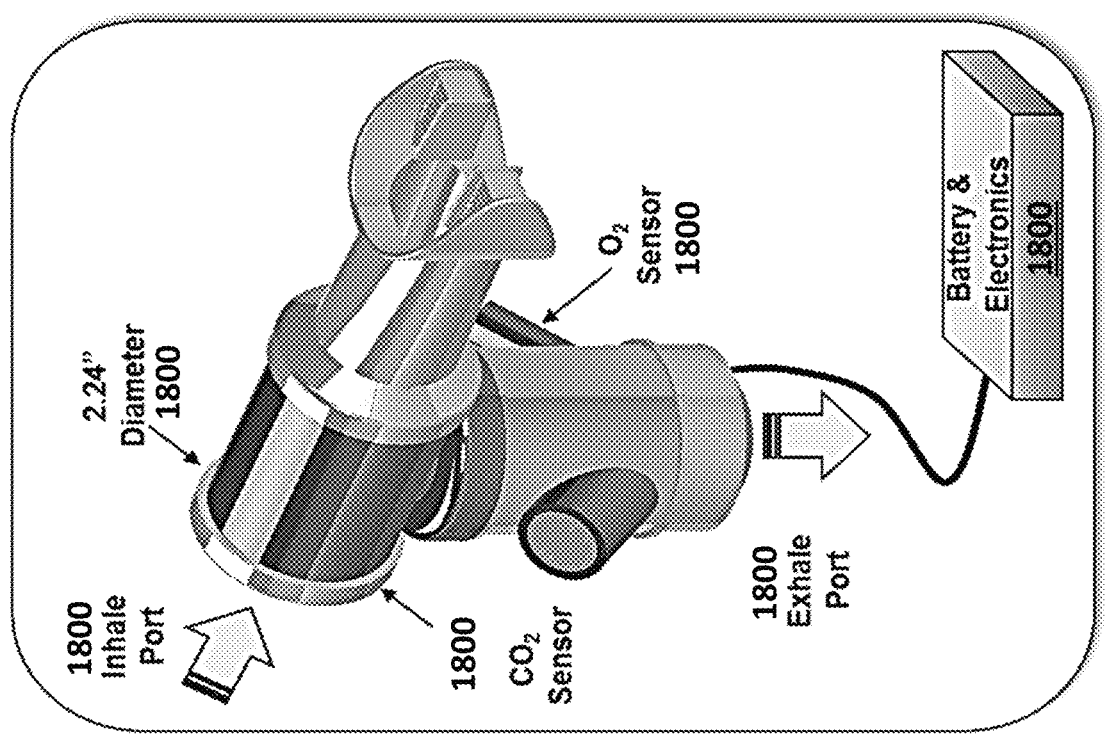
FIG. 18A is a perspective view of an RQ device, also with provision for a flow-rate sensor.
Figure 19:
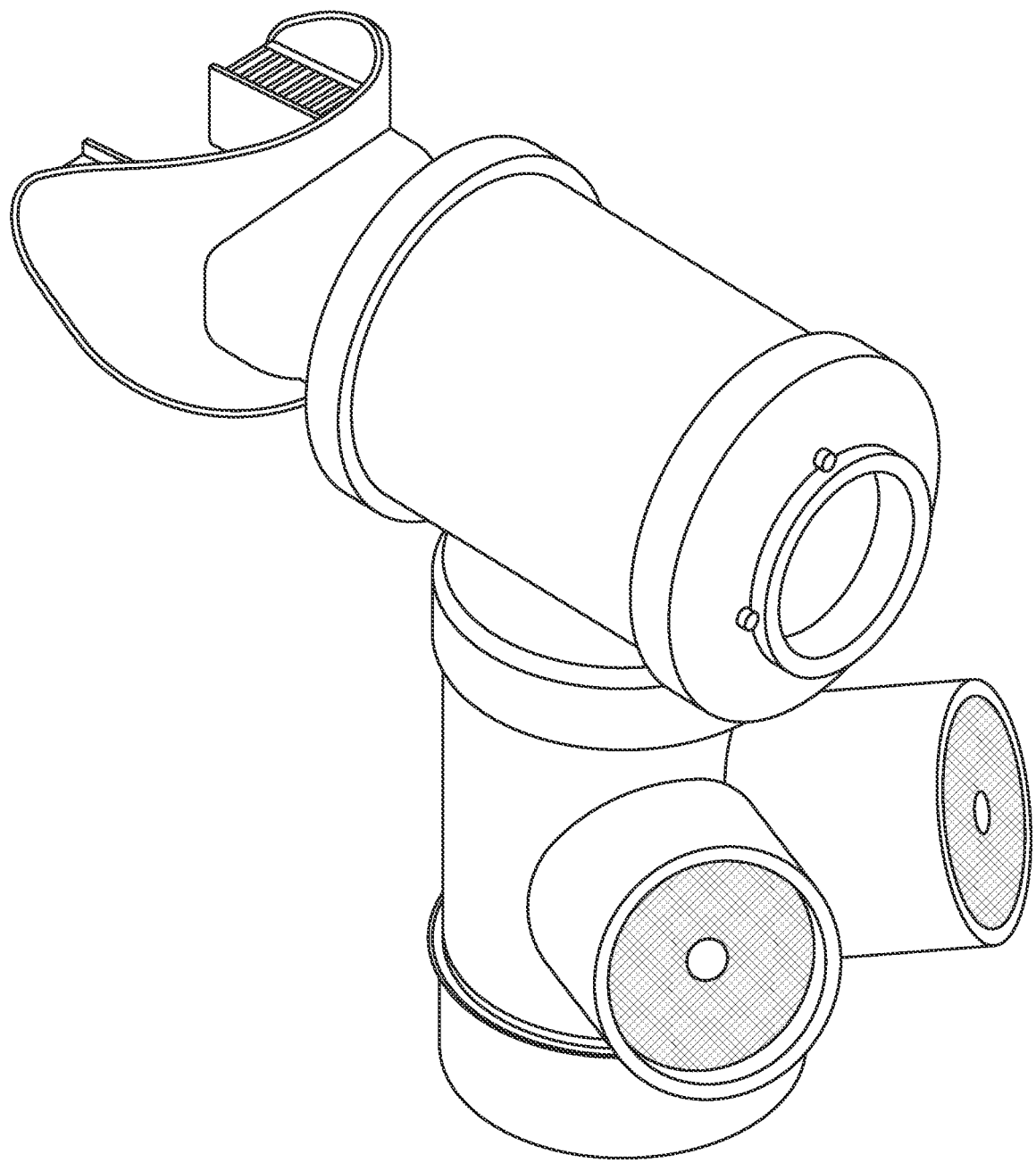
FIG. 19 is another perspective view of the RQ device in FIG. 18A in accordance with some embodiments.

FIG. 18A is a perspective view and FIG. 18B is a cross-sectional view of a second RQ device in accordance with some embodiments. The RQ device FIG. 19 is another perspective view of the RQ device in FIG. 18A in accordance with some embodiments.

An RQ device may have at least one input port. In some embodiments, a subject breathes in and out through a mouthpiece and/or cap that is attached to an input port of an RQ device. In other embodiments, a subject breathes in and out through one or more nasal tubes attached to an input port. The sampling of the subject's breath may be hands-free to allow for continuous sampling of exhaled breath without interfering with conversation, consumption of food and drink, or other activities and/or to facilitate the use of the device during movement or exercise. For example, a subject may be fitted with nasal tubes and/or a mouthpiece that connects to an input port and, optionally, is secured around the subject's head, thus allowing for hands-free sampling. Other hands-free configurations may include securing sampling tubes around a subject's torso, arm, neck, or lower body. Hands-free sampling is enabled, at least in part, because, unlike energy expenditure (Calorie) measurements, measurement of RQ does not require measuring of volume rates.

In some embodiments, an RQ device is fitted with one or more valves that control flow of air through the device during subject exhalation (e.g., an exhaust valve) and/or inhalation (e.g., an intake flow valve). A valve may help enforce unidirectional flow of air during the subject's breathing. Unidirectional airflow, in turn, may support more accurate measurements. A valve also may aid in capturing a subject's end tidal air, as explained further below. In some embodiments, at least one valve is provided for exhalation. Two, three, four, five, six, seven, eight, nine, ten, fifteen, or twenty valves may be provided for exhalation. In some embodiments, at least one valve is provided for inhalation. Two, three, four, five, six, seven, eight, nine, ten, fifteen, or twenty valves may be provided for inhalation. Different types of valves may be used. For example, the intake flow valve in FIG. 16 is a flapper valve. Flapper valves are also used as the intake and exhaust valves in FIGS. 18A and 18B in accordance with some embodiments.

In some embodiments, an RQ device includes a fan to remove or at least partially remove gases from the device and/or prevent or at least partially reduce condensation in the device. A fan may also contribute to keeping the measurement chamber closed during the initial period of exhalation and/or open only during the end-tidal portion of the breath. For example, the RQ device in FIG. 6 shows a purge fan. In some embodiments, an RQ device includes a shutter to enable the capture and measurement of a subject's expired end tidal air fraction, as explained further below.

According to some embodiments, an RQ device includes at least one electronic component for controlling and/or communicating information about the device including, but not limited to, measurements made with the device. The electronic components may be electrically coupled using one or more printed circuit boards as shown in FIGS. 16 and 17D. Additional electronic components for controlling and/or communicating information about the device may be external to the RQ device but communicatively coupled (with wires or wirelessly) with the RQ device as shown in FIG. 18A. An RQ device may be further configured to house an internal battery, as shown in FIG. 16, and/or to be coupled with an external power source, as shown in FIG. 18A. An internal battery may be rechargeable (with wires or wirelessly) or disposable. In further embodiments, an RQ device may include a user interface. The user interface may include an input component and/or an output component (e.g., visual, aural, and/or haptic signals or displays). For example, the RQ device in FIG. 16 includes a visual display screen. Alternatively or in addition, an RQ device may be coupled (with wires or wirelessly) with an external input device and/or output device (e.g., a smartphone, tablet, laptop, or other computing device).

In some embodiments, an RQ device includes one or more sensors or detectors. The one or more sensors may include a flow sensor and/or a gas sensor.

A flow sensor is a component for sensing a rate of fluid flow and may include, but is not limited to, a microsensor that measures the transfer of heat caused by the moving fluid (e.g., a thermal mass flow meter), a laser-based interferometer, a photoacoustic Doppler sensor, and/or a mechanical flapper valve or vane that is pushed by the fluid to drive, for example, a rotary potentiometer.

An RQ device may sample and/or measure a subject's end tidal breath, maximum expired $CO_2$, and/or minimum expired $O_2$. According to some embodiments, an $O_2$ sensor and/or a $CO_2$ sensor is arranged to capture the end tidal concentrations of $O_2$ and/or $CO_2$, respectively.

A gas sensor is a component for sensing and/or measuring one or more gas types and may include, but is not limited to, an electrochemical gas sensor, an infrared point sensor, an infrared imaging sensor, a semiconductor, a spectrophotometer, a tunable diode laser spectrometer, photoacoustic spectrometer, and/or a holographic gas sensor. In some embodiments, a gas sensor is an all-optical gas sensor for detecting and measuring a gas concentration using the characteristic optical/spectral absorption of the gas species. A gas sensor may be a slow gas analysis sensor.

According to some embodiment, optical gas sensing technology reduces the need for expendables and/or frequent replacement of consumable sensor elements such as electrochemical fuel cell sensors. For example, commercial sensors may use an electrochemical cell for $O_2$ detection, the anode of which is consumed during measurements such that the sensor requires frequent re-calibration and eventual replacement (typically after 6-12 months of use). Thus, an all-optical gas sensor may be used to minimize size, weight, power, and/or use of consumables.

In some embodiments, an RQ device includes a $CO_2$ all-optical gas sensor and/or an $O_2$ all-optical gas sensor. For example, an $O_2$ sensor may be a fluorescence quenching sensor, as shown in FIG. 17F, and/or a $CO_2$ sensor may be a nondispersive infrared (NDIR) sensor, as shown in FIG. 17G. In some embodiments, the housing/packaging of a commercially-available sensor (e.g., the $O_2$ sensor in FIG. 17F) may be modified by removing an apical portion of the housing and/or modulating a thickness of a ruthenium component of the sensor.

One challenge of using these low-power, low-cost sensors for the measurement of $O_2$ and/or $CO_2$ is that the sensor time constants may be long compared to the respiration periods and the time constants may be unequal in some embodiments. In order to compensate for the long and/or unequal time constants associated with the sensors, the measurement chamber of the device may be designed to be relatively small and relatively close to the subject's mouth. Such embodiments account for the effect of dead space air (i.e., the volume of air that is inhaled but does not take part in gas exchange). The dead space air associated with the mouth, esophagus, and upper lungs is exhaled first and subsequently pushed through the measurement chamber by remaining exhalant until, finally, the end tidal breath is captured in the measurement chamber where it resides during the next inhalation cycle.

In some embodiments, as a consequence, these slow gas analysis sensors are exposed to end tidal air during most of a breathing cycle and therefore asymptotically approach the true end tidal concentration of $O_2$ and $CO_2$ with only brief exposure to dead space air during the next exhalation. This technique of trapping only end tidal air in the measurement chamber may be accomplished through the use of low-cost, mechanical valves, as discussed above, that consume minimal or no additional power in accordance with some embodiments. The influence of a subject's dead space air may be reduced further by the use of a mechanical shutter, a vacuum pump, and/or a fan timed to keep the measurement chamber closed during the initial period of exhalation, and open only during the end tidal portion of the subject's breath.

Another challenge associated with the unequal time constants of the $O_2$ and $CO_2$ sensors is that at any instant of time, one sensor may have settled to, for example, about 90% of the final value while the slower sensor may only have settled to, for example, about 50% of the final value. Therefore, taking a ratio of the $CO_2$ concentration to the $O_2$ concentration measured at the same time may produce large errors. In order to contend with the unequal time constants of the sensors, in some embodiments, the measurements are not time-synchronized. Instead, a maximum value of $CO_2$ during a breath is measured, a minimum value of $O_2$ during a breath is measured, and these measurement are used to estimate the RQ value.

Following the acquisition of the minimum expired $O_2$ (i.e., end tidal $O_2$ sample) and the maximum expired $CO_2$ (i.e., end tidal $CO_2$ sample) the average RQ is computed over valid breaths as follows:

$$RQ_{AVG} = \frac{\sum \left[\frac{CO_{2exp}}{N_{2exp}} - \frac{CO_{2in}}{N_{2in}}\right]}{\sum \left[\frac{O_{2in}}{N_{2in}} - \frac{O_{2exp}}{N_{2exp}}\right]} \quad (6)$$

Figure 20:
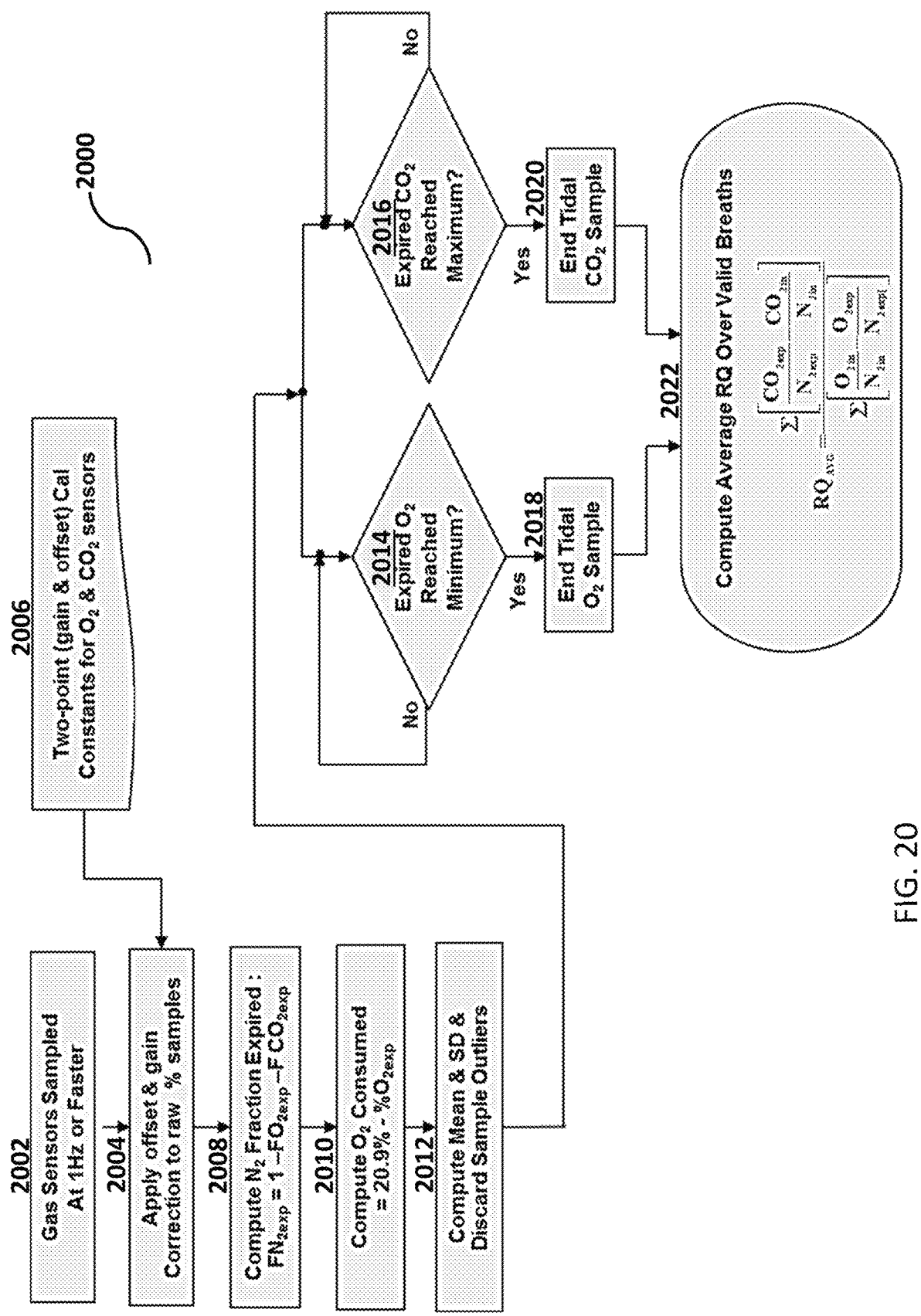
FIG. 20 is a process flow chart illustrating breath sampling in accordance with some embodiments.

FIG. 20 provides a process flow chart illustrating a method for breath sampling 2000 in accordance with some embodiments. In step 2002, gas sensors are sampled at at least 1 Hz. In step 2004, offset and gain correction is applied to raw sample data with two-point (gain and offset) calibration constants for $O_2$ and $CO_2$ sensors 2006. In step 2008, the fraction of expired nitrogen is computed using the following equation:

$$\% \text{ N}_{2exp} = 1 - \% \text{ O}_{2exp} - \% \text{ CO}_{2exp} \quad (7)$$

In step 2010, the fraction of oxygen consumed is computed according to:

$$\% \text{ O}_{2in} = 20.9\% - \% \text{ O}_{2exp} \quad (8)$$

In step 2012, the mean and stand deviations are computed. Sample outliers are discarded. If the fraction of expired oxygen has reached a minimum 2014 and fraction of expired carbon dioxide has reached a maximum 2016, then an end tidal oxygen sample 2018 and an end tidal carbon dioxide sample 2020 are used to compute average RQ over valid breaths in step 2022 according to equation (6) above.

Over a period of extended use, all gas sensing technologies are subject to drift. As a result, existing indirect calorimetric sensors either require frequent re-calibration with a precision gas mixture, or the use of a pre-calibrated expendable cartridge. An important improvement in some embodiments of an RQ device is the ability for a user to quickly and easily calibrate the sensor using an inexpensive and readily available $CO_2$ cartridge. Calibration of an $O_2$ sensor and/or $CO_2$ sensor may be achieved by performing a zero (offset term) and a span (gain term) calibration on each sensor. Typically this process would be performed by a trained technician in a laboratory using calibrated gas mixtures; however, that is unnecessary according to at least some embodiments. In some embodiments the zero gas concentration condition for both sensors can be met by purging the sensor chamber with a halocarbon gas obtained from a commercially-available aerosol "gas duster" container.

First, all-optical gas sensors may require less frequent full-scale calibration. In accordance with some embodiments, an RQ device, when turned on, may automatically or manually undergo a pre-use ambient air calibration that takes into consideration average ambient air levels of $O_2$ and $CO_2$. A limited ambient-air calibration may be performed each time a sensor is powered up. Ambient air calibration may assume that, except in very confined rooms with inadequate ventilation, dry ambient air $O_2$ concentration is about 20.9%, which may be adjusted downward to account for relative humidity, and $CO_2$ concentration is about 0.04%. Ambient-air calibration allows for an adjustment or correction of gain in an $O_2$ sensor (most susceptible to gain drift) and/or an adjustment or correction of offset in a $CO_2$ sensor (most susceptible to offset drift). Thus, in some embodiments, ambient-air calibration helps to maintain sensor accuracy over time.

Historical ambient-air calibration measurements may be stored in and/or accessible to an RQ device for subsequent comparison to future ambient $O_2$ and $CO_2$ measurements in order to determine an amount of drift in the settings. If predetermined amount of drift in the settings is exceeded, a full calibration cycle may be performed by the user.

A full calibration may be implemented, when necessary, automatically or manually by, for example, using a $CO_2$ cartridge in connection with the ambient-air calibration procedure. First, the $O_2$ gain and/or $CO_2$ offset may be computed at power up from ambient air. Subsequently, $CO_2$ cartridge may be introduced into the measurement chamber of an RQ device. In some embodiments, an RQ device includes a port or chamber for receiving $CO_2$ into the measurement chamber from a $CO_2$ cartridge. By filling the measurement chamber with $CO_2$, residual $O_2$ is purged or at least reduced. At that point, the zero offset for $O_2$ may be determined so that a full two-point calibration of the $O_2$ sensor is achieved. As the $CO_2$ leaks from the measurement chamber, it is replaced by ambient air, with a known or calculable concentration of $O_2$ (e.g., about 20.9%) and $CO_2$ (e.g., about 0.04%) in accordance with some embodiments.

Because the $O_2$ sensor has undergone a two-point offset and span calibration, it may serve as a calibrated reference, which together with the known or calculable concentration of $O_2$, may be used to determine a span calibration for the $CO_2$ sensor. For example, when the $O_2$ sensor reads about 16.72%, then about 80% of the $CO_2$ has leaked out of the measurement chamber and been replaced with ambient air, so the $CO_2$ sensor should measure a concentration of about 20%.

Although these sensors offer long term stability, another challenge associated with using optical gas sensors is that the optics are subject to contamination resulting in a loss of calibration. Because contamination of optical surfaces on a sensor may degrade accuracy of subsequent measurements and the humidity of exhaled air is close to 100%, a sensor may be heated to a temperature slightly higher than, for example, the subject's body temperature, in order to exceed the dew point and thus prevent condensation of moisture from exhaled breath on the sensor's optical surfaces in accordance with some embodiments. In some embodiments, a sensor is automatically or manually heated or allowed to warm to a predefined temperature including, but not limited to, 30° C., 31° C., 32° C., 33° C., 34° C., 35° C., 36° C., 37° C., 38° C., 39° C., 40° C., 45° C., or 50° C.

Figure 21:
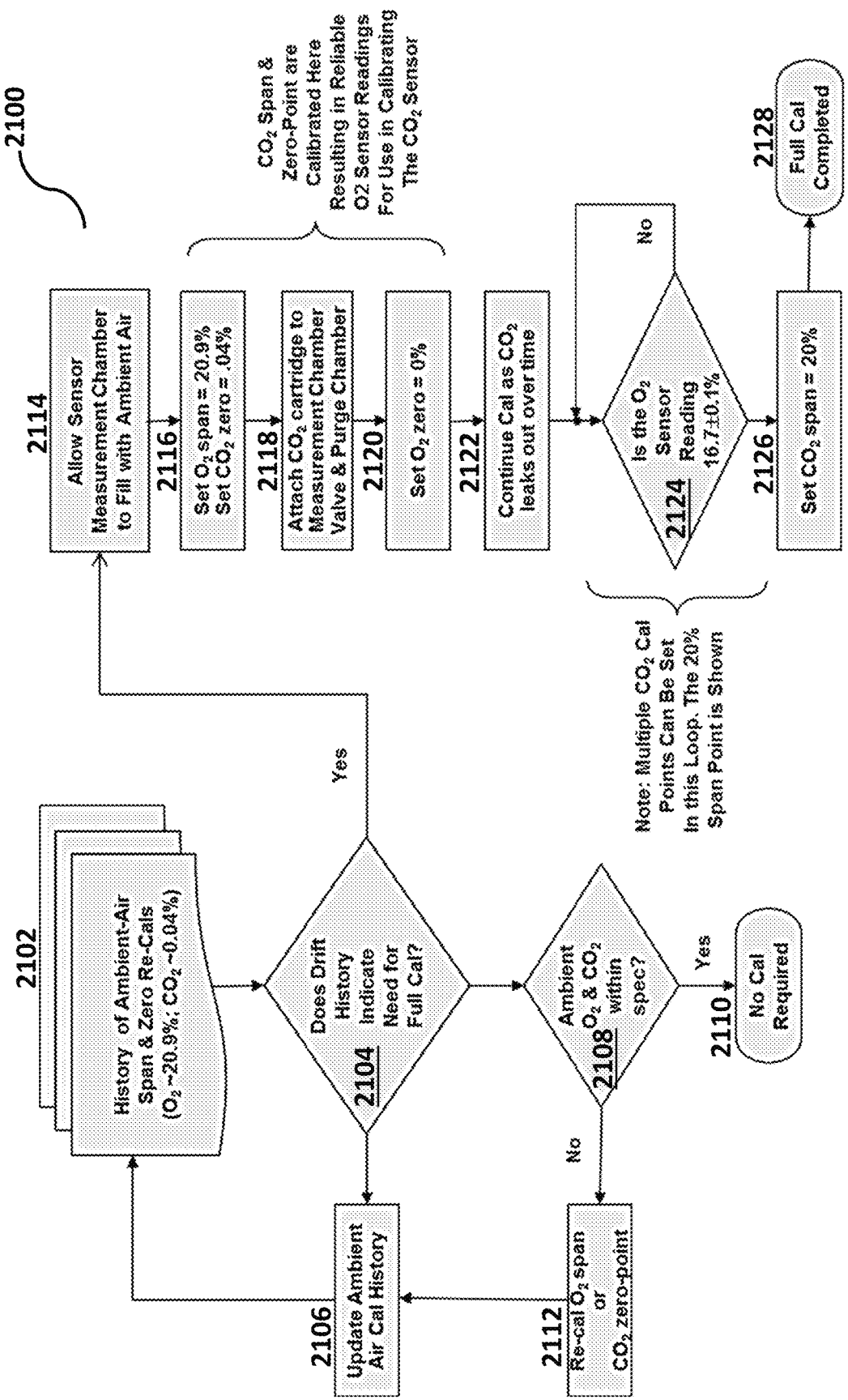
FIG. 21 is a process flow chart illustrating RQ device calibration in accordance with some embodiments.

FIG. 21 is a process flow chart illustrating a method for RQ device calibration 2100 in accordance with some embodiments. A history of ambient-air span and zero recalibrations 2102 is maintained. In step 2104, drift history is reviewed to determine whether full calibration is needed. If not, step 2106 is performed to update the calibration history. In step 2108, ambient oxygen and carbon dioxide levels are reviewed to determine whether they are within specification. If they are, no calibration is required 2110. If they are not within specification, oxygen span or carbon dioxide zero-point is recalibrated in step 2112 and the calibration history is updated 2106. However, if drift history indicates that full calibration is needed, the sensor measurement chamber is allowed to fill with ambient air in step 2114, oxygen span is set to 20.9% and carbon dioxide zero-point is set to 0.04% in step 2116, a carbon dioxide cartridge is attached to the measurement chamber valve to purge the chamber in step 2118, oxygen is set to 0% in step 2120, and calibration is continued as carbon dioxide leaks out over time 2122. Once the oxygen sensor reading is 16.7±0.1% in step 2124, the carbon dioxide span is set to 20% in step 2126, and full calibration is completed 2128.

The evolution of the design of the RQ devices in FIGS. 16, 17A-17G, 18A-18B, and 19, including the challenges associated with certain aspects of RQ measurement and the solutions provided, are detailed below in TABLE 6.

TABLE 6

| Challenge | 1st Gen Approach | Problems | Innovation |
|---|---|---|---|
| Breath sampling | Capture single end-tidal breath | RQ variable due to ventilation artifacts on a single breath | Average over several breaths |
| Multiple breath averaging | Require deep, slow breaths to accommodate slow $O_2$ sensor | Accentuates ventilation artifacts | Physically modify COTS sensor to gain about 10x speed up |
| Demarcate each breath sample and average RQs | Use $CO_2$ waveform shape to reliably demarcate breaths | $O_2$ min and $CO_2$ max not necessarily phased in time | Average $O_2$ and $CO_2$ separately rather than breath-by-breath RQs |
| Inhaling through sensor dilutes sample volume | Inhale through the nose and exhale through the mouth | Abnormal breathing pattern creates ventilation artifacts | Incorporate flapper valves to allow mouth breathing exclusively |

TABLE 6-continued

| Challenge | 1st Gen Approach | Problems | Innovation |
|---|---|---|---|
| Number of breath samples needed | Observe real-time RQ plot until steady state reached | Not a viable approach for a non-technical user | Compute mean and variance and stop when variance sufficiently small |
| Ventilation artifacts from cough, laugh, yawn, etc. | Observe real-time RQ plot to visually detect artifacts | Not a viable approach for a non-technical user | Discard outliers based on history of breath-by-breath averages |
| Condensation of about 100% RH breath fogs optics | Employ metal case and heat to 38° C. to avoid condensation | The power and time to reach 38° C. is prohibitive | Heat only the condensation sensitive components |
| Thermal insulation to speed and hold 38° C. temperature | Insulate measurement chamber with foam | Foam tends to preferentially absorb gas components | Employ impermeable insulation materials |
| $CO_2$ sensor calibration drifts over time | Use known gas mixtures to recalibrate $CO_2$ sensor | Not a viable approach for low-cost personal use | Employ $CO_2$ sensor model that allows calibration from ambient air |
| $O_2$ sensor calibration drifts over time | Use known gas mixtures to recalibrate $O_2$ sensor | Not a viable approach for low-cost personal use | Employ $O_2$ sensor model that allows calibration from ambient air |
| RQ can be biased by lactate buffering | Make only resting RQ measurements | Unreliable RQ measurements during intense exercise | Incorporate flow rate sensor to gauge exercise intensity from $VO_2$ |

According to some embodiments, an RQ device is designed and/or used to measure resting RQ. The underlying rational for measuring resting RQ is that the energy substrate mix at rest provides for a more accurate assessment of a subject's metabolic state. One design challenge to acquiring the subject's resting RQ is a potential for variations in the subject's breathing rate and ventilation, which would bias the RQ measurement. Thus, in some embodiments, an RQ device is designed to compute an RQ measurement based on an average of several breaths.

An RQ device may measure $CO_2$ concentration at a high temporal rate (e.g., at least 5 times the breathing rate) to track the $CO_2$ variation over time. The $CO_2$ concentration measurements may be used to demarcate each breath and thereby ascertain a resting respiration rate. The variability in respiration rate, together with the measurement history of the $O_2$ and $CO_2$ concentrations, may be used to determine when a subject's breathing is stable, thereby producing a reliable representation of the subject's resting RQ. In some embodiments, a history of a subject's resting respiration rate and/or a measurement of the subject's heart rate are used to distinguish resting RQ measurements from RQ measurements made during periods of activity or exercise.

Figure 22:
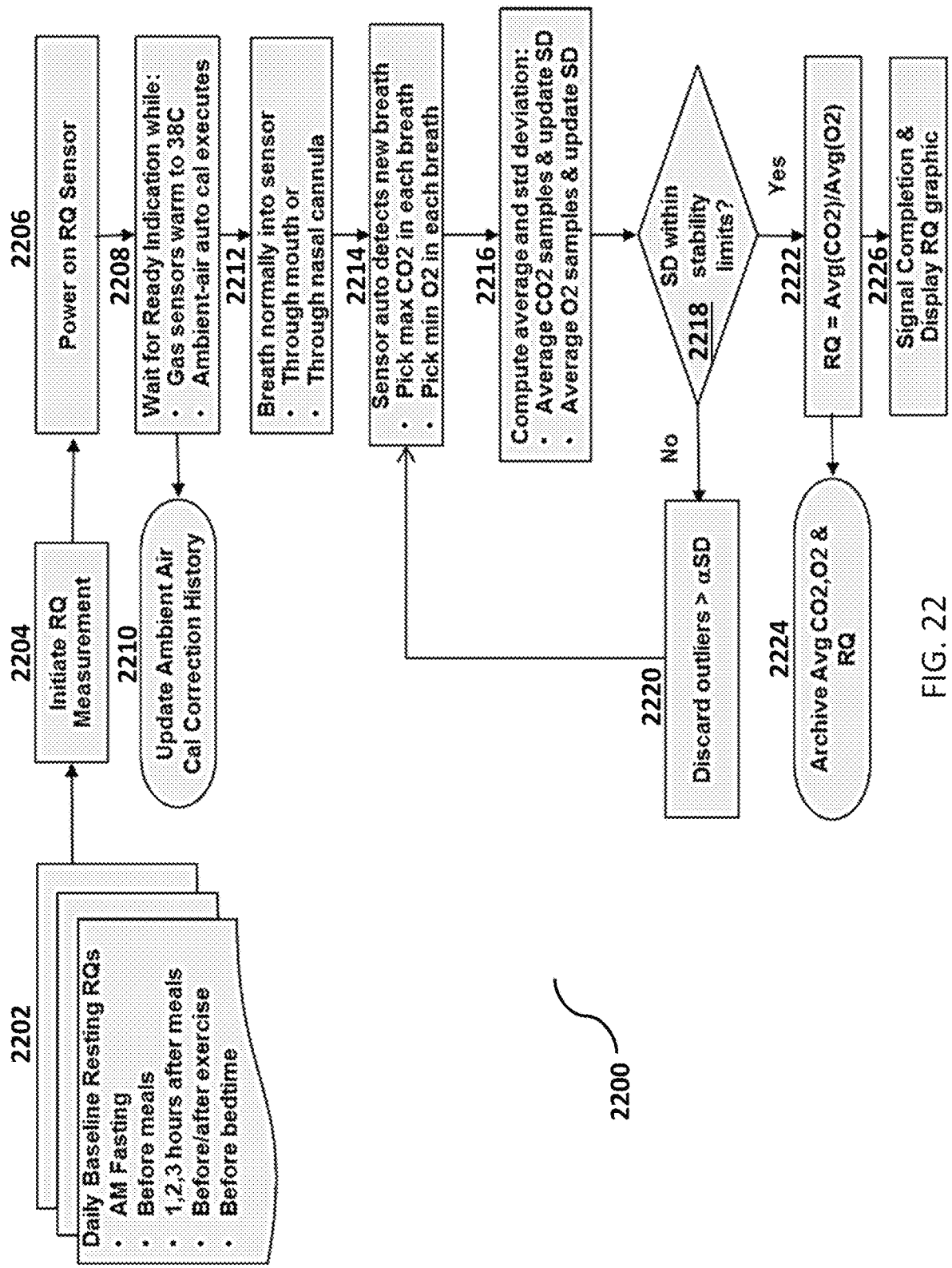
FIG. 22 is a process flow chart illustrating RQ measurement in accordance with some embodiments.

FIG. 22 is a process flow chart illustrating a method of RQ measurement 2200 in accordance with some embodiments. A daily baseline of resting RQs (e.g., upon waking, before/after meals, before/after exercise, and/or before bedtime) 2202 is maintained. In step 2204, RQ measurement is initiated. In step 2206, the RQ sensor is turned on. Once a ready indication is received in 2208, indicating that the gas sensors have warmed to 38° C. and/or ambient-air auto-calibration has executed, ambient air calibration correction history may be updated in step 2210. In step 2212, a user breathes normally into the sensor through a mouthpiece and/or nasal cannula. The sensor automatically detects new breath and determines maximum carbon dioxide in each breath and minimum oxygen in each breath in step 2214. Average carbon dioxide samples and standard deviations are computed as are average oxygen samples and standard deviations in step 2216. In step 2218, the standard deviations are compared to stability limits. If they fall outside, outliers are discarded in step 2220 and the process returns to step 2214. However, if they fall within, RQ is computed in step 2222, optionally archived in step 2224 (e.g., for further optimization), and RQ is displayed via an audio, graphic, or tactile indication 2226.

According to some embodiments, a subject may take RQ readings at various times throughout a day as defined by actual time and/or activity. For example, a subject may measure RQ before and/or after fasting, consuming food and/or drink, exercising, and/or sleeping. In some embodiments, a subject may measure RQ at specific time intervals including, but not limited to, 1 hour, 2 hours, 3 hours, 4 hours, 5 hours, 6 hours, 7 hours, 8 hours, 9 hours, 10 hours, 11 hours, or 12 hours before or after an activity.

In some embodiments, a subject breathes into an RQ device, through either a mouthpiece or a nasal cannula (e.g., in a hands-free configuration). At least one sensor detects new breaths, a maximum $CO_2$ concentration per breath, and/or a minimum $O_2$ concentration per breath. In some embodiments, an RQ device computes the average $CO_2$ concentration and the average $O_2$ concentration to determine a standard deviation (SD) of the readings. If the SD of the readings is within predefined limits, an RQ measurement may be output including, but not limited to, displayed, stored, and/or transmitted. If the SD of the readings is outside the predefined limits, the outlier readings may be discarded. In that case, the subject may continue to breathe into the RQ device until readings that fall within the acceptable SD range are collected.

In some embodiments, RQ measurements provide a way to finely monitor and tune a subject's metabolic state as a source of individual biofeedback. RQ values may impart: instant knowledge of the fraction of fat versus carbohydrate energy a subject is utilizing; an indication of whether a subject is in a de novo lipogenesis metabolic state (i.e., converting excess blood glucose into fat); (3) an indication of carbohydrate stress (implying high blood glucose levels); and/or (4) an understanding of glycogen capacity. These personal biofeedback indicators make it possible to track a subject's metabolic state and/or modify diet and exercise accordingly to, for example, achieve/maintain a weight goal, manage metabolic disease, and/or improve metabolic fitness and endurance.

Unlike calorie counting, in some embodiments, RQ measurements encourage diet and exercise adjustment by providing on-demand feedback regarding the impact of macronutrient choices and activity levels to avoid carbohydrate overloading that in turn leads to storage, rather than metabolic combustion, of dietary fats as well as conversion of glucose to stored fat via de novo lipogenesis, both of which contribute eventually to obesity. In some embodiments the personalized biofeedback capacity of the RQ measurement device is used to manage or reduce the likelihood of type 2 diabetes. RQ measurements may replace or reduce the frequency of capillary blood glucose measurements required to manage blood sugar. For example, resting RQ of 2:1.0 indicates high blood glucose (hyperglycemia), whereas resting RQ of about 0.7 indicates a range of normal to low blood glucose (hypoglycemia).

The use of routine RQ measurements also may support individual diagnostics. In some embodiments, a database of "normal" or historical levels of RQ measurements under various conditions (e.g., fasting, glucose challenge, postprandial, etc.) is maintained. When newly acquired RQ readings consistently vary from the normal or historical measurements, an indication of a loss of metabolic homeostasis may be provided to the subject or a clinician for early warning as to the onset of a disease state.

In some embodiments, RQ measurements may be used to monitor metabolic response.

Figure 23:
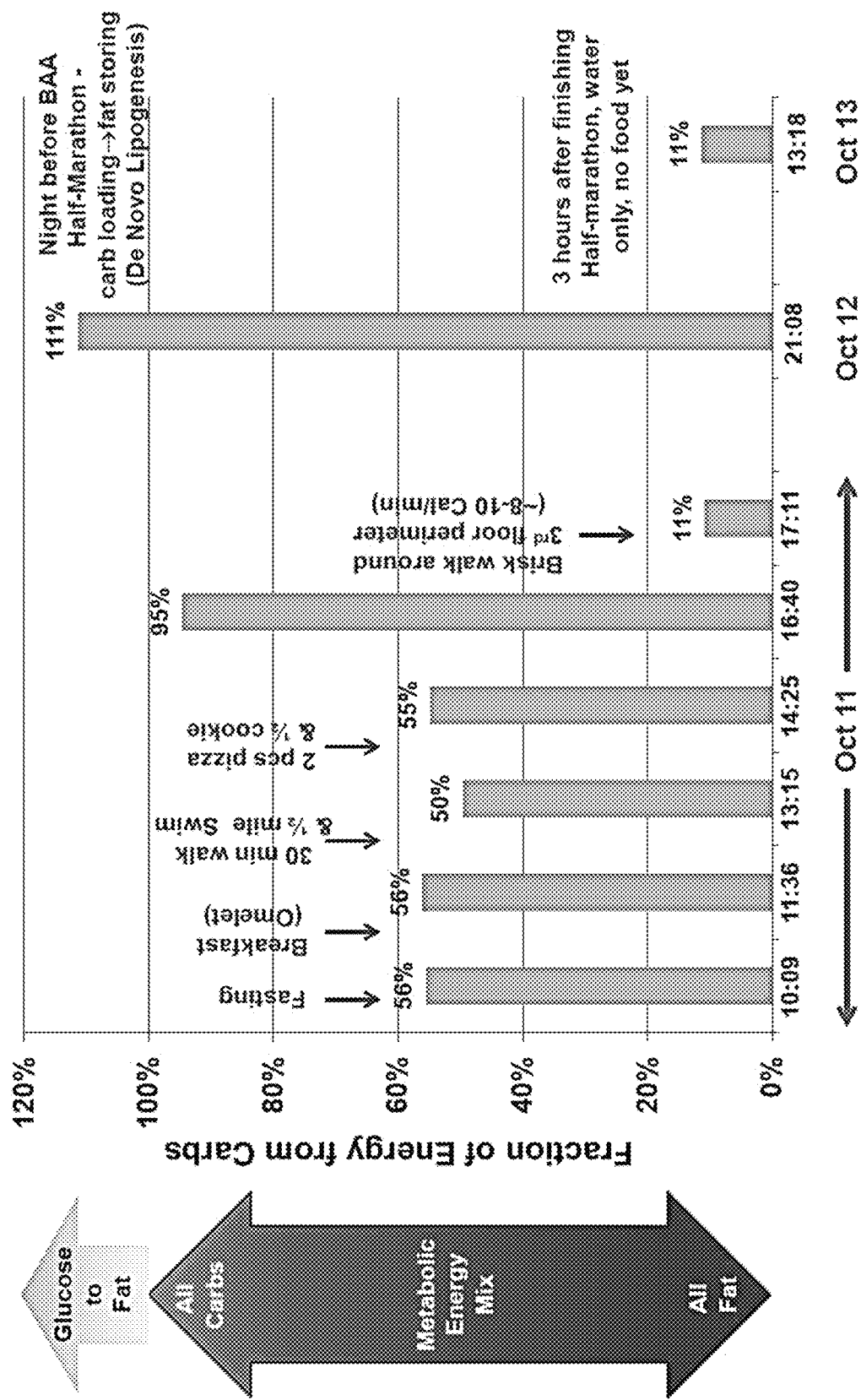
FIG. 23 is a graph illustrating RQ measurements from a subject over time in accordance with some embodiments.

FIG. 23 is a graph illustrating RQ measurements from a subject over three days in accordance with some embodiments. The subject is a healthy adult male human who had been training for a half-marathon at the time the RQ readings were collected. In FIG. 23, on October 11, two days prior to running the half-marathon, the subject's RQ values were measured at six separate times. First, the subject's fasting RQ was measured in the morning (10:09 AM), indicating that about 56% of the energy utilized by the subject was obtained from carbohydrates. After eating a low-carbohydrate breakfast (i.e., an omelet) (11:36 AM), still only 56% of the energy utilized by the subject was obtained from carbohydrates. Note that following a period of activity (i.e., thirty minutes of walking and swimming for half a mile) (1:15 PM), the carbohydrate-based energy utilized by the subject fell from about 56% to about 50%, indicating that the exercise affected the subject's metabolism, increasing the proportion of energy supplied from fat versus carbohydrates. At lunch the subject consumed a high carbohydrate meal (i.e., two pieces of pizza and half a cookie) (2:25 PM), after which the carbohydrate-based energy utilized by the subject began to rise, first to about 55% and, several hours later (4:40 PM), to about 95%. However, after further activity (i.e., a brisk walk) (5:11 PM), the carbohydrate-based energy utilized by the subject dropped to about 11%, indicating that the subject's metabolism was dominated by the low-intensity fat-burning exercise.

On October 12, the day before the half-marathon, the subject consumed large quantities of carbohydrates (i.e., "carb loading"). An RQ reading taken later that evening (9:08 PM) indicated an RQ greater than 1.0 implying that all of the energy utilized by the subject was obtained from carbohydrates. Furthermore, the subject was in a de novo lipogenesis metabolic state in which excessive blood glucose levels were being converted to stored fat. However, on October 13, three hours after completing the half-marathon and before eating, the carbohydrate-based energy utilized by the subject fell to 11%, indicating that the subject was again in a high fat burning state due to the combination of no food intake and depleted glycogen stores.

Figure 24:
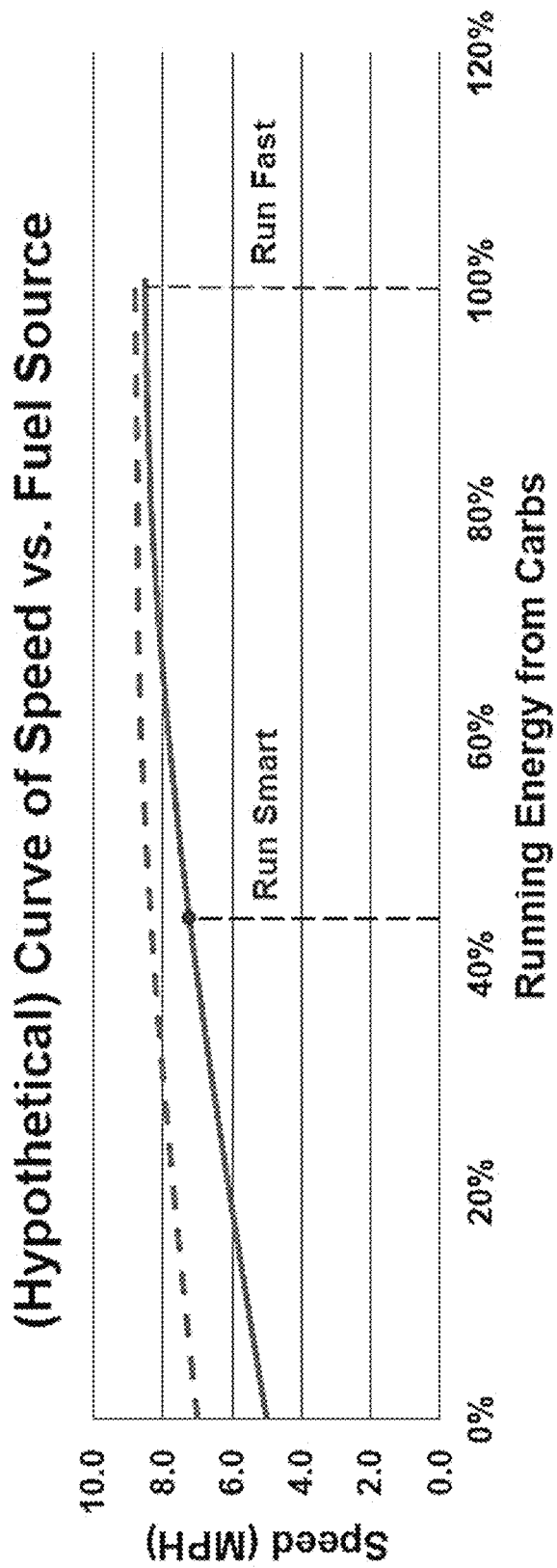
FIG. 24 is a graph illustrating (hypothetical) energy substrate utilization as it relates to speed/intensity of running in accordance with some embodiments.

In some embodiments, RQ measurements may be used to predict or provide a guideline or suggestion for performing an activity. FIG. 24 is a graph illustrating representative metabolic fuel utilization as it relates to speed/intensity in accordance with some embodiments. In particular, FIG. 24 illustrates the utility of measuring RQ for the assessment of optimal running speed in a hypothetical marathon scenario. To first order, a runner burns about the same calories per unit distance regardless of speed (i.e., at high speed the distance is covered in less time but requires a higher level of exertion than at lower speeds). In the absence of nutritional supplements, running at maximum speed may deplete the runner's circulating blood glucose and glycogen stores, a phenomenon known as "bonking" or "hitting the wall", after which speed and performance drop precipitously. As implied in FIG. 24 and illustrated by TABLE 7, knowledge of RQ versus running speed, enables a runner to select a pace to achieve an appropriate mix of fuels (e.g., fats plus carbohydrates versus carbohydrates alone) in order to delay or avoid glycogen depletion (i.e., running smart) and thus achieve better overall performance than simply running at maximum intensity (i.e., running fast).

TABLE 7

| Parameter | Run Fast | Run Smart |
| --- | --- | --- |
| Calories expended (per mile) | 130 | 130 |
| Initial glycogen reserves (Calories) | 1500 | 1500 |
| Initial speed (mph) | 8.5 | 7.2 |
| Initial pace (min:sec per mile) | 7:04 | 8:17 |
| Distance to glycogen depletion (miles) | 11.5 | 26.2 |
| Peak RQ during 26.2 mi race | 1.00 | 0.83 |
| Average RQ over 26.2 mi race | 0.80 | 0.83 |
| Average speed over 26.2 mi race (mph) | 6.1 | 7.2 |
| Average pace over 26.2 mi race (min:sec per mile) | 9:50 | 8:17 |
| Finish time (hr:min) | 4:16 | 3:37 |

Figure 25:
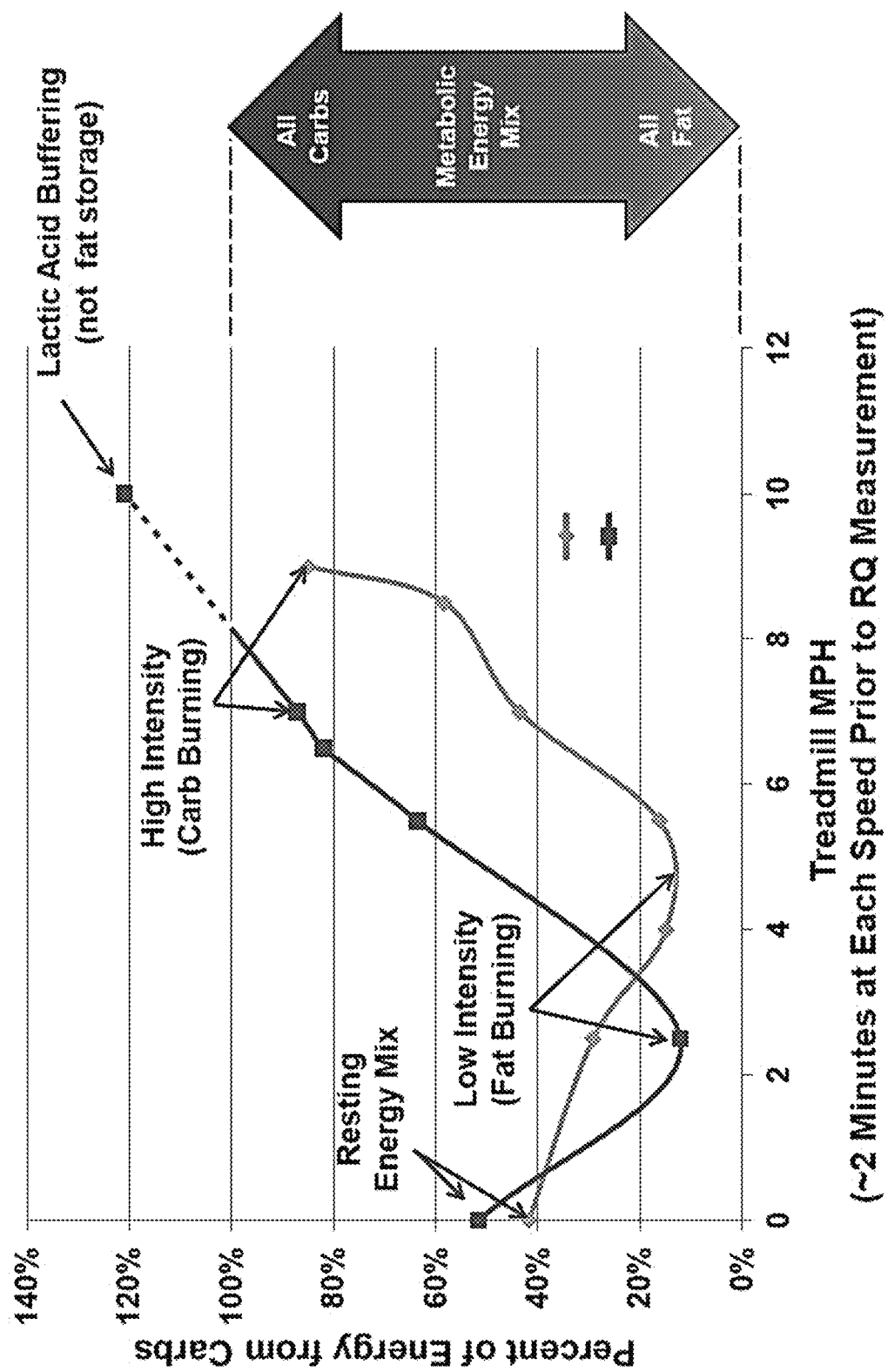
FIG. 25 is a graph illustrating energy utilization from carbohydrates in two subjects while increasing speed on a treadmill in accordance with some embodiments.

In some embodiments, RQ measurements may provide a predictive measure of a subject's endurance. FIG. 25 is a graph illustrating energy utilization from carbohydrates in two subjects moving on a treadmill at incrementally increasing speeds in accordance with some embodiments. Both subjects are healthy adult male humans with resting energy expenditures from carbohydrates of about 41% and about 52%, respectively. RQ values were measured at each speed, approximately every two minutes. The RQ readings indicate that a subject with the lower resting RQ (i.e., a lower percentage energy usage from carbohydrates) is able to maintain a higher treadmill speed prior to reaching an all carbohydrate energy consumption state. This anecdotal example also underscores the fact that individual metabolisms are unique and thus benefit from personalized, on-demand information about metabolic state, rather than prescriptive, formulaic diets and exercise regimens.

Figure 26A:
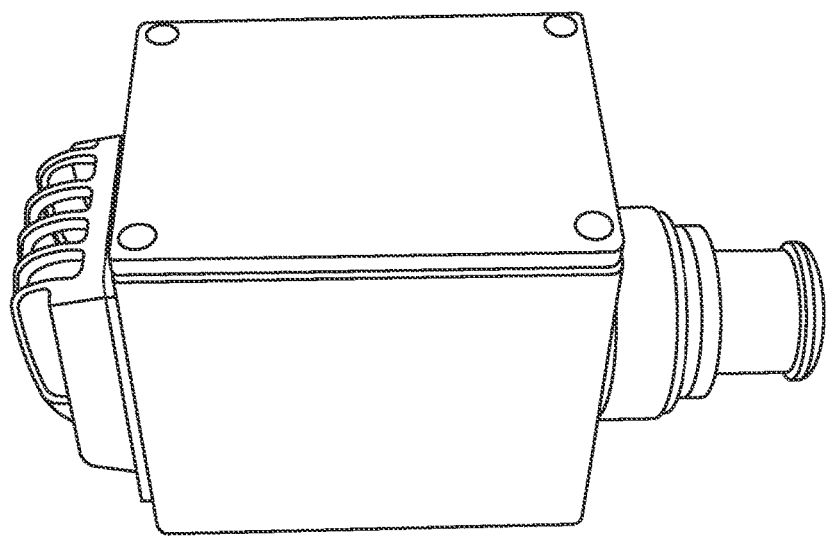
FIG. 26A is an image illustrating another RQ sensor prototype in accordance with some embodiments.
Figure 26B:
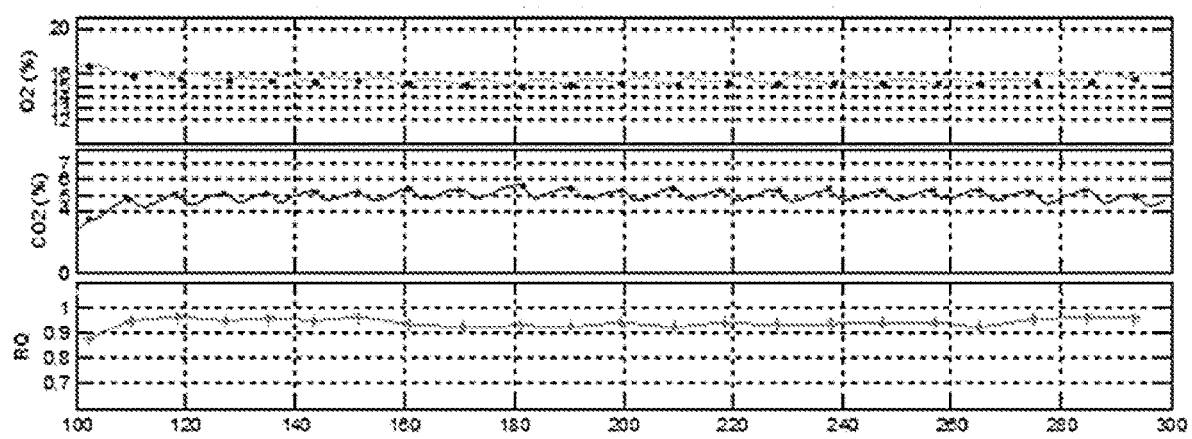
FIG. 26B is a series of representative plots illustrating the breath-by-breath data and RQ obtained with the sensor shown in FIG. 26A in accordance with some embodiments.

FIG. 26A is an image illustrating another RQ sensor prototype in accordance with some embodiments. The sensor employs optical techniques to determine the concentration of oxygen and carbon dioxide in expired breath and consequently does not require expendables. The sensor measures the oxygen consumed and carbon dioxide produced by averaging several breaths to account for short-term ventilation effects. FIG. 26B is a series of representative plots illustrating the breath-by-breath data and RQ obtained with the sensor shown in FIG. 26A in accordance with some embodiments. For purposes of illustration, the elapsed time for the measurements shown in FIG. 26B is a little over three minutes, but a shorter measurement, on the order of 30-60 s is adequate to provide a stable estimate of RQ. Note from the plots in FIG. 26B that while there is some variation in RQ the average is 0.93, indicating that a majority (77%) of the metabolic energy during the measurement is being derived from carbohydrate burning.

A key application envisioned for such as sensor is to provide daily or even hourly feedback to the user regarding dominant source of metabolic energy, essentially their metabolic energy zone. In terms of weight loss by reduction of adipose tissue, an RQ that hovers around 1.0 throughout the day implies that there is little energy being derived from fat and what energy is derived from fat is probably coming from circulating dietary fat rather than the stored fat that is the objective of the weight loss effort. Over-consumption of carbs, where overconsumption is dependent on the individual metabolism and energy needs, may even lead to an RQ>1, which is indicative of carbs being converted and stored as fat for future energy needs. Thus a necessary, but not sufficient, condition for weight loss through reduction of stored fat is for the RQ to be below 1. The lower the RQ, the greater percentage of energy derived from fat and, if the individual is not overconsuming dietary fat, the energy will be derived from stored fat producing weight loss.

By design, the metabolic model is intended to capture salient metabolic performance with the least amount of complexity. Consequently, there are many options for augmenting the model with additional modules (thus raising complexity) in order to simulate metabolic performance with greater detail or over a wider range of dietary inputs and activity levels.

A personal RQ sensor, coupled with a metabolic modeled tailored to the individual, provides a basis for developing more effective regimens for weight loss, diabetes management, and athletic training programs. Rather than a one-size fits all formulaic diet for weight loss, the metabolic model and sensor provide the quantitative tools to tailor macronutrient intake and exercise activity to achieve weight loss and weight management goals. A non-invasive personal RQ sensor has the potential to detect and track episodes of high blood glucose reducing the frequency of capillary blood testing and providing a higher density of data to correlate against dietary intake and activity in order to develop an individualized predictive model.

Passive Side-Stream Sampling

Existing breath-by-breath metabolic sensors employ relatively fast and expensive gas sensors (e.g., with sample rate time constants on the order of 150 ms or less to track variations in $O_2$ and $CO_2$ gas concentrations over the course of a breath) and/or active pumps to sample and deliver exhalant to the measurement chamber at a constant volume rate.

According to some embodiments, a passive side-stream sampling system may achieve accurate RQ and energy expenditure estimates using slower, less expensive, smaller, lighter, and/or lower power gas sensors and a low-cost and/or low-power differential pressure sensor.

Figure 27:
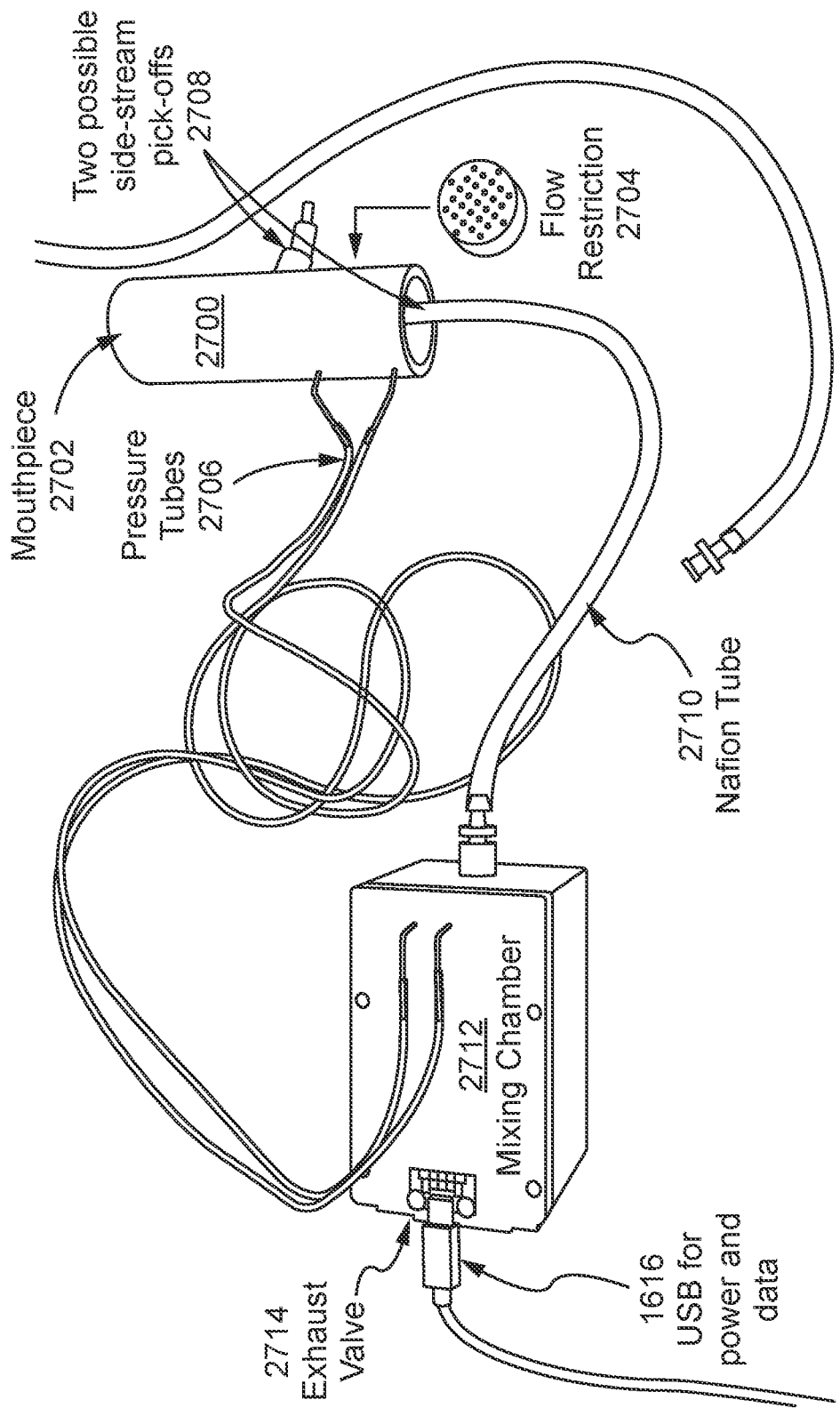
FIG. 27 is an image illustrating components of a passive side-stream sampling system in accordance with some embodiments.

FIG. 27 is an image illustrating components of a passive side-stream sampling system according to some embodiments. In FIG. 27, a sample tube 2700 includes a mouthpiece 2702 and a flow restrictor or venture 2704. Two pressure tubes 2706 connected to a differential pressure flow sensor are used to measure the volumetric flow of inhaled and exhaled breath. Venture 2704 is configured to create a back pressure which forces a small fraction (e.g., a few percent) of the exhaled air into at least one side-stream pick-off 2708 into a tube 2710 connected to a mixing chamber 2712 where the $O_2$ and $CO_2$ gas concentrations are measured. In some embodiments, the flow restrictor 2704 provides a linear pressure/flow relationship, which then provides a stable sidestream gas splitting fraction over the entire breath flow range. In other embodiments, the flow restrictor 2704 provides a more quadratic pressure/flow relationship, so the sidestream fraction increases at higher breath flow rates as compared to lower flow rates. In some embodiments, tube 2710 comprises a water vapor- and temperature-permeable polymer membrane, such as Nafion® tubing, configured to reduce and/or equilibrate both the temperature and humidity of the exhaled breath sample with ambient conditions. The rate of flow of the breath sample into mixing chamber 2712 may be set proportional to the flow rate of the exhaled air, thereby implementing proportional analog sampling of each breath without the need for an active pump. In some embodiments, several breaths may be required to displace all of the air in mixing chamber 2712, so the chamber acts as a breath gas integrator in which the $O_2$ and $CO_2$ gas concentrations are averaged via mixing over several breaths and the rate of change is commensurate with the time constants of slower gas sensors. A key element of the mixing chamber design is a low-cracking pressure (e.g., <about 1 mm $H_2O$) exit or exhaust valve 2714 to sustain breath sampling even at low pressures developed by the flow restrictor 2704 encountered toward the end of an exhale when the breath flow is low. The advantage of a sidestream flow consisting of a fixed-fraction of the mainstream breath flow is that it allows gas averaging over the entire breath flow composition range, spanning from anatomical dead space gas through end-tidal alveolar gas. This provides the same functionality of a Douglas bag sampling system, but in a much more compact and portable form factor. In some embodiments, a Universal Serial Bus (USB) cable 2716 or another connector, cable, and/or protocol may be used for connection, communication, and/or power supply between mixing chamber 2712 and, for example, a processor, memory, and/or energy storage device.

Figure 28B:
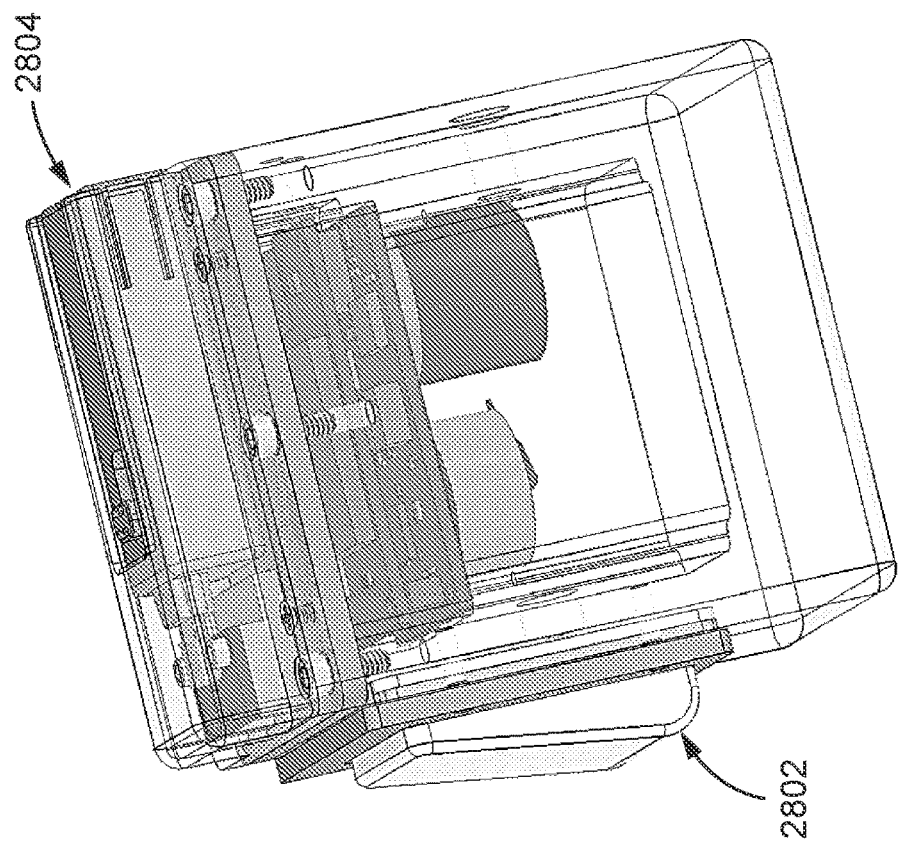
FIG. 28A is an image and FIG. 28B is a perspective wireframe view of a mixing chamber for the passive side-stream system of FIG. 27 in accordance with some embodiments.
Figure 28A:
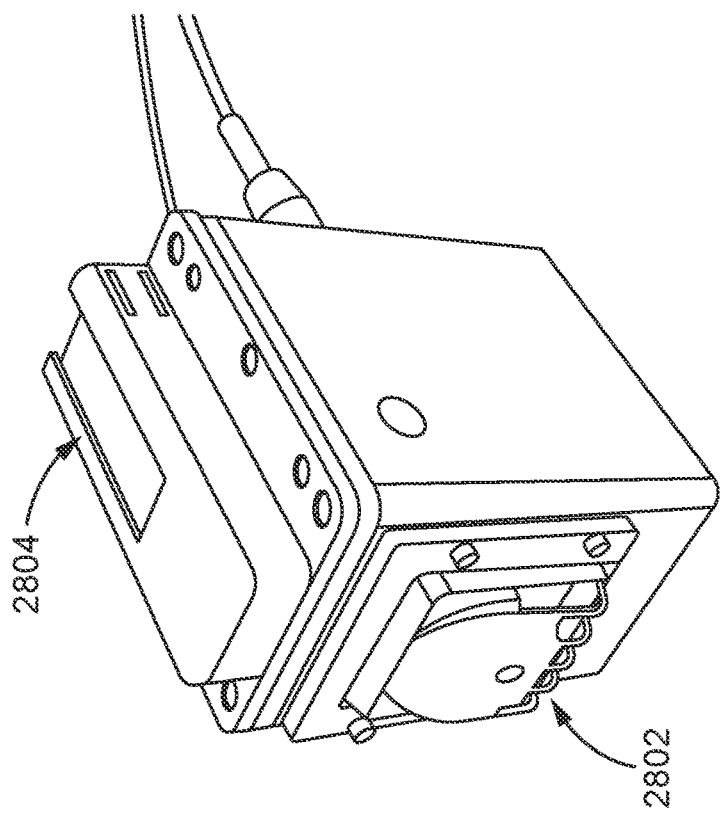

FIG. 28A is an image and FIG. 28B is a perspective wireframe view of a breath sensing system which includes a mixing chamber in accordance with some embodiments. In FIGS. 28A and 28B, the mixing chamber includes an exhaust valve 2802 and replaceable battery 2804, which could also be a rechargeable battery. In some embodiments, a breath sensing system may be configured for connection to a battery, a wired or wireless connection to a battery carried elsewhere on a user's body or located nearby, or a connection to an external power supply (e.g., an AC plug). In some embodiments, this electrical connection includes a USB, FireWire®, and/or similar connectorized cable.

Figure 29A:
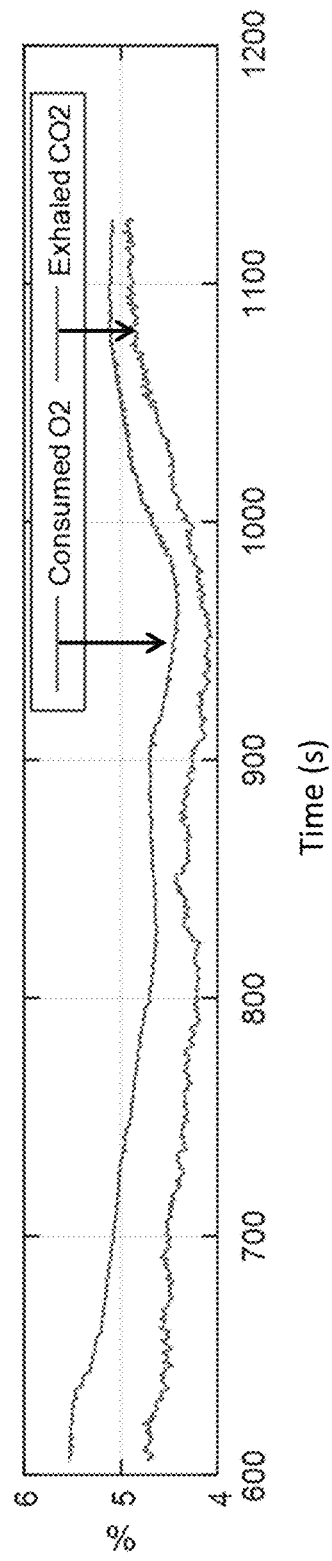
FIG. 29A is a representative plot illustrating O2 and CO2 gas concentration curves produced by a passive side-stream sampling sensor in accordance with some embodiments.
Figure 29B:
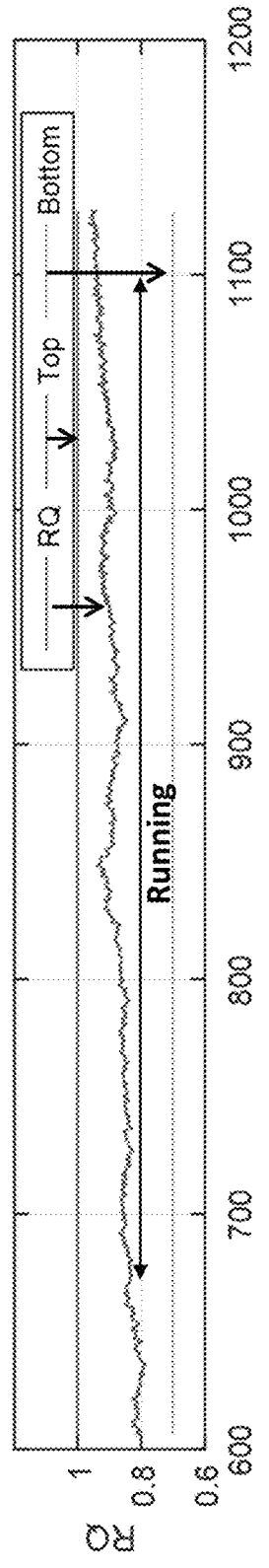
FIG. 29B is a representative plot illustrating respiratory quotient.
Figure 29C:
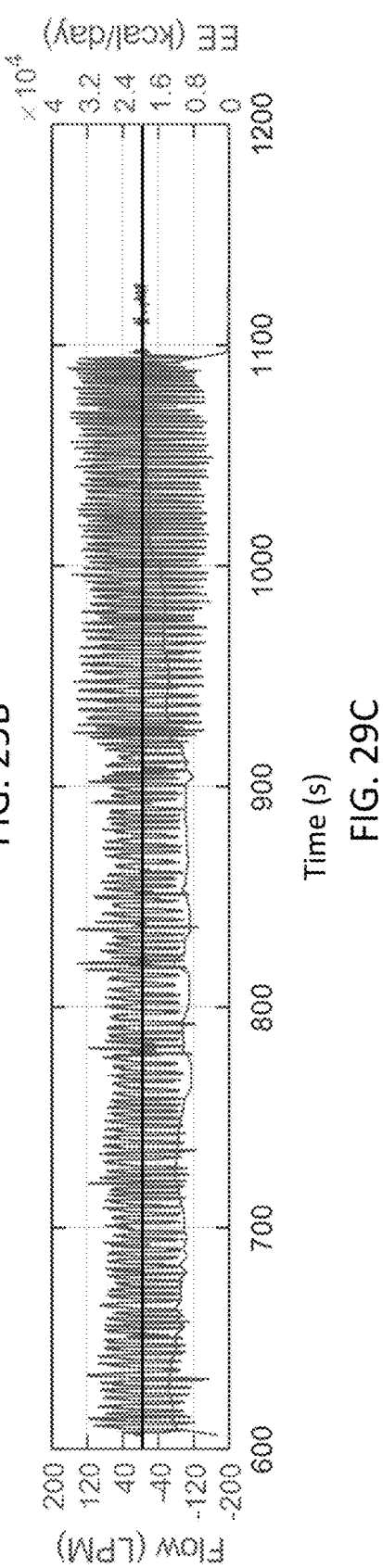
FIG. 29C is a plot of the corresponding breath volume rate and energy expenditure estimates associated with the data from the passive side-stream sampling sensor in accordance with some embodiments.

FIG. 29A is a representative plot illustrating O2 and CO2 gas concentration curves produced by a passive side-stream sampling sensor in accordance with some embodiments. FIG. 29B is a representative plot illustrating respiratory quotient, and FIG. 29C is a plot of the corresponding breath volume rate and energy expenditure estimates associated with the data from the passive side-stream sampling sensor in accordance with some embodiments.

According to some embodiments, the benefits of employing passive side-stream sampling with a miniature mixing chamber over breath-by-breath approaches include, but are not limited to, the following:

utilization of smaller, lighter, less expensive, and/or lower power gas sensors for greater system efficiency and/or mobility;

passive proportional gas concentration sampling of each breath instead of an active pump for greater system efficiency, mobility, and/or simplicity (especially with respect to calibration);

utilization of simple, low cost differential pressure flow sensor and single exhaust valve for greater system efficiency and/or simplicity;

reduced valve leakage due to low pressure of the sidestream sampling during inhalation for greater system efficiency and/or accuracy;

improved accounting for dead space contributions to expired breath via breath averaging in the mixing chamber for greater system efficiency and/or accuracy; and more reliable energy estimates based on matching the temporal dynamic of the gas concentrations to the time constants of the sensors for greater system efficiency and/or accuracy.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, embodiments of modeling, monitoring, and managing metabolism disclosed herein may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output.

Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All publications, patent applications, patents, and other references mentioned herein are incorporated by reference in their entirety, including, but not limited to, the following:

1. Acheson et al., *Am. J. Clin. Nutrition,* 48:240-47 (1988);
2. Bouchard et al., *Obesity Res.,* 2(5):400-10 (1994);
3. Cruickshank et al., *J. Physiol.,* 80(2):179-92 (1933);
4. Ganz et al., *Diabetology & Metabolic Syndrome,* 6(50):1-8 (2014);
5. Guh et al., *BMC Public Health,* 9(88):1-20 (2009);
6. Hargrove, *J. Nutrition,* 136(12):2957-61 (2006);
7. Jebb et al., *Am. J. Clin. Nutrition,* 58:455-62 (1993);
8. Ladenheim, *Drug Design, Dev. & Therapy,* 1867-75 (2015);
9. Ludwig et al., *JAMA,* 311(21):2167-68 (2014);
10. McDevitt et al., *Am. J. Clin. Nutrition,* 74(6):737-46 (2001);
11. Mozaffarian et al., *NEJM,* 364(25):2392-2404 (2011); and
12. Weiss et al., *N. Eng. J. Med.,* 350(23):2362-74 (2004).

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the terms "subject," "individual," "recipient," "host," "user," and the like are used interchangeably to refer to a either a human or an animal subject.

As used herein in the specification and in the claims, the term "metabolism" refers to biochemical processes whereby nutrients are converted to energy for use by a mammal. Metabolism can be further defined as including "catabolic" and "anabolic" processes. A catabolic process refers to biochemical events that occur in a mammal that result in the breaking apart of molecules. An anabolic process refers to biochemical events that occur in a mammal that result in the creation of molecules.

As used herein in the specification and in the claims, the term "metabolic disease" may include, but is not limited to, type 1 diabetes, type 2 diabetes, obesity, gout, lipid disorders, hyperthyroidism, hypothyroidism, dyslipidemia, hypolipidemia, galactosemia, phenylketonuria, metabolic syndrome, or phenylketonuria. Diabetes is a metabolic disease that results in excess sugar in the blood and urine. Type 1 diabetes is characterized by a destruction of the pancreatic beta cells that produce insulin. Type 2 diabetes is characterized by insulin resistance, wherein the insulin produced by the pancreatic beta cells is not efficiently utilized to convert glucose to other energy forms.

As used herein in the specification and in the claims, the term "sensor" refers to a transducer that detects an aspect of the environment and provides a corresponding output. The phrases "all-optical gas sensor" or "all-optical gas sensing" refer to a sensor(s) that utilizes optics in the detection of specific wavelengths (e.g., IR spectroscopy) for the detection of the presence of certain gases. One example of an all optical gas sensor is the $CO_2$ nondispersive infrared (NDIR) optical gas sensor.

As used herein in the specification and in the claims, the term "hands-free" refers to an ability of a user to operate or practice a system, apparatus, or method without, or with only minimal use, of the user's hand(s).

The invention claimed is:

1. An apparatus for measuring a respiratory quotient (RQ) level in a subject, the apparatus comprising:
   a first input port for receiving respired air from the subject;
   a measurement chamber for receiving the respired air from the first input port, the measurement chamber being in fluid communication with the first input port;
   a first sensor located in the measurement chamber, the first sensor for measuring a series of oxygen levels in the measurement chamber;
   a second sensor located in the measurement chamber, the second sensor for measuring a series of carbon dioxide levels in the measurement chamber at a temporal rate sufficient to ascertain a respiration rate of the subject, wherein the second sensor has a different time constant than the first sensor;
   at least one output interface;
   at least one memory for storing processor-executable instructions, the series of oxygen level measurements, and the series of carbon dioxide level measurements; and
   at least one processor coupled to the first sensor, the second sensor, the at least one output interface, and the at least one memory, wherein upon execution of the processor-executable instructions, the at least one processor:
      obtains a first portion of the series of carbon dioxide level measurements;
      determines a first respiration rate based on the first portion of the series of carbon dioxide level measurements;

iterates steps of obtaining a subsequent portion of the series of carbon dioxide level measurements, determining a subsequent respiration rate based on the subsequent portion of the series of carbon dioxide level measurements, and comparing the subsequent respiration rate to at least one prior respiration rate until a stable breathing pattern is identified;

obtains a stable breathing pattern portion of the series of oxygen level measurements and a stable breathing pattern portion of the series of carbon dioxide level measurements;

determines an average minimum oxygen level for a plurality of respiration cycles from the stable breathing pattern portion of the series of oxygen level measurements;

determines an average maximum carbon dioxide level for a plurality of respiration cycles from the stable breathing pattern portion of the series of carbon dioxide level measurements;

calculates the RQ level from the average minimum oxygen level and the average maximum carbon dioxide level; and at least one of displays and transmits, via the at least one output interface, the calculated RQ level.

2. The apparatus of claim 1, wherein the at least one processor controls an ambient air calibration process, the ambient air calibration process comprising:

comparing at least one measurement to at least one expected value for ambient air;

in response to determining that the at least one measurement is from the first sensor and sufficiently different from the at least one expected value for ambient air, performing a span calibration process on the first sensor to determine and apply a gain correction to subsequent measurements from the first sensor;

in response to determining that the at least one measurement is from the second sensor and sufficiently different from the at least one expected value for ambient air, performing a zero-point calibration process on the second sensor to determine and apply an offset correction to subsequent measurements from the second sensor.

3. The apparatus of claim 2, wherein the at least one expected value for ambient air at 760 mm Hg is at least one of:

about 19.5% (v/v) to about 23.5% (v/v) oxygen; and
about 250 ppm to about 5,000 ppm carbon dioxide.

4. The apparatus of claim 3, wherein the at least one expected value for ambient air at 760 mm Hg is at least one of:

about 20.9% (v/v) oxygen; and
about 400 ppm carbon dioxide.

5. The apparatus of claim 2, wherein the ambient air calibration process is performed each time the first sensor and the second sensor are initiated.

6. The apparatus of claim 2, wherein the ambient air calibration process further comprises storing in the at least one memory at least one of:

the gain correction applied to subsequent measurements from the first sensor; and
the offset correction applied to subsequent measurements from the second sensor, such that a history of ambient air measurement drift is maintained for reference.

7. The apparatus of claim 1, further comprising a second input port for receiving a carbon dioxide cartridge for calibrating at least one of the first sensor and the second sensor, the second input port being in fluid communication with the measurement chamber such that the measurement chamber receives carbon dioxide released from the carbon dioxide cartridge.

8. The apparatus of claim 7, wherein the at least one processor controls a full calibration process, the full calibration process comprising:

allowing the measurement chamber to fill with ambient air;
setting a span value for the first sensor to an expected value for the ambient air;
setting a zero-point value for the second sensor to an expected value for the ambient air;
coupling the second input port with the carbon dioxide cartridge for releasing carbon dioxide from the carbon dioxide cartridge;
releasing the carbon dioxide into the measurement chamber;
setting a zero-point value for the first sensor to zero once the carbon dioxide displaces the ambient air in the measurement chamber; and
iteratively measuring oxygen levels with the first sensor in the measurement chamber as the ambient air displaces the carbon dioxide in the measurement chamber until a predetermined oxygen level is measured, the predetermined oxygen level indicating the span value for the second sensor.

9. The apparatus of claim 8, wherein:
the predetermined oxygen level is about 16.7%; and
the span value for the second sensor is about 20%.

10. The apparatus of claim 1, further comprising a component configured to:

prevent fluid communication between the first input port and the measurement chamber during an initial portion of each respiration cycle; and
allow fluid communication between the first input port and the measurement chamber during an end-tidal portion of each respiration cycle.

11. The apparatus of claim 10, wherein the component is at least one of a mechanical shutter, a vacuum pump, and a purge fan.

12. The apparatus of claim 1, wherein the first input port is compatible with at least one of a mouthpiece and a sample tube for coupling the input port to at least one of the mouth and a nostril of the subject.

13. The apparatus of claim 12, wherein the at least one of the mouthpiece and the sample tube is at least one of disposable and for hands-free use.

14. The apparatus of claim 12, wherein the mouthpiece is a repurposed sport bottle cap.

15. The apparatus of claim 1, further comprising a heating element for at least one of preventing and reducing condensation on the first sensor and the second sensor.

16. The apparatus of claim 1, wherein upon execution of the processor-executable instructions, the at least one processor further:

provides feedback indicative of a real-time metabolic state of the subject based on the calculated RQ level.

17. The apparatus of claim 16, wherein upon execution of the processor-executable instructions, the at least one processor further:

guides the subject's macronutrient intake and/or activity level to promote a desired metabolic state of the subject.

18. The apparatus of claim 1, wherein upon execution of the processor-executable instructions, the at least one processor further:

determines, based on the calculated RQ level input into a nonlinear feedback model, a target value of at least one energy substrate utilization variable that at least one of maintains or increases energy utilization in the subject.

19. The apparatus of claim 18, wherein the nonlinear feedback model is tailored to the subject.

20. The apparatus of claim 18, wherein the at least one energy substrate utilization value includes at least one of a macronutrient composition and caloric value of food consumed by the subject or intensity and duration of activity by the subject.

21. The apparatus of claim 18, wherein the nonlinear feedback model guides the subject's macronutrient intake and/or activity levels to promote a desired metabolic state and/or achieve and maintain a healthy body weight.

22. A kit for measuring a respiratory quotient (RQ) level in a subject, the kit comprising:
a carbon dioxide cartridge;
at least one of a mouthpiece and a sample tube for coupling to at least one of the mouth and a nostril of the subject; and
a device for measuring the RQ level in a subject, the device including:
a first input port for receiving, via the at least one of the mouthpiece and the sample tube, respired air from the subject;
a measurement chamber for receiving the respired air from the first input port, the measurement chamber being in fluid communication with the first input port;
a first sensor located in the measurement chamber, the first sensor for measuring a series of oxygen levels in the measurement chamber;
a second sensor located in the measurement chamber, the second sensor for measuring a series of carbon dioxide levels in the measurement chamber at a temporal rate sufficient to ascertain a respiration rate of the subject, wherein the second sensor has a different time constant than the first sensor;
a second input port for receiving the carbon dioxide cartridge for calibrating at least one of the first sensor and the second sensor, the second input port being in fluid communication with the measurement chamber such that the measurement chamber receives carbon dioxide released from the carbon dioxide cartridge;
at least one output interface;
at least one memory for storing processor-executable instructions, the series of oxygen level measurements, and the series of carbon dioxide level measurements; and
at least one processor coupled to the first sensor, the second sensor, the at least one output interface, and the at least one memory, wherein upon execution of the processor-executable instructions, the at least one processor:
obtains a first portion of the series of carbon dioxide level measurements;
determines a first respiration rate based on the first portion of the series of carbon dioxide level measurements;
iterates steps of obtaining a subsequent portion of the series of carbon dioxide level measurements, determining a subsequent respiration rate based on the subsequent portion of the series of carbon dioxide level measurements, and comparing the subsequent respiration rate to at least one prior respiration rate until a stable breathing pattern is identified;
obtains a stable breathing pattern portion of the series of oxygen level measurements and a stable breathing pattern portion of the series of carbon dioxide level measurements;
determines an average minimum oxygen level for a plurality of respiration cycles from the stable breathing pattern portion of the series of oxygen level measurements;
determines an average maximum carbon dioxide level for a plurality of respiration cycles from the stable breathing pattern portion of the series of carbon dioxide level measurements;
calculates the RQ level from the average minimum oxygen level and the average maximum carbon dioxide level; and
at least one of displays and transmits, via the at least one output interface, the calculated RQ level.

23. An apparatus for measuring a respiratory quotient (RQ) level in a subject, the apparatus comprising:
a first input port for receiving respired air from the subject;
a measurement chamber for receiving the respired air from the first input port, the measurement chamber being in fluid communication with the first input port;
a first sensor located in the measurement chamber, the first sensor for measuring a series of oxygen levels in the measurement chamber;
a second sensor located in the measurement chamber, the second sensor for measuring a series of carbon dioxide levels in the measurement chamber at a temporal rate sufficient to ascertain a respiration rate of the subject;
at least one output interface;
at least one memory for storing processor-executable instructions, the series of oxygen level measurements, and the series of carbon dioxide level measurements;
at least one processor coupled to the first sensor, the second sensor, the at least one output interface, and the at least one memory, wherein upon execution of the processor-executable instructions, the at least one processor:
obtains a first portion of the series of carbon dioxide level measurements;
determines a first respiration rate based on the first portion of the series of carbon dioxide level measurements;
iterates steps of obtaining a subsequent portion of the series of carbon dioxide level measurements, determining a subsequent respiration rate based on the subsequent portion of the series of carbon dioxide level measurements, and comparing the subsequent respiration rate to at least one prior respiration rate until a stable breathing pattern is identified;
obtains a stable breathing pattern portion of the series of oxygen level measurements and a stable breathing pattern portion of the series of carbon dioxide level measurements;
determines an average minimum oxygen level for a plurality of respiration cycles from the stable breathing pattern portion of the series of oxygen level measurements;
determines an average maximum carbon dioxide level for a plurality of respiration cycles from the stable breathing pattern portion of the series of carbon dioxide level measurements;

calculates the RQ level from the average minimum oxygen level and the average maximum carbon dioxide level; and at least one of displays and transmits, via the at least one output interface, the calculated RQ level; and a second input port for receiving a carbon dioxide cartridge for calibrating at least one of the first sensor and the second sensor, the second input port being in fluid communication with the measurement chamber such that the measurement chamber receives carbon dioxide released from the carbon dioxide cartridge, wherein the at least one processor controls a full calibration process, the full calibration process comprising:

allowing the measurement chamber to fill with ambient air;

setting a span value for the first sensor to an expected value for the ambient air;

setting a zero-point value for the second sensor to an expected value for the ambient air;

coupling the second input port with the carbon dioxide cartridge for releasing carbon dioxide from the carbon dioxide cartridge;

releasing the carbon dioxide into the measurement chamber;

setting a zero-point value for the first sensor to zero once the carbon dioxide displaces the ambient air in the measurement chamber; and iteratively measuring oxygen levels with the first sensor in the measurement chamber as the ambient air displaces the carbon dioxide in the measurement chamber until a predetermined oxygen level is measured, the predetermined oxygen level indicating the span value for the second sensor.

24. The apparatus of claim 23, wherein:
the predetermined oxygen level is about 16.7%; and
the span value for the second sensor is about 20%.

25. The apparatus of claim 23, wherein upon execution of the processor-executable instructions, the at least one processor further:
provides feedback indicative of a real-time metabolic state of the subject based on the calculated RQ level.

26. The apparatus of claim 25, wherein upon execution of the processor-executable instructions, the at least one processor further:
guides the subject's macronutrient intake and/or activity level to promote a desired metabolic state of the subject.

27. The apparatus of claim 23, wherein upon execution of the processor-executable instructions, the at least one processor further:
determines, based on the calculated RQ level input into a nonlinear feedback model, a target value of at least one energy substrate utilization variable that at least one of maintains or increases energy utilization in the subject.

28. The apparatus of claim 27, wherein the nonlinear feedback model is tailored to the subject.

29. The apparatus of claim 27, wherein the at least one energy substrate utilization value includes at least one of a macronutrient composition and caloric value of food consumed by the subject or intensity and duration of activity by the subject.

30. The apparatus of claim 27, wherein the nonlinear feedback model guides the subject's macronutrient intake and/or activity levels to promote a desired metabolic state and/or achieve and maintain a healthy body weight.

* * * * *